US012636296B1

(12) United States Patent
Haghdoost et al.

(10) Patent No.: US 12,636,296 B1
(45) Date of Patent: May 26, 2026

(54) CANNABINOL ANALOGS AND THEIR USE AS PHARMACOLOGICALLY ACTIVE AGENTS

(71) Applicant: Nalu Bio, Inc., San Francisco, CA (US)

(72) Inventors: Mehdi Haghdoost, Stittsville (CA); Caitlyn Krebs, San Francisco, CA (US); Grazia Piizzi, Brookline, MA (US); Phyllis Whiteley, Los Gatos, CA (US)

(73) Assignee: Nalu Bio, Inc., San Francisco, CA (US)

( * ) Notice: Subject to any disclaimer, the term of this patent is extended or adjusted under 35 U.S.C. 154(b) by 0 days.

(21) Appl. No.: 19/272,929

(22) Filed: Jul. 17, 2025

(51) Int. Cl.
*A61K 31/00* (2006.01)
*A61K 9/00* (2006.01)
*A61K 9/02* (2006.01)
*C07D 311/80* (2006.01)

(52) U.S. Cl.
CPC .......... *A61K 31/658* (2023.05); *A61K 9/0056* (2013.01); *A61K 9/02* (2013.01); *C07D 311/80* (2013.01)

(58) Field of Classification Search
None
See application file for complete search history.

(56) References Cited

U.S. PATENT DOCUMENTS

| | | | |
|---|---|---|---|
| 9,580,400 | B2 | 2/2017 | Makriyannis et al. |
| 2009/0203725 | A1 | 8/2009 | Van Oeveren et al. |
| 2021/0284621 | A1 | 9/2021 | Moshos et al. |
| 2022/0106284 | A1 | 4/2022 | Grenning et al. |
| 2022/0242856 | A1 | 8/2022 | Ahmar et al. |
| 2022/0340582 | A1 | 10/2022 | Ahmar et al. |
| 2023/0026772 | A1 | 1/2023 | Sanders et al. |
| 2023/0373942 | A1 | 11/2023 | Berkowitz et al. |
| 2024/0139215 | A1 | 5/2024 | Nowak et al. |
| 2024/0174627 | A1 | 5/2024 | Abdur-Rashid et al. |

*Primary Examiner* — Sarah Pihonak
*Assistant Examiner* — Donna M Nestor
(74) *Attorney, Agent, or Firm* — Dianne E. Reed; VLP Law Group LLP

(57) ABSTRACT

Disclosed herein are novel cannabinol (CBN) analogs, each exhibiting a difference in the level and/or type of interaction with the CB1 receptor as compared with the CB2 receptor, and, as such, provide for a significant reduction in psychoactive effects relative to CBN per se. Also provided are pharmaceutical formulations comprising at least one CBN analog of the invention, at least one optional pharmaceutically acceptable excipient, and, also optionally, an additional beneficial agent, along with methods for treating a subject affected by a condition, disorder, or disease responsive to administration of the CBN analog. Exemplary methods of use include treatment of pain, treatment of endometriosis, treatment of inflammation, and a method for inducing weight loss.

17 Claims, 11 Drawing Sheets

CBN Analog (1):

CBN Analog (1):

CBN Analog (2):

CBN Analog (2):

CBN Analog (3):

CBN Analog (3):

CBN Analog (1):

CBN Analog (3):

CANNABINOL ANALOGS AND THEIR USE AS PHARMACOLOGICALLY ACTIVE AGENTS

TECHNICAL FIELD

The present invention relates generally to cannabinoids, and more particularly relates to pharmacologically active cannabinol analogs having novel molecular structures. The invention has utility in the fields of medicine, medicinal chemistry, therapeutics, and chemical and pharmaceutical manufacturing.

BACKGROUND

Medical *cannabis* has received extensive attention in the media and the scientific literature. More recently, individual plant cannabinoids isolated from the *Cannabis sativa* (C. *Sativa*) plant have been researched and proposed for use in many medicinal contexts. These plant cannabinoids include compounds such as cannabidiol (CBD), cannabinol (CBN), cannabichromene (CBC), cannabidiolic acid (CBDA), tetrahydrocannabinolic acid ($\Delta^9$-THCA), tetrahydrocannabiphorol (THCP), (−)-trans-$\Delta^9$-tetrahydrocannabivarin (also referred to herein as $\Delta^9$-tetrahydrocannabivarin or $\Delta^9$-THCV), tetrahydrocannabivarinic acid (THCVA), and $\Delta^9$-tetrahydrocannabinol ($\Delta^9$-THC).

The potential medicinal properties of cannabinoids are attributed to specific interaction with the $CB_1$ and $CB_2$ receptors as well as many other receptors of the endocannabinoid system. These receptors are located in the brain and throughout the central and peripheral nervous systems. Activation of the $CB_1$ receptors, in particular, leads to inhibition of adenylyl cyclase activity and blockade of voltage-operated calcium channels, thereby suppressing neuronal excitability and serotonin neurotransmission inhibition. As a result, it has been suggested that cannabinoids that activate $CB_1$ receptors have potential utility in treatment of depression, neurological diseases, chronic pain, multiple sclerosis, glaucoma, and other conditions. See, e.g., Abioye et al. (2020), "$\Delta^9$-tetrahydrocannabivarin: a commentary on potential therapeutic benefit for the management of obesity and diabetes," *J. Cannabis Res.* 2:1-6. CBN perse is also a cannabinoid that has garnered some interest:

CBN

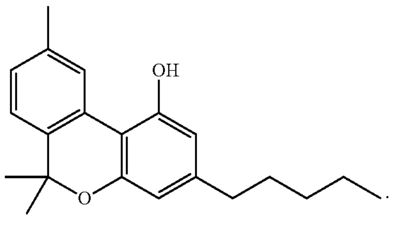

Like $\Delta^9$-THC, CBN is a phytocannabinoid that is somewhat psychoactive, which, in turn, renders both compounds generally unsuitable as mainstream pharmaceutical agents, despite their numerous beneficial properties. The psychoactive effects are believed to result from the fact that both $\Delta^9$-THC and CBN are partial agonists at both the $CB_1$ and $CB_2$ receptors (with somewhat greater affinity at the $CB_1$ receptor and greater selectivity at $CB_2$ receptors; see Rhee et al. (1997) *J. Med. Chem.* 40(20): 3228-33). There is, accordingly, a need for agents that provide the beneficial properties associated with CBN or other cannabinoids without the side effects typically seen with $\Delta^9$-THC and CBN.

SUMMARY OF THE INVENTION

The invention is directed to the above-mentioned need in the art and, in one embodiment, provides a novel CBN analog a compound having the structure of formula (I)

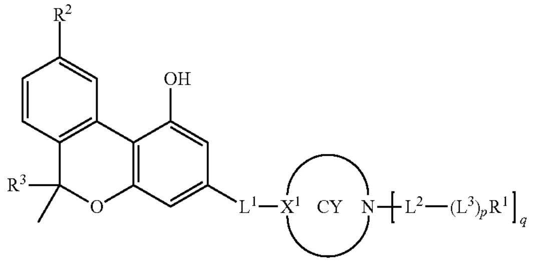

wherein:

$L^1$ is selected from $C_1$-$C_3$ alkylene, $C_2$-$C_3$ alkenylene, hydroxyl-substituted $C_1$-$C_3$ alkylene, hydroxyl-substituted $C_2$-$C_3$ alkenylene, fluorinated $C_1$-$C_3$ alkylene, fluorinated $C_2$-$C_3$ alkenylene, —O—, —(CO)—, —($SO_2$)—, —$NR^4$—, —$NR^4$—(CO)—, —(CO)—$NR^4$—, -and $NR^5$—(CO)—$NR^6$— wherein $R^4$, $R_5$, and $R^6$ are H or $C_1$-$C_3$ alkyl and $R^5$ and $R^6$ may be the same or different;

$L^2$ is selected from —(CO)— and —($SO_2$)—;

$L^3$ is selected from —$CH_2$—, —NH—$CH_2$—, and —$CH_2$—N—;

p is zero or 1, such that $L^3$ may be absent or present in the molecular structure;

CY comprises a monocyclic or bicyclic group comprising 4-10 ring atoms and zero to 4 nonhydrogen substituents, any two of which may be linked to form a bridged bicyclic moiety, wherein CY is aliphatic or aromatic and further comprises zero to 3 additional heteroatoms, i.e., zero to 3 heteroatoms in addition to the ring nitrogen atom in (1);

$X^1$ is selected from N, C, and CH, wherein when CY is aromatic, $X^1$ is N or C;

q is zero or 1;

$R^1$ comprises $C_1$-$C_6$ alkyl, $C_2$-$C_6$ alkenyl, $C_2$-$C_6$ alkynyl, fluorinated $C_1$-$C_6$ alkyl, fluorinated $C_2$-$C_6$ alkenyl, fluorinated $C_2$-$C_6$ alkynyl, hydroxyl, $C_1$-$C_6$ alkoxy, carboxyl, carboxyl-substituted $C_1$-$C_6$ alkyl, carboxyl-substituted $C_2$-$C_6$ alkenyl, carboxyl-substituted $C_2$-$C_6$ alkynyl, cyano, cyano-substituted $C_1$-$C_6$ alkyl, cyano-substituted $C_2$-$C_6$ alkenyl, cyano-substituted $C_2$-$C_6$ alkynyl, monocyclic aryl, bicyclic aryl, monocyclic heteroaryl, or bicyclic heteroaryl;

$R^2$ is selected from H, $C_1$-$C_3$ alkyl, carboxyl, and $C_2$-$C_6$ alkoxycarbonyl; and $R^3$ is $C_1$-$C_3$ alkyl.

In another embodiment, the invention provides a novel CBN analog having the structure of formula (II)

(II)

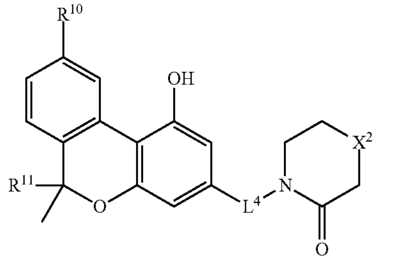

wherein:

$L^4$ is selected from $C_1$-$C_3$ alkylene, $C_2$-$C_3$ alkenylene, hydroxyl-substituted $C_1$-$C_3$ alkylene, hydroxyl-substituted $C_2$-$C_3$ alkenylene, fluorinated $C_1$-$C_3$ alkylene, fluorinated $C_2$-$C_3$ alkenylene, —O—, —(CO)—, —($SO_2$)—, —$NR^7$—, —$NR^7$—(CO)—, —(CO)—$NR^7$—, -and $NR^8$—(CO)—$NR^9$— wherein $R^7$, $R^8$, and $R^9$ are H or $C_1$-$C_3$ alkyl and $R^8$ and $R^9$ may be the same or different;

$R^{10}$ is selected from H, $C_1$-$C_3$ alkyl, carboxyl, and $C_2$-$C_6$ alkoxycarbonyl;

$R^{11}$ is $C_1$-$C_3$ alkyl; and $X^2$ is selected from O, $NR^{12}$, and $CR^{13}R^{14}$, wherein $R^{12}$ is $C_1$-$C_3$ alkyl or —(CO)—($C_1$-$C_3$ alkyl), and $R^{13}$ and $R^{14}$ are independently H or $C_1$-$C_3$ alkyl or are linked to form a $C_4$-$C_6$ alicyclic ring or a $C_2$-$C_5$ heteroalicyclic ring.

As explained infra in Section (I) of the Detailed Description, reference to a compound of the invention or to any molecular structure herein includes not only the specified molecular entity but also pharmaceutically acceptable, pharmacologically active analogs of the entity, such as salts, esters, amides, prodrugs, conjugates, active metabolites, hydrates, solvates, complexes, prodrugs, and other such derivatives, analogs, and related compounds.

The CBN analogs provided herein exhibit potent efficacy in treatment of pain and inflammation compared to NSAIDs and morphine. However, in contrast to CBN perse and $\Delta^9$-THC, the CBN analogs of the invention have little or no psychoactive activity. Without wishing to be bound by theory, it is proposed that the reason for this is that the preferred CBN analogs herein have different activity at the CB1 and CB2 receptors The CBN analogs of the invention are useful in numerous other methods as well, as will be detailed herein.

In another embodiment, the invention pertains to pharmaceutical formulations containing a therapeutically effective amount of at least one novel CBN analog as provided herein in combination with at least one pharmaceutically acceptable excipient. The formulations are generally "unit dosage" forms in which the therapeutically effective amount is suitable for a single dosage. The formulations may be immediate release or controlled release, and, if controlled release, are typically sustained release. The formulations may be prepared so as to be administered via any suitable route, e.g., oral, parenteral, transdermal, transmucosal (including intrarectal and intravaginal, via suppository), sublingual, by inhalation, via an implanted reservoir in a dosage form, and the like. For those compounds that are orally active, however, oral dosage forms are generally preferred, in which case the carrier is one that is suitable for oral ingestion. Oral formulations include solids, semi-solids, and liquids.

In an additional embodiment, pharmaceutical formulations are provided comprising a therapeutically effective amount of at least one CBN analog of the invention and at least one additional beneficial agent, which may or may not be a cannabinoid. Additional beneficial agents of interest include vitamins, minerals, amino acids, peptides, proteins, enzymes, co-enzymes, hormones, probiotics, fatty acids and other lipids, anti-oxidants, essential oils, fiber supplements, herbal supplements, botanicals, plant extracts, and pharmacologically active agents, e.g., anti-inflammatory and analgesic agents; it will be appreciated that any one compound may be encompassed by two or more of the foregoing categories.

The invention also provides a method for treating a condition, disease, or disorder in a mammalian subject by administering a therapeutically effective amount of a novel CBN analog of the invention or a pharmaceutical formulation comprising the CBN analog, wherein the "therapeutically effective amount" is an amount sufficient to treat the condition, disease, or disorder. Generally, the CBN analog is administered to a subject in a pharmaceutical formulation as described above, within the context of a predetermined dosing regimen.

In a related embodiment, the invention provides a method for treating a subject suffering from pain, endometriosis, primary dysmenorrhea, secondary premenstrual syndrome, uterine fibroid pain, menopausal symptoms, adenomyosis, polycystic ovary syndrome, alcoholism, anxiety, autism spectrum disorder, inflammatory bowel disease, celiac disease, systemic lupus erythematosus, Addison's disease, celiac disease, Graves' disease, Hashimoto thyroiditis, myasthenia gravis, psoriasis, Sjögren's disease, pernicious anemia, vasculitis, autoimmune hepatitis, and type 1 diabetes, burns, sarcomas, cardiac disorders, peripheral artery disease, cognitive pain, mild cognitive impairment, non-neurodegenerative dementia, multiple sclerosis, chronic inflammatory demyelinating polyneuropathy (CIDP), Guillain-Barré Syndrome, gingivitis, periodontitis, type 2 diabetes, glucose regulation, drug withdrawal, fibroses, acne, psoriasis, contact dermatitis, eczema, infectious skin ulcers, cellulitis, immunodeficiency, inflammation, ischemia, reduced fertility, limited fertility, fatty liver disease, cirrhosis, hepatitis, Metabolic Syndrome and any condition associated therewith, headaches, nausea, neurological disorders, neurodegenerative disorders, obesity, overweight, conditions caused by or associated with excess weight or obesity, osteoporosis, osteopenia, pelvic pain, attention deficit hyperactivity disorder (ADHD), bipolar disorder, depression, obsessive compulsive disorder (OCD), post-traumatic stress disorder (PTSD), psychosis, schizophrenia, respiratory disorders, seizure disorders, sleep apnea, insomnia, restless leg syndrome, REM sleep dysfunction, and stress.

Representative methods of particular interest include treatment of pain, regardless of origin, duration, or severity; treatment of women's health issues, e.g., endometriosis, dysmenorrhea, and the like; treatment of inflammatory arthritic disorders, inflammatory gastrointestinal disorders, and other disorders associated with or caused by inflammation; and a method for inducing weight loss in a subject and treating conditions caused by or otherwise associated with overweight or obesity.

In a further embodiment of the invention, an opioid-sparing method is provided, i.e., a method for reducing the dose of an opioid needed to manage pain in a subject.

Administration of opioid analgesics to control pain, as is well known, has significant risks, including addiction, overdose, and various unwanted side effects. In this embodiment, the invention provides an improved method to treat pain in a subject that offsets the aforementioned risks. The method comprises co-administering to a subject already receiving a therapeutically effective analgesic dose of an opioid, typically within a monotherapeutic dosage regimen, an opioid sparing dose of a CBN analog of the invention, thereby enabling a reduction in the therapeutically effective analgesic dose of the opioid.

In another embodiment, a method of opioid sparing in a subject in need of pain management is provided, where the method comprises co-administering to the subject an effective opioid-sparing dose of a CBN analog of the invention and an opioid analgesic.

In another embodiment, a method is provided for managing weight loss in a subject, wherein the method comprises co-administering to the subject a CBN analog of the invention and a glucagon-like peptide 1 receptor agonist (GLP-1 RA). In one embodiment, the method comprises administering a CBN analog to the subject at the beginning of an ongoing dosage regimen and co-administering the GLP-1 RA at a later point in the dosage regimen, wherein the GLP-1 RA is administered in an amount within or below the approved dosage range for the selected GLP-1RA. The method for managing weight loss extends to treatment of type 2 diabetes, Metabolic Syndrome, and other conditions, disorders, and diseases caused by or otherwise associated with obesity and excess weight.

DETAILED DESCRIPTION OF THE INVENTION

I. Definitions and Nomenclature

Figure 1:
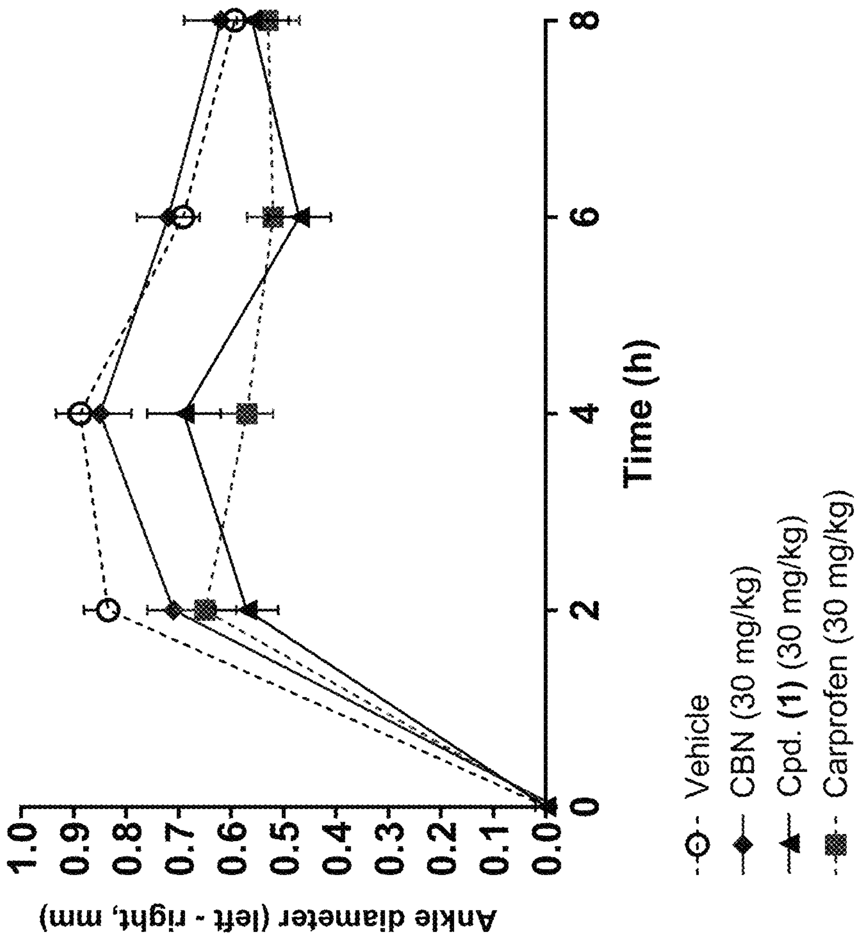
FIG. 1 is a graph indicating the efficacy of CBN analog (1) in reducing carageenan-induced inflammation in mice and provides a comparison with carprofen and cannabinol, evaluated as described in Example 8.
Figure 2:
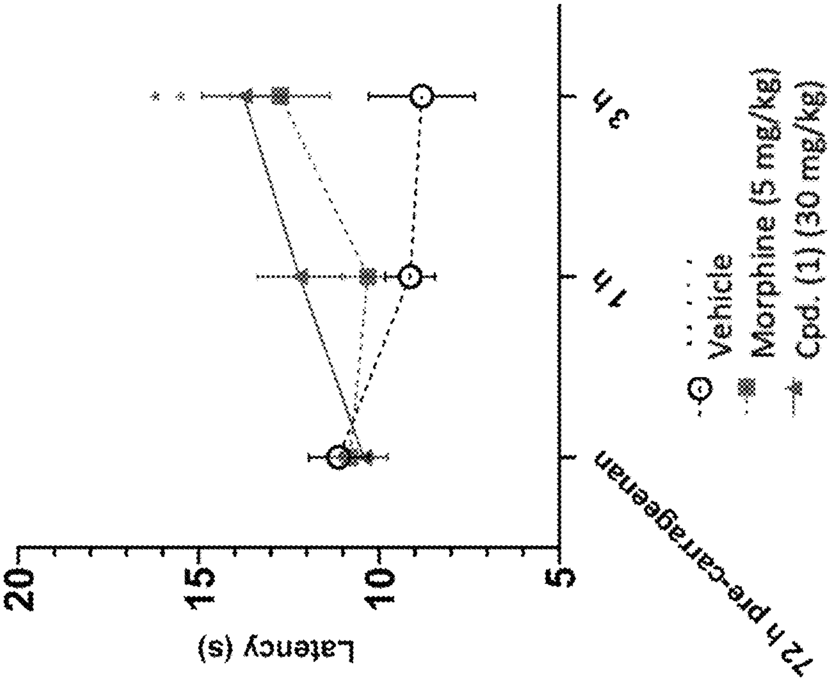
FIG. 2 is a graph indicating the efficacy of CBN analog (1) in reducing thermally induced pain in mice using the Hargreaves test and provides a comparison with morphine, as also evaluated according to the description in Example 8.
Figure 3:
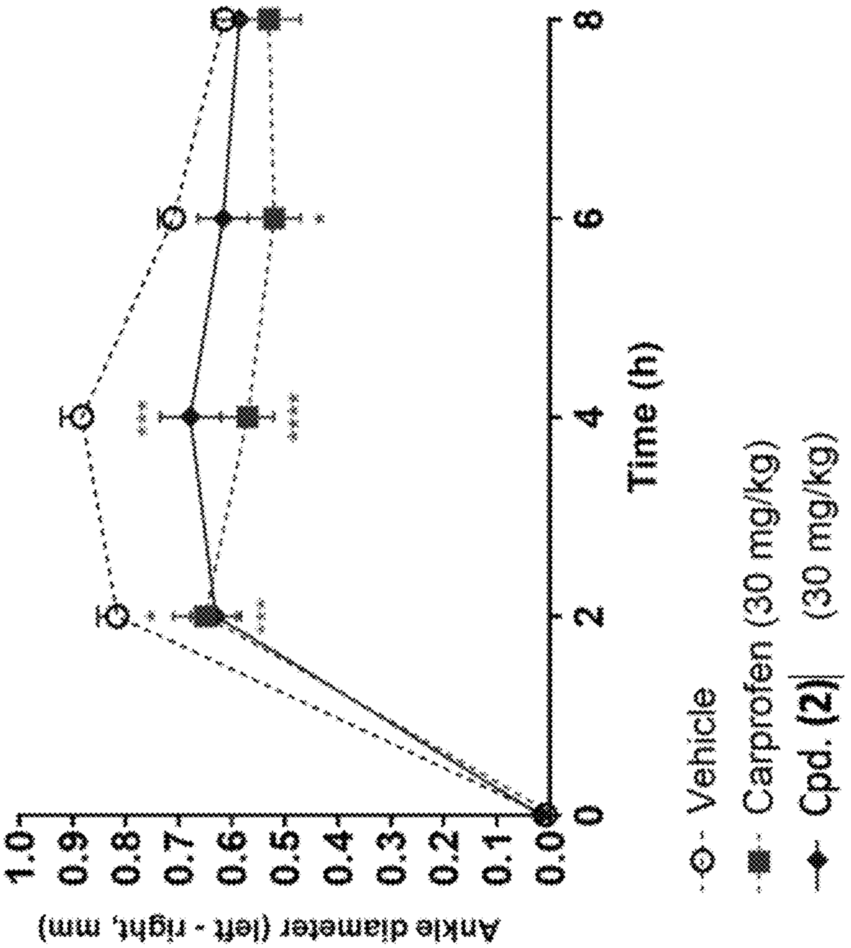
FIG. 3 is a graph indicating the efficacy of CBN analog (2) in reducing carageenan-induced inflammation in mice and provides a comparison with carprofen, as also evaluated according to the description in Example 8.
Figure 4:
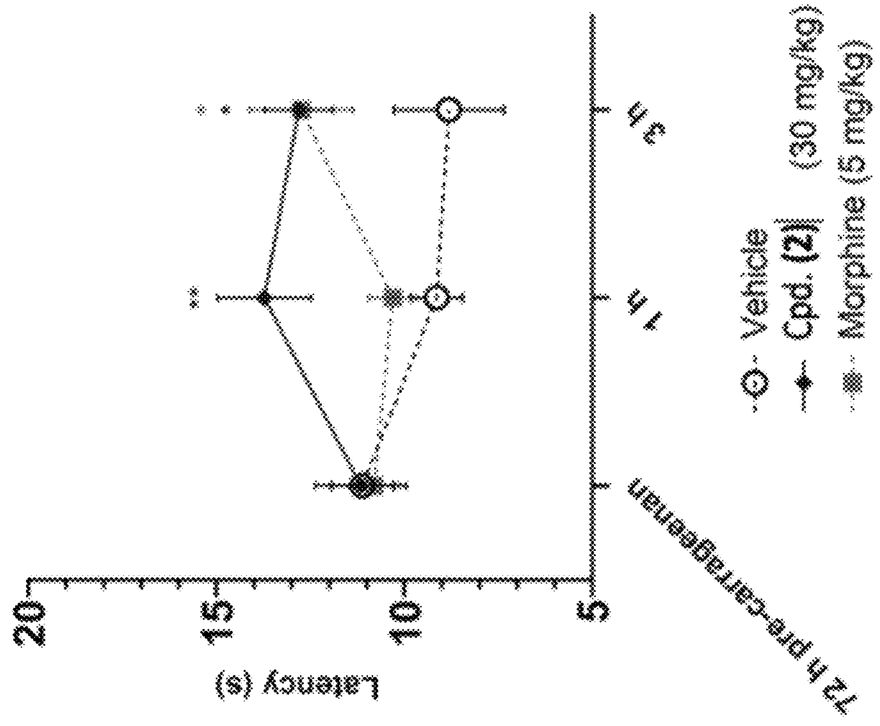
FIG. 4 is a graph indicating the efficacy of CBN analog (2) in reducing thermally induced pain in mice using the Hargreaves test and provides a comparison with morphine, as also evaluated according to the description in Example 8.
Figure 5:
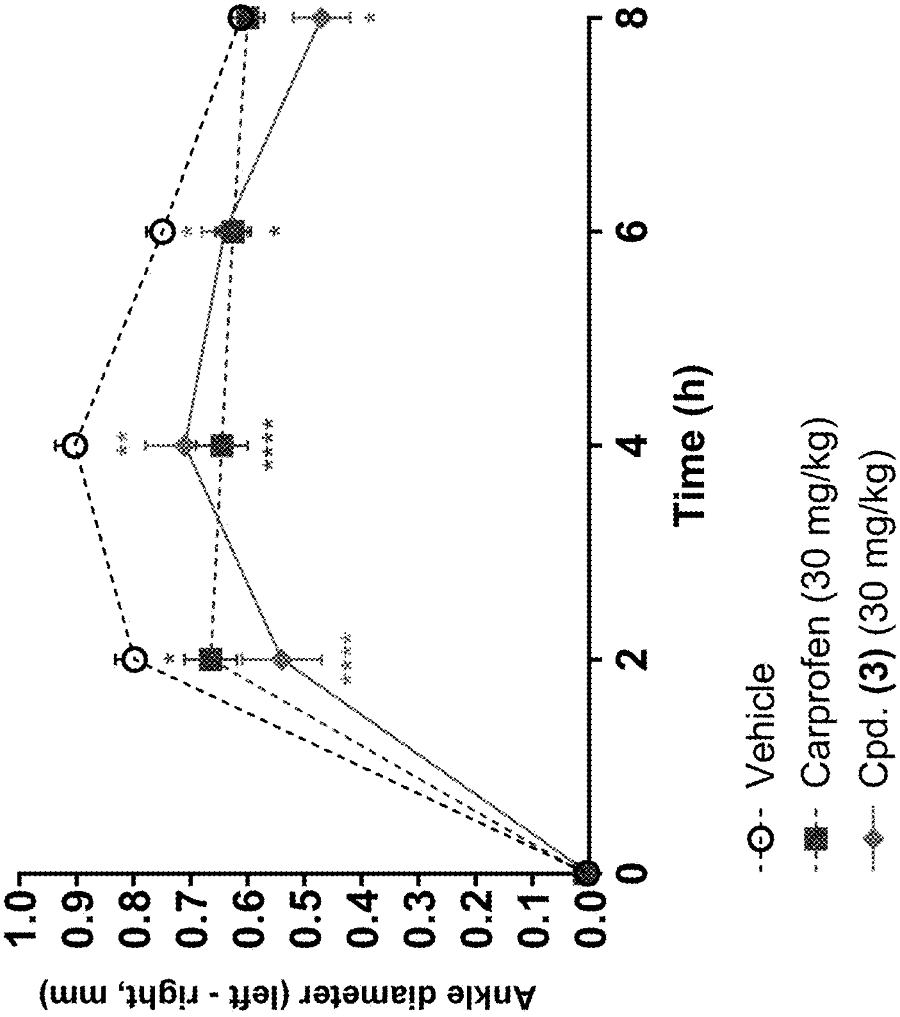
FIG. 5 is a graph indicating the efficacy of CBN analog (3) in reducing carageenan-induced inflammation in mice and provides a comparison with carprofen, as also evaluated according to the description in Example 8.
Figure 6:
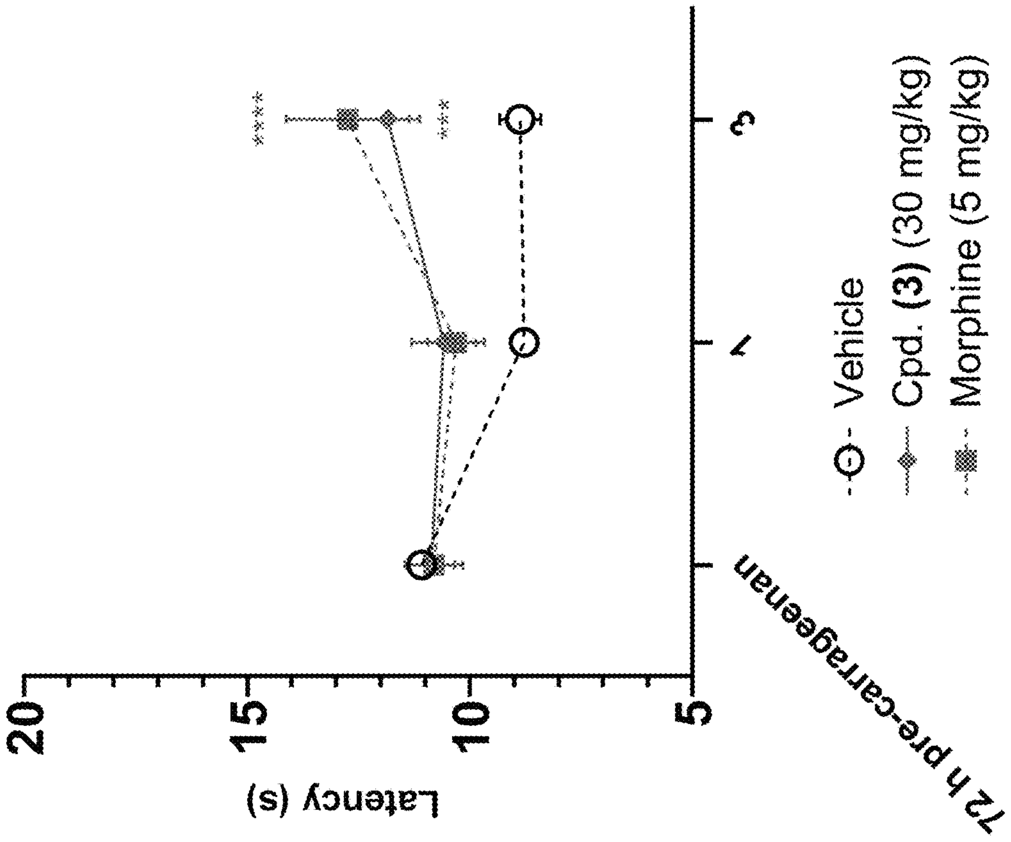
FIG. 6 is a graph indicating the efficacy of CBN analog (3) in reducing thermally induced pain in mice using the Hargreaves test and provides a comparison with morphine, as also evaluated according to the description in Example 8.

Unless defined otherwise, all technical and scientific terms used herein have the meaning commonly understood by one of ordinary skill in the art to which the invention pertains. It is also to be understood that the terminology used herein is for the purpose of describing particular embodiments only and is not intended to be limiting. Specific terminology of particular importance to the description of the present invention is defined below.

In this specification and the appended claims, the singular forms “a,” “an” and “the” include plural referents unless the context clearly dictates otherwise. Thus, for example, reference to “a substituent” includes a single substituent as well as two or more substituents that may be the same or different, reference to “a compound” encompasses a combination or mixture of different compounds as well as a single compound, reference to “a pharmaceutically acceptable excipient” includes two or more excipients as well as a single carrier or excipient, and the like.

As used herein, the phrase “having the formula” or “having the structure” is not intended to be limiting and is used in the same way that the term “comprising” is used. In addition, unless otherwise indicated, the invention is not limited to specific synthetic methods, analogs, substituents, pharmaceutical formulations, formulation components, modes of administration, or the like, as such may vary.

The term “alkyl” as used herein refers to a branched or unbranched saturated hydrocarbon group typically although not necessarily containing 1 to about 18 carbon atoms, such as methyl, ethyl, n-propyl, isopropyl, n-butyl, isobutyl, t-butyl, octyl, decyl, and the like, as well as cycloalkyl groups such as cyclobutyl, cyclopentyl, cyclohexyl, and the like. Generally, although again not necessarily, alkyl groups herein contain 1 to 12 carbon atoms, e.g., 1 to 12 carbon atoms, 1 to 10 carbon atoms, 1 to 8 carbon atoms, 1 to 6 carbon atoms or 1 to 3 carbon atoms. Typically, alkyl groups herein contain 1 to 6 carbon atoms or 1 to 3 carbon atoms. “Substituted alkyl” refers to alkyl substituted with one or more substituent groups, and the terms “heteroatom-containing alkyl” and “heteroalkyl” refer to alkyl in which at least one carbon atom is replaced with a heteroatom, as described in further detail infra. If not otherwise indicated, the term “alkyl” includes linear, branched, cyclic, unsubstituted, substituted, and/or heteroatom-containing alkyl.

The term “alkylene” refers to a bivalent saturated aliphatic group containing 1 to about 12 carbon atoms, and preferably containing 1 to 6 carbon atoms. Unless otherwise indicated, the term “alkylene” includes substituted alkylene and/or heteroatom-containing alkylene.

The term “aryl” as used herein refers to an aromatic substituent containing one to three aromatic rings, either fused or linked, and either unsubstituted or substituted with one or more substituents. Unless otherwise indicated, the term “aryl” includes substituted aryl and/or heteroatom-containing aryl. Typically, aryl groups herein contain about 5 to about 20 carbon atoms, and thus include, by way of example, phenyl, naphthyl, and the like.

The term "alkenyl" as used herein refers to a linear, branched or cyclic hydrocarbon group of 2 to about 24 carbon atoms containing at least one double bond, such as ethenyl, n-propenyl, isopropenyl, n-butenyl, isobutenyl, octenyl, decenyl, tetradecenyl, hexadecenyl, eicosenyl, tetracosenyl, and the like. Generally, although again not necessarily, alkenyl groups herein contain 2 to about 18 carbon atoms, 2 to 12 carbon atoms, most typically 2 to 6 carbon atoms. The term "substituted alkenyl" refers to alkenyl substituted with one or more substituent groups, and the terms "heteroatom-containing alkenyl" and "heteroalkenyl" refer to alkenyl in which at least one carbon atom is replaced with a heteroatom. If not otherwise indicated, the terms "alkenyl" and "lower alkenyl" include linear, branched, cyclic, unsubstituted, substituted, and/or heteroatom-containing alkenyl and lower alkenyl, respectively.

The term "alkynyl" as used herein refers to a linear or branched hydrocarbon group of 2 to 24 carbon atoms containing at least one triple bond, such as ethynyl, n-propynyl, and the like. Generally, although again not necessarily, alkynyl groups herein contain 2 to 4 carbon atoms, preferably 2 or 3 carbon atoms. The term "substituted alkynyl" refers to alkynyl substituted with one or more substituent groups, and the terms "heteroatom-containing alkynyl" and "heteroalkynyl" refer to alkynyl in which at least one carbon atom is replaced with a heteroatom. If not otherwise indicated, the terms "alkynyl" and "lower alkynyl" include linear, branched, unsubstituted, substituted, and/or heteroatom-containing alkynyl and lower alkynyl, respectively.

The term "alkoxy" as used herein intends an alkyl group bound through a single, terminal ether linkage; that is, an "alkoxy" group may be represented as —O-alkyl where alkyl is as defined above. Generally, however, the alkoxy groups herein contain 1-6 carbon atoms or 1 to 3 carbon atoms, and therefore include, for example, methoxy, ethoxy, n-propoxy, isopropoxy, t-butyloxy, etc. Preferred lower alkoxy substituents contain 1 to 3 carbon atoms, and particularly preferred such substituents contain 1 or 2 carbon atoms (i.e., methoxy and ethoxy). The terms "alkenyloxy" and "alkynyloxy" are defined in an analogous manner.

The term "aryl" as used herein, and unless otherwise specified, refers to an aromatic substituent containing a single aromatic ring or multiple aromatic rings that are fused together, directly linked, or indirectly linked (such that the different aromatic rings are bound to a common group such as a methylene or ethylene moiety). Preferred aryl groups contain 5 to 24 carbon atoms, and particularly preferred aryl groups contain 5 to 14 carbon atoms. Exemplary aryl groups contain one aromatic ring or two fused or linked aromatic rings, e.g., phenyl, naphthyl, biphenyl, diphenylether, diphenylamine, benzophenone, and the like. Typical aryl groups herein are monocyclic 5-membered and 6-membered rings, e.g., substituted or unsubstituted phenyl or cyclopentyl. "Substituted aryl" refers to an aryl moiety substituted with one or more substituent groups, and the terms "heteroatom-containing aryl" and "heteroaryl" refer to aryl substituent, in which at least one carbon atom is replaced with a heteroatom, as will be described in further detail infra. If not otherwise indicated, the term "aryl" includes unsubstituted, substituted, and/or heteroatom-containing aromatic substituents.

The term "cyclic" refers to alicyclic or aromatic substituents that may or may not be substituted and/or heteroatom containing, and that may be monocyclic, bicyclic, or polycyclic.

The term "alicyclic" is used in the conventional sense to refer to an aliphatic cyclic moiety, as opposed to an aromatic cyclic moiety, and may be monocyclic, bicyclic, or polycyclic, and, if bicyclic or polycyclic, may be bridged, linked, or fused.

The terms "halo" and "halogen" are used in the conventional sense to refer to a chloro, bromo, fluoro, or iodo substituent.

The term "heteroatom-containing" as in a "heteroatom-containing alkyl group" (also termed a "heteroalkyl" group) or a "heteroatom-containing aryl group" (also termed a "heteroaryl" group) refers to a molecule, linkage, or substituent in which one or more carbon atoms are replaced with an atom other than carbon, e.g., nitrogen, oxygen, sulfur, phosphorus, or silicon, typically nitrogen, oxygen, or sulfur, preferably nitrogen or oxygen. Similarly, the term "heteroalkyl" refers to an alkyl substituent that is heteroatom-containing, the term "heterocyclic" refers to a cyclic substituent that is heteroatom-containing, the terms "heteroaryl" and heteroaromatic" respectively refer to "aryl" and "aromatic" substituents that are heteroatom-containing, and the like. Examples of heteroalkyl groups include alkoxyaryl, alkylsulfanyl-substituted alkyl, N-alkylated amino alkyl, and the like. Examples of heteroaryl substituents include pyrrolyl, pyrrolidinyl, pyridinyl, quinolinyl, indolyl, pyrimidinyl, imidazolyl, 1,2,4-triazolyl, tetrazolyl, etc., and examples of heteroatom-containing alicyclic groups are pyrrolidino, morpholino, piperazino, piperidino, etc.

By "substituted" as in "substituted alkyl," "substituted aryl," and the like, as alluded to in some.of the aforementioned definitions, is meant that in the alkyl, aryl, or other moiety, at least one hydrogen atom bound to a carbon (or other) atom is replaced with one or more non-hydrogen substituents. Examples of such substituents include functional groups and hydrocarbyl moieties.

Functional groups that may represent substituents in the substituted molecular structures and segments thereof include, without limitation: halo, hydroxyl, sulfhydryl, $C_1$-$C_{18}$ alkoxy, $C_2$-$C_{18}$ alkoxyalkyl, $C_2$-$C_{18}$ alkenyloxy, $C_2$-$C_{18}$ alkynyloxy, $C_5$-$C_{18}$ aryloxy, acyl (including $C_2$-$C_{18}$ alkylcarbonyl (—CO-alkyl) and $C_6$-$C_{18}$ arylcarbonyl (—CO-aryl)), acyloxy (—O-acyl), $C_2$-$C_{18}$ alkoxycarbonyl (—(CO)—O-alkyl), $C_6$-$C_{18}$ aryloxycarbonyl (—(CO)—O-aryl), halocarbonyl (—CO)—X where X is halo), $C_2$-$C_{18}$ alkylcarbonato (—O—(CO)—O-alkyl), $C_6$-$C_{18}$ arylcarbonato (—O—(CO)—O-aryl), carboxyl (—COOH), carboxylato (—COO—), carbamoyl (—(CO)—$NH_2$), mono-($C_1$-$C_{18}$ alkyl)-substituted carbamoyl (—(CO)—NH($C_1$-$C_{18}$ alkyl)), di-($C_1$-$C_{18}$ alkyl)-substituted carbamoyl (—(CO)—N($C_1$-$C_{18}$ alkyl$)_2$), mono-($C_5$-$C_{18}$ aryl)-substituted carbamoyl (—(CO)—NH-aryl), di-($C_5$-$C_{18}$ aryl)-substituted carbamoyl (—(CO)—N(aryl$)_2$), di-N—($C_1$-$C_{18}$ alkyl), N—($C_5$-$C_{18}$ aryl)-substituted carbamoyl, thiocarbamoyl (—(CS)—$NH_2$), carbamido (—NH—(CO)—$NH_2$), cyano (—C≡N), isocyano (—$N^+$≡$C^-$), cyanato (—O—C≡N), isocyanato (—O—$N^+$≡$C^-$), isothiocyanato (—S—C≡N), azido (—N═$N^+$≡$N^-$), formyl (—(CO)—H), thioformyl (—(CS)—H), amino (—$NH_2$), mono-($C_1$-$C_{18}$ alkyl)-substituted amino, di-($C_1$-$C_{18}$ alkyl)-substituted amino, mono-($C_5$-$C_{18}$ aryl)-substituted amino, di-($C_5$-$C_{18}$ aryl)-substituted amino, $C_2$-$C_{18}$ alkylamido (—NH—(CO)-alkyl), $C_6$-$C_{18}$ arylamido (—NH—(CO)-aryl), imino (—CR═NH where R=hydrogen, $C_1$-$C_{18}$ alkyl, $C_5$-$C_{18}$ aryl, $C_6$-$C_{18}$ alkaryl, $C_6$-$C_{18}$ aralkyl, etc.), alkylimino (—CR═N(alkyl), where R=hydrogen, $C_1$-$C_{18}$ alkyl, $C_5$-$C_{18}$ aryl, $C_6$-$C_{18}$ alkaryl, $C_6$-$C_{18}$ aralkyl, etc.), arylimino (—CR═N(aryl), where R=hydrogen, $C_1$-$C_{18}$ alkyl, $C_5$-$C_{18}$ aryl, $C_6$-$C_{18}$ alkaryl, $C_6$-$C_{18}$ aralkyl, etc.), nitro (—$NO_2$), nitroso (—NO), sulfo (—$SO_2$—OH), sulfonato (—$SO_2$—O—), $C_1$-$C_{18}$ alkylsulfanyl (—S-alkyl; also termed "alkylthio"), arylsulfanyl (—S-aryl; also termed "arylthio"), $C_1$-$C_{18}$ alkylsulfinyl (—(SO)-alkyl), $C_5$-$C_{18}$ arylsulfinyl (—(SO)-aryl), $C_1$-$C_{18}$ alkylsulfonyl (—$SO_2$-alkyl), $C_5$-$C_{18}$ arylsulfonyl (—$SO_2$-aryl), phosphono (—P(O)$(OH)_2$), phosphonato (—P(O)$(O—)_2$), phosphinato (—P(O)(O—)), phospho (—$PO_2$), and phosphino (—$PH_2$).

The aforementioned functional groups may, if a particular group permits, be further substituted with one or more additional functional groups or with one or more hydrocarbyl moieties such as those specifically enumerated above, and the term "functional group" encompasses all such instances.

When the term "substituted" appears prior to a list of possible substituted groups, it is intended that the term apply to every member of that group. For example, the phrase "substituted alkyl, alkenyl, and aryl" is to be interpreted as "substituted alkyl, substituted alkenyl, and substituted aryl." Analogously, when the term "heteroatom-containing" appears prior to a list of possible heteroatom-containing groups, it is intended that the term apply to every member of that group. For example, the phrase "heteroatom-containing alkyl, alkenyl, and aryl" is to be interpreted as "heteroatom-containing alkyl, substituted alkenyl, and substituted aryl."

The term "protected" to refer to a functional group means that the group is in modified form to preclude undesired side reactions at the protected site. Suitable protecting groups for the compounds of the present invention will be recognized from this description taking into account the level of skill in the art, and with reference to standard textbooks, such as Greene et al., Protective Groups in Organic Synthesis (New York: Wiley, 1991). A "protected" compound refers to a compound in which one or more functional groups are protected.

"Optional" or "optionally" means that the subsequently described circumstance may or may not occur, so that the description includes instances where the circumstance occurs and instances where it does not. For example, the phrase "optionally substituted" means that a non-hydrogen substituent may or may not be present on a given atom, and, thus, the description includes structures wherein a non-hydrogen substituent is present and structures wherein a non-hydrogen substituent is not present.

The terms "active agent," "drug" and "pharmacologically active agent" are used interchangeably herein to refer to a chemical compound that, when administered to an organism (human or animal) induces a desired pharmacological effect. Included are derivatives and analogs of those compounds or classes of compounds that also induce the desired effect. When referring to a CBN analog of the invention as an active agent, then, it is intended that the CBN analog encompass not only the specified molecular entity but also its pharmaceutically acceptable, pharmacologically active analogs, including, but not limited to, salts, esters, amides, prodrugs, conjugates, active metabolites, racemic mixtures, hydrates, solvates, complexes, prodrugs, and other such derivatives, analogs, and related compounds.

The terms "treating" and "treatment" as used herein refer to reduction in severity and/or frequency of symptoms, elimination of symptoms and/or underlying cause, prevention of the occurrence of symptoms and/or their underlying cause, and improvement or remediation of damage. Thus, "treating" a subject or patient with a compound of the invention includes prevention of a particular disorder or adverse physiological event in a susceptible individual as well as treatment of a clinically symptomatic individual by inhibiting or causing regression of a disorder or disease. The terms "condition," "disorder," and "disease" are used interchangeably herein as adverse physiological states that are treatable with the CBN analogs of the invention.

The terms "subject" and "patient" are used interchangeably herein to refer to the individual to whom the CBN analog of the invention is administered, and while usually indicating a human individual, the terms may also refer to a non-human mammal.

By the terms "effective amount" and "therapeutically effective amount" of a CBN analog of the invention is meant a nontoxic but sufficient amount of the compound to provide the desired effect in a particular context, depending, for instance, on the indication being addressed, the mode of administration, the medical history of the subject to whom the compound is administered, the subject's weight, age, and general health, as well as the judgment of the prescribing physician. Examples of suitable ranges for the therapeutically effective amount are provided in Section IV of this Detailed Description.

The term "dosage form" denotes any form of a pharmaceutical formulation that contains a therapeutically effective amount of the active agent.

"Carriers" or "vehicles" as used herein refer to subsets of the general class of pharmaceutically acceptable excipients. Carriers and vehicles useful herein include any such materials known in the art, e.g., any liquid, gel, solvent, liquid diluent, solubilizer, or the like, which is nontoxic and does not interact with other components of the formulation in a deleterious manner.

The term "controlled release" refers to a drug-containing formulation or fraction thereof in which release of the drug is not immediate, i.e., with a "controlled release" formulation, administration does not result in immediate release of the drug into an absorption pool. The term is used interchangeably with "nonimmediate release" as defined in Remington: The Science and Practice of Pharmacy, Nineteenth Ed. (Easton, Pa.: Mack Publishing Company, 1995). In general, the term "controlled release" as used herein includes sustained release and delayed release formulations.

(66) The term "sustained release" (synonymous with "extended release") is used in its conventional sense to refer to a drug formulation that provides for gradual release of a drug over an extended period of time, and that preferably, although not necessarily, results in substantially constant blood levels of a drug over an extended time period.

(67) By "pharmaceutically acceptable" is meant a material that is not biologically or otherwise undesirable, i.e., the material may be incorporated into a pharmaceutical formulation administered to a subject without causing any undesirable biological effects or interacting in a deleterious manner with any of the other components of the formulation in which it is contained. When the term "pharmaceutically acceptable" is used to refer to a pharmaceutical carrier or excipient, it is implied that the carrier or excipient has met the required standards of toxicological and manufacturing testing or that it is included on the Inactive Ingredient Guide prepared by the U.S. Food and Drug Administration and/or designated GRAS ("Generally Recognized as Safe").

The numbering system typically applied to cannabinol as well as to analogous compounds and employed herein is shown in the following structure:

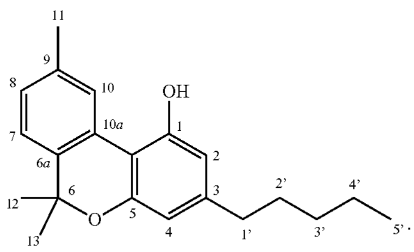

II. The Novel CBNAnalogs

In one embodiment, a CBN analog is provided as a novel compound having the structure of formula (I)

(I)

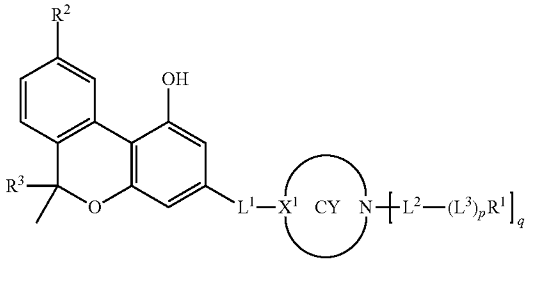

wherein $L^1$, $L^2$, $L^3$, p, $X^1$, CY, $R^1$, $R^2$, $R^3$, and q are as follows:

$L^1$ is selected from $C_1$-$C_3$ alkylene, $C_1$-$C_3$ alkenylene, hydroxyl-substituted $C_1$-$C_3$ alkylene, hydroxyl-substituted $C_1$-$C_3$ alkenylene, fluorinated $C_1$-$C_3$ alkylene, fluorinated $C_2$-$C_3$ alkenylene, —O—, —(CO)—, —($SO_2$)—, —$NR^4$—, —$NR^4$—(CO)—, —(CO)—$NR^4$—, -and $NR^5$—(CO)—$NR^6$— wherein $R^4$, $R^5$, and $R^6$ are H or $C_1$-$C_3$ alkyl and $R^5$ and $R^6$ may be the same or different.

In some embodiments, $L^1$ is selected from —$CH_2$—, —CH(OH)—, —$CF_2$—, —CHF—, —O—, —($SO_2$)—, —(CO)—, —($SO_2$)—, —NH—, —NH—(CO)—, —(CO)—NH—, and —NH—(CO)—NH—.

The linker $L^2$ connecting the terminal nitrogen atom of CY with $R^1$ through the optional additional linker -$(L^3)_p$ is selected from —(CO)— and —($SO_2$)—.

$L^3$ is selected from —CH—, —NH—CH—, and —$CH_2$—N—, and p is zero or 1, such that $L^3$ may be absent or present in the molecular structure.

CY comprises a monocyclic or bicyclic group comprising 4-10 ring atoms and zero to 4 nonhydrogen substituents, any two of which may be linked to form a bridged bicyclic moiety, wherein CY is aliphatic or aromatic and further comprises zero to 3 additional heteroatoms, i.e., zero 3 heteroatoms in addition to the ring nitrogen atom in the structure of formula (I).

$X^1$ is selected from N, C, and CH, wherein when CY is aromatic, $X^1$ is N or C. Generally, although not necessarily, $X^1$ is N or CH.

In some embodiments, CY comprises azetidinyl, diazetidinyl, pyrrolidinyl, imidazolidinyl, pyrazolidinyl, piperidinyl, piperazinyl, pyrrolyl, imidazolyl, pyrazolyl, 1,2,3-triazolyl, 1,2,4-triazolyl, 1,3,4-triazolyl, tetrazolyl, pyridinyl, pyridazinyl, pyrimidinyl, pyrazinyl, aza-bicyclo[4.1.1]octanyl, or other such nitrogen heterocycle substituents. It is to be understood when CY is, for example, piperidinyl—in which case $X^1$ is CH and CY is a saturated six-membered ring—that both $X^1$ and the ring nitrogen atom shown in formula (I) are ring atoms within CY, i.e., $X^1$ and the ring nitrogen atom are contained within the piperidinyl ring. As another example, when CY is imidazolyl—in which case $X^1$ is N and CY is an aromatic 5-membered ring—both nitrogen atoms are ring atoms within CY, i.e., within the imidazolyl ring. With respect to a bicyclic CY group, such as aza-bicyclo[4.1.1]octanyl as alluded to above, it is to be understood that CY in that case essentially has two substituents that are linked to form a bridged bicyclic compound. Such bicyclic structures are within the scope of the present invention.

$R^1$ comprises $C_1$-$C_6$ alkyl, $C_2$-$C_6$ alkenyl, $C_2$-$C_6$ alkynyl, fluorinated $C_1$-$C_6$ alkyl, fluorinated $C_2$-$C_6$ alkenyl, fluorinated $C_2$-$C_6$ alkynyl, hydroxyl, $C_1$-$C_6$ alkoxy, carboxyl, carboxyl-substituted $C_1$-$C_6$ alkyl, carboxyl-substituted $C_2$-$C_6$ alkenyl, carboxyl-substituted $C_2$-$C_6$ alkynyl, cyano, cyano-substituted $C_1$-$C_6$ alkyl, cyano-substituted $C_2$-$C_6$ alkenyl, cyano-substituted $C_2$-$C_6$ alkynyl, monocyclic aryl, bicyclic aryl, monocyclic heteroaryl, or bicyclic heteroaryl.

In some embodiments, $R^1$ is selected from $C_1$-$C_6$ alkyl, fluorinated $C_1$-$C_6$ alkyl, $C_2$-$C_6$ alkenyl, fluorinated $C_2$-$C_6$ alkenyl, hydroxyl, carboxyl, cyano, and monocyclic aryl or heteroaryl (e.g., phenyl, imidazolyl, triazolyl, or the like).

In some embodiments, $R^1$ is selected from $C_1$-$C_3$ alkyl, fluorinated $C_1$-$C_3$ alkyl, $C_2$-$C_3$ alkenyl, fluorinated $C_2$-$C_3$ alkenyl, and cyano. When $R^1$ is a fluorinated $C_1$-$C_3$ alkyl substituent or a fluorinated $C_2$-$C_3$ alkenyl substituent, the substituent may or may not be perfluorinated. Fluorinated $C_1$-$C_3$ alkyl substituents thus include —$CF_3$, —$CF_2H$, —$CF_2$—$CH_3$, —$CH_2$—$CF_3$, —$CH_2$—$CF_2H$, —CHF—$CF_3$, —CHF—$CF_2H$, —$CF_2$—$CF_3$, —$CF_2$—$CF_2H$, —$CH_2CH_2$—$CF_3$, —$CH_2CH_2$—$CF_2H$, and —$CF_2CF_2CF_3$, while fluorinated $C_2$-$C_3$ alkenyl substituents include —CH═CHF, —CH═$CF_2$, —CF═$CH_2$, —CF═$CF_2$, —$CH_2$—CH═CHF, —$CH_2$—CH═$CF_2$, —$CH_2$—CF═$CH_2$, —$CH_2$—CF═$CF_2$, —$CF_2$—CH═CHF, —$CF_2$—CH═$CF_2$, —$CF_2$—CF═$CH_2$, —$CF_2$—CF═$CF_2$, —CHF—CH═CHF, —CHF—CH═$CF_2$, —CHF—CF═$CH_2$, and —CHF—CF═$CF_2$.

$R^2$ is selected from H, $C_1$-$C_3$ alkyl, carboxyl, and $C_2$-$C_6$ alkoxycarbonyl. In some embodiments, $R^2$ is H, $C_1$-$C_3$ alkyl, or carboxyl, e.g., H or $C_1$-$C_3$ alkyl, typically methyl.

$R^3$ is $C_1$-$C_3$ alkyl, typically methyl.

When q is zero, the molecular structure of formula (I) terminates in CY; for instance, CY may represent a terminal group of the molecule when CY is azole, a diazole such as imidazole or pyrazole, or a triazole, including 1, 2, 3-triazole, 1,2,4-triazole, and 1,3,4-triazole. In these instances, the nitrogen atom shown within CY in the molecular structure of Formula (I) represents a ring nitrogen atom within N-heterocycle.

Table 1, below, sets forth representative CBN analogs of the invention having the structure of formula (I) with reference to $L^1$, $X^1$, CY, $L^2$, $L^3$, p, $R^1$, $R^2$, $R^3$, and q:

TABLE 1

| Cpd. | $L^1$ | $X^1$ | CY | $L^2$ | $L^3$ | p | $R^1$ | $R^2$ | $R^3$ | q |
|---|---|---|---|---|---|---|---|---|---|---|
| (1) | —$CH_2$— | CH | piperidinyl | —(CO)— | — | 0 | —$CF_2H$ | —$CH_3$ | —$CH_3$ | 1 |
| (2) | —$CH_2$— | CH | piperidinyl | —(CO)— | — | 0 | —$CH_3$ | —$CH_3$ | —$CH_3$ | 1 |
| (4) | —(CO)— | N | piperazinyl | —(CO)— | — | 0 | —$CF_2H$ | —$CH_3$ | —$CH_3$ | 1 |
| (5) | —$CH_2$— | N | piperazinyl | —(CO)— | — | 0 | —$CF_2H$ | —$CH_3$ | —$CH_3$ | 1 |
| (6) | —NH— | CH | piperidinyl | —(CO)— | — | 0 | —$CF_2H$ | —$CH_3$ | —$CH_3$ | 1 |
| (7) | —$CH_2$— | CH | piperidinyl | —(CO)— | —$NHCH_2$— | 1 | —$CF_2H$ | —$CH_3$ | —$CH_3$ | 1 |
| (8) | —NH— | CH | piperidinyl | —(CO)— | —$NHCH_2$— | 1 | —$CF_2H$ | —$CH_3$ | —$CH_3$ | 1 |
| (9) | —NH—(CO)— | CH | piperidinyl | —(CO)— | — | 0 | —$CF_2H$ | —$CH_3$ | —$CH_3$ | 1 |
| (10) | —$CH_2$— | CH | azetidinyl | —(CO)— | — | 0 | —$CF_2H$ | —$CH_3$ | —$CH_3$ | 1 |
| (11) | —$CH_2$— | CH | azetidinyl | —(CO)— | —$NHCH_2$— | 1 | —$CF_2H$ | —$CH_3$ | —$CH_3$ | 1 |
| (12) | —$CH_2$— | CH | piperidinyl | —(CO)— | — | 0 | —$CF_2H$ | —COOH | —$CH_3$ | 1 |
| (13) | —$CH_2$— | CH | aza-bicyclo [4.1.1]octanyl | —(CO)— | — | 0 | —$CF_2H$ | —$CH_3$ | —$CH_3$ | 1 |
| (14) | —$CH_2$— | CH | piperidinyl | —($SO_2$)— | — | 0 | —$CF_2H$ | —$CH_3$ | —$CH_3$ | 1 |
| (15) | —$CH_2$— | CH | piperidinyl | —($SO_2$)— | $CH_2$— | 1 | —$CF_2H$ | —$CH_3$ | —$CH_3$ | 1 |
| (16) | —($SO_2$)— | N | piperazinyl | —(CO)— | — | 0 | —$CF_2H$ | —$CH_3$ | —$CH_3$ | 1 |
| (17) | —O— | CH | piperidinyl | —(CO)— | — | 0 | —$CF_2H$ | —$CH_3$ | —$CH_3$ | 1 |
| (18) | —$CH_2$ | CH | pyrrolidinyl | —(CO)— | — | 0 | —$CF_2H$ | —$CH_3$ | —$CH_3$ | 1 |
| (19) | —$CH_2$— | CH | piperidinyl | —(CO)— | — | 0 | —CH═$CH_2$ | —$CH_3$ | —$CH_3$ | 1 |
| (20) | —O— | CH | piperidinyl | —($SO_2$)— | —$CH_2$— | 1 | —$CF_2H$ | —$CH_3$ | —$CH_3$ | 1 |
| (21) | —NH—(CO)— | CH | piperidinyl | —($SO_2$)— | —$CH_2$— | 1 | —$CF_2H$ | —$CH_3$ | —$CH_3$ | 1 |
| (22) | —NH—(CO)—NH— | CH | piperidinyl | —($SO_2$)— | —$CH_2$— | 1 | —$CF_2H$ | —$CH_3$ | —$CH_3$ | 1 |
| (23) | —$CH_2$— | C | pyrrolyl | —(CO)— | — | 0 | —$CF_2H$ | —$CH_3$ | —$CH_3$ | 1 |
| (24) | —$CH_2$— | C | imidazolyl | —(CO)— | — | 0 | —$CF_2H$ | —$CH_3$ | —$CH_3$ | 1 |
| (25) | —CH(OH)— | CH | piperidinyl | —(CO)— | — | 0 | —$CF_2H$ | —$CH_3$ | —$CH_3$ | 1 |
| (26) | —NH—(CO)—NH— | CH | piperidinyl | —($SO_2$)— | — | 0 | —$CF_2H$ | —$CH_3$ | —$CH_3$ | 1 |
| (27) | —NH—(CO)— | N | piperazinyl | —($SO_2$)— | — | 0 | —$CF_2H$ | —$CH_3$ | —$CH_3$ | 1 |
| (28) | —NH—(CO)—NH— | CH | piperidinyl | —($SO_2$)— | —$CH_2$— | 0 | —$CH_2F$ | —$CH_3$ | —$CH_3$ | 1 |
| (29) | —NH—(CO)— | N | piperazinyl | —($SO_2$)— | —$CH_2$— | 0 | —$CH_2F$ | —$CH_3$ | —$CH_3$ | 1 |
| (30) | —NH—(CO)—NH— | CH | piperidinyl | —($SO_2$)— | —$CH_2$— | 1 | —$CH_3$ | —$CH_3$ | —$CH_3$ | 1 |
| (31) | —NH—(CO)— | N | piperazinyl | —($SO_2$)— | —$CH_2$— | 1 | —$CH_3$ | —$CH_3$ | —$CH_3$ | 1 |
| (32) | —NH—(CO)—NH— | CH | piper?dinyl | —($SO_2$)— | —$CH_2$— | 0 | —C≡N | —$CH_3$ | —$CH_3$ | 1 |
| (33) | —NH—(CO)— | N | piperazinyl | —($SO_2$)— | —$CH_2$— | 0 | —C≡N | —$CH_3$ | —$CH_3$ | 1 |
| (34) | —CH(OH)— | CH | piperidinyl | —($SO_2$)— | —$CH_2$— | 1 | —C≡N | —$CH_3$ | —$CH_3$ | 1 |
| (35) | —$CH_2$— | CH | piperidinyl | —(CO)— | —$NHCH_2$— | 1 | —C≡N | —$CH_3$ | —$CH_3$ | 1 |
| (36) | —CH(OH)— | CH | piperidinyl | —(CO)— | —$NHCH_2$— | 1 | —C≡N | —$CH_3$ | —$CH_3$ | 1 |
| (37) | —O— | CH | piperidinyl | —(CO)— | —$NHCH_2$— | 1 | —C≡N | —$CH_3$ | —$CH_3$ | 1 |
| (38) | —NH—(CO)— | CH | piperidinyl | —(CO)— | —$NHCH_2$— | 1 | —C≡N | —$CH_3$ | —$CH_3$ | 1 |
| (39) | —(CO)—NH— | CH | piperidinyl | —(CO)— | — | 0 | —$CF_2H$ | —$CH_3$ | —$CH_3$ | 1 |
| (40) | —(CO)—NH— | CH | piperidinyl | —($SO_2$)— | —$CH_2$— | 1 | —$CF_2H$ | —$CH_3$ | —$CH_3$ | 1 |
| (41) | —(CO)—NH— | CH | piperidinyl | —(CO)— | —$NHCH_2$— | 1 | —C≡N | —$CH_3$ | —$CH_3$ | 1 |
| (42) | —$CH_2$— | C | imidazolyl | —(CO)— | — | 0 | —$CF_2H$ | —$CH_3$ | —$CH_3$ | 1 |
| (43) | —NH—(CO)— | N | piperazinyl | —($SO_2$)— | — | 0 | —$CF_2H$ | —$CH_3$ | —$CH_3$ | 1 |
| (44) | —NH—(CO)— | N | piperazinyl | —($SO_2$)— | —$CH_2$— | 1 | —C≡N | —$CH_3$ | —$CH_3$ | 1 |
| (45) | —$CH_2$— | CH | piperidinyl | —(CO)— | —$NHCH_2$— | 1 | —$CF_3$ | —$CH_3$ | —CH | 1 |
| (46) | —$CH_2$— | CH | piperidinyl | —($SO_2$)— | —$CH_2$— | 1 | —$CF_3$ | —$CH_3$ | —$CH_3$ | 1 |
| (47) | —O— | CH | piperidinyl | —($SO_2$)— | —$CH_2$— | 1 | —$CF_3$ | —$CH_3$ | —$CH_3$ | 1 |
| (48) | —CH(OH)— | CH | piperidinyl | —(CO)— | — | 0 | —$CF_3$ | —$CH_3$ | —$CH_3$ | 1 |
| (49) | —$CH_2$— | CH | piperidinyl | —(CO)— | — | 0 | —$CF_3$ | —$CH_3$ | —$CH_3$ | 1 |
| (50) | —$CH_2$— | CH | piperidinyl | —(CO)— | — | 0 | —$CF_2CH_3$ | —$CH_3$ | —$CH_3$ | 1 |
| (51) | —$CH_2$— | CH | piperidinyl | —(CO)— | —$CH_2$— | 1 | —$CF_3$ | —$CH_3$ | —$CH_3$ | 1 |
| (52) | —$CH_2$— | CH | piperidinyl | —(CO)— | —$CH_2$— | 1 | —OH | —$CH_3$ | —$CH_3$ | 1 |
| (53) | —$CH_2$— | CH | piperidinyl | —(CO)— | —$CH_2$— | 1 | —$OCH_3$ | —$CH_3$ | —$CH_3$ | 1 |
| (54) | —$CH_2$— | CH | piperidinyl | —(CO)— | — | 0 | —C≡CH | —$CH_3$ | —CH | 1 |
| (55) | —$CH_2$— | CH | piperidinyl | —(CO)— | —$CH_2CH_2$— | 1 | —COOH | —$CH_3$ | —$CH_3$ | 1 |
| (56) | —$CH_2CH_2$— | N | 1,2,3-imidazolyl | — | — | — | — | — | —$CH_3$ | 0 |
| (57) | —$CH_2CH_2$— | N | 1,2,4-imidazolyl | — | — | — | — | — | —$CH_3$ | 0 |
| (58) | —$CH_2CH_2$— | N | 1,3,4-imidazolyl | — | — | — | — | — | —$CH_3$ | 0 |
| (59) | —$CH_2$— | CH | piperidinyl | —(CO)— | — | 0 | —$CF_2CH_3$ | —$CH_3$ | —$CH_3$ | 1 |
| (60) | —$CH_2$— | CH | piperidinyl | —(CO)— | —$CH_2$— | 1 | —$CHFCH_3$ | —$CH_3$ | —$CH_3$ | 1 |
| (61) | —$CH_2$— | CH | piperidinyl | —(CO)— | — | 0 | —$CHFCH_3$ | —$CH_3$ | —$CH_3$ | 1 |
| (62) | —$CH_2$— | CH | piperidinyl | —(CO)— | —$CH_2$— | 1 | —$CF_3$ | —$CH_3$ | —$CH_3$ | 1 |
| (63) | —$CH_2$— | CH | piperidinyl | —(CO)— | — | 0 | cyclopropyl | —$CH_3$ | —$CH_3$ | 1 |
| (64) | —$CH_2$— | CH | piperidinyl | —(CO)— | — | 0 | cyclopentyl | —$CH_3$ | —$CH_3$ | 1 |
| (65) | —$CH_2$— | CH | piperidinyl | —(CO)— | — | 0 | phenyl | —$CH_3$ | —$CH_3$ | 1 |
| (66) | —$CH_2$— | CH | piperidinyl | —(CO)— | — | 0 | CH═$CH(CH_3)_2$ | —$CH_3$ | —$CH_3$ | 1 |
| (67) | —$CH_2$— | CH | piperidinyl | —(CO)— | — | 0 | —COOH | —$CH_3$ | —$CH_3$ | 1 |
| (68) | —$CH_2$— | CH | piperidinyl | —(CO)— | — | 0 | —$OCH_3$ | —$CH_3$ | —$CH_3$ | 1 |
| (69) | —$CH_2$— | CH | piperidinyl | —(CO)— | | 0 | —C≡N | —$CH_3$ | —$CH_3$ | 1 |
| (70) | —$CH_2$— | CH | piperidinyl | —(CO)— | | 0 | —C≡CH | —$CH_3$ | —$CH_3$ | 1 |
| (71) | —$CH_2$— | CH | piperidinyl | —(CO)— | —$CH_2CH_2$— | 1 | cyclopropyl | —$CH_3$ | —$CH_3$ | 1 |
| (72) | —$CH_2$— | CH | piperidinyl | —(CO)— | —$CH_2CH_2$— | 1 | cyclopentyl | —$CH_3$ | —$CH_3$ | 1 |
| (73) | —$CH_2$— | CH | piperidinyl | —(CO)— | —$CH_2CH_2$— | 1 | phenyl | —$CH_3$ | —$CH_3$ | 1 |
| (74) | —$CH_2$— | CH | piperidinyl | —(CO)— | —$CH_2CH_2$— | 1 | CH═$CH(CH_3)_2$ | —$CH_3$ | —$CH_3$ | 1 |
| (75) | —$CH_2$— | CH | piperidinyl | —(CO)— | —$CH_2CH_2$— | 1 | —COOH | —$CH_3$ | —$CH_3$ | 1 |

TABLE 1-continued

| Cpd. | $L^1$ | $X^1$ | CY | $L^2$ | $L^3$ | p | $R^1$ | $R^2$ | $R^3$ | q |
|---|---|---|---|---|---|---|---|---|---|---|
| (76) | $—CH_2—$ | CH | piperidinyl | —(CO)— | $—CH_2CH_2—$ | 1 | $—OCH_3$ | $—CH_3$ | $—CH_3$ | 1 |
| (77) | $—CH_2—$ | CH | piperidinyl | —(CO)— | $—CH_2CH_2—$ | 1 | —C≡N | $—CH_3$ | $—CH_3$ | 1 |
| (78) | $—CH_2—$ | CH | piperidinyl | —(CO)— | $—CH_2CH_2—$ | 1 | —C≡CH | $—CH_3$ | $—CH_3$ | 1 |

Several representative compounds of formula (I) with fluorinated $C_1$-$C_3$ alkyl substituents at $R^1$ include, without limitation, the following structures (I-A), (I-B), (I-C), and (I-D)

(I-A)

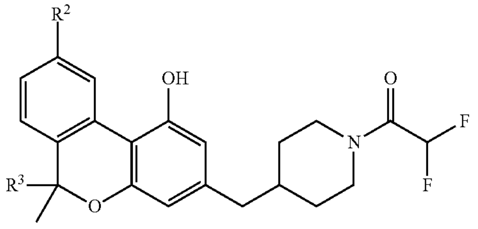

(I-B)

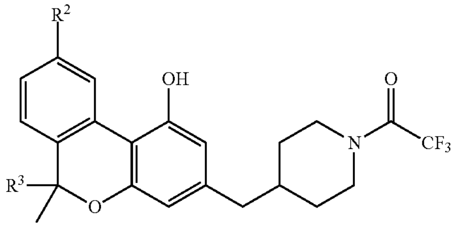

(I-C)

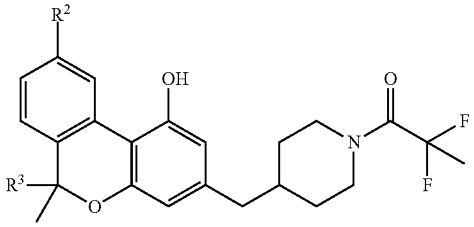

(I-D)

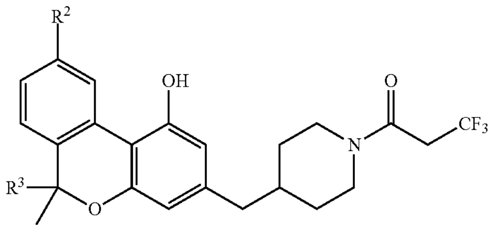

When $R^2$ and $R^3$ are methyl, it will be appreciated that the above four compounds thus have the following structures:

(1)

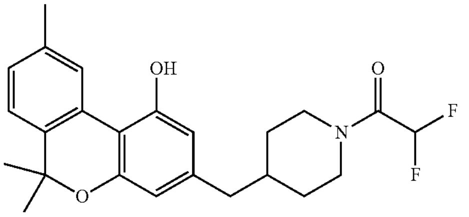

(49)

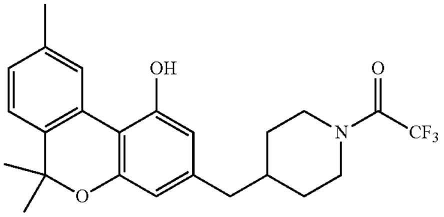

(50)

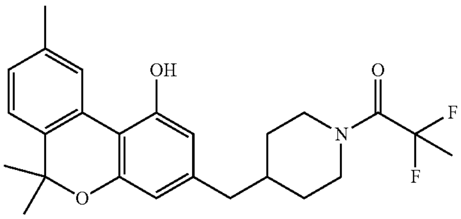

(51)

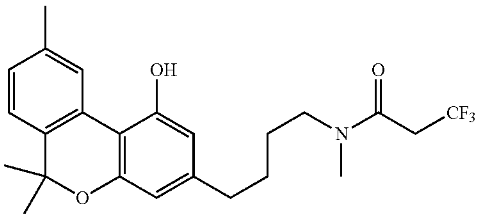

Several other representative compounds having $R^1$ substituents other than fluorinated $C_1$-$C_3$ alkyl, such as hydroxyl, $C_1$-$C_3$ alkoxy, e.g. $C_1$-$C_3$ alkoxy, carboxyl, and ethynyl, are as follows:

(I-E)

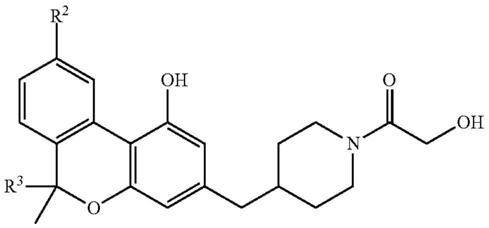

-continued (I-F)

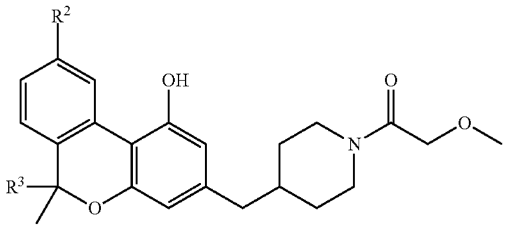

(I-G)

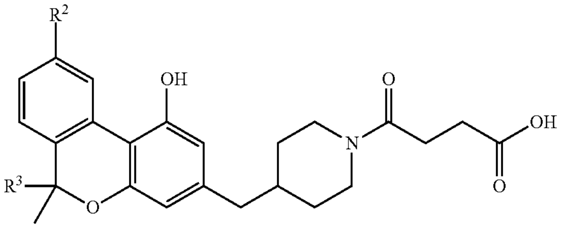

(I-H)

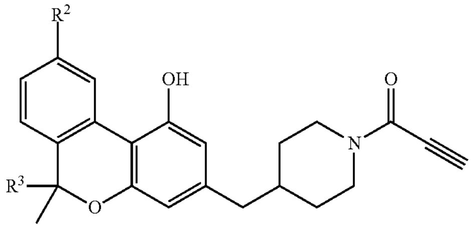

When n is 1 and $R^2$ and $R^3$ are methyl, compounds (I-E) through (I-H) have the following structures:

(52)

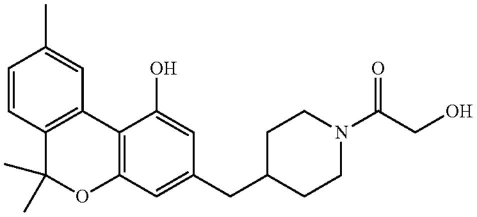

(53)

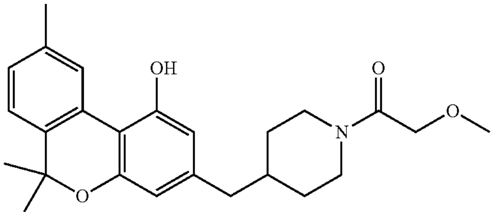

(54)

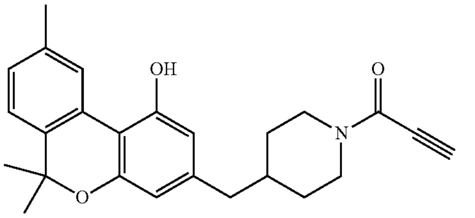

-continued (55)

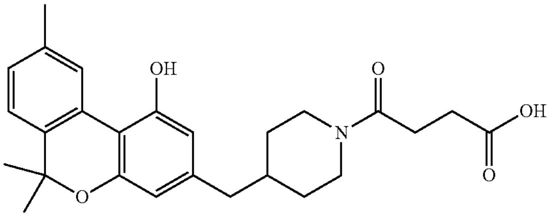

In another embodiment, the invention provides a CBN analog having the structure of formula (II)

(II)

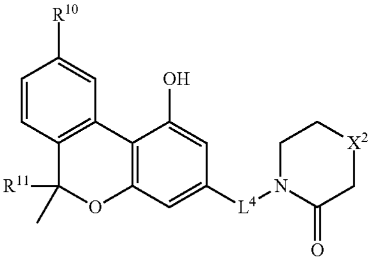

wherein $L^4$, $X^2$, $R^{10}$, and $R^{11}$ are as follows:

$L^4$ is selected from $C_1$-$C_3$ alkylene, $C_2$-$C_3$ alkenylene, hydroxyl-substituted $C_1$-$C_3$ alkylene, hydroxyl-substituted $C_2$-$C_3$ alkenylene, fluorinated $C_1$-$C_3$ alkylene, fluorinated $C_2$-$C_3$ alkenylene, —O—, —(CO)—, —($SO_2$)—, —$NR^7$—, —$NR^7$—(CO)—, —(CO)—$NR^7$—, -and $NR^8$—(CO)—$NR^9$— wherein $R^7$, $R^8$, and $R^9$ are H or $C_1$-$C_3$ alkyl and $R^8$ and $R^9$ may be the same or different. Thus, $R^7$, $R^8$, and $R^9$ may be H or methyl and are typically H.

$L^4$ may be selected from —$CH_2$—, —CH(OH)—, —$CF_2$—, —CHF—, —O—, —($SO_2$)—, —(CO)—, —($SO_2$)—, —NH—, —NH—(CO)—, —(CO)—NH—, and —NH—(CO)—NH—., and, in some embodiments, is —$CH_2$—.

$R^{10}$ is selected from H, $C_1$-$C_3$ alkyl, carboxyl, and $C_2$-$C_6$ alkoxycarbonyl. In some embodiments, $R^{10}$ is H, $C_1$-$C_3$ alkyl, or carboxyl. In some embodiments, $R^{10}$ is H or $C_1$-$C_3$ alkyl. In some embodiments, $R^{10}$ is methyl.

$R^{11}$ is $C_1$-$C_3$ alkyl and is typically methyl.

$X^2$ is selected from O, $NR^{12}$, and $CR^{13}R^{14}$, wherein $R^{12}$ is $C_1$-$C_3$ alkyl or —(CO)—($C_1$-$C_3$ alkyl), and $R^{13}$ and $R^{14}$ are independently H or $C_1$-$C_3$ alkyl or are linked to form a $C_4$-$C_6$ alicyclic ring or a $C_2$-$C_5$ heteroalicyclic ring.

Such compounds include, by way of example, compounds (II-A), (II-B), (II-C), and (II-D):

(II-A)

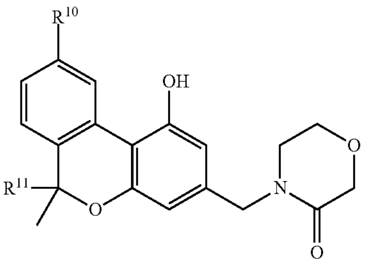

(II-B)

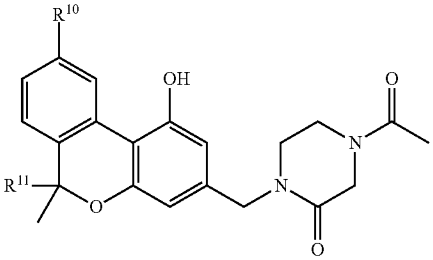

(II-C)

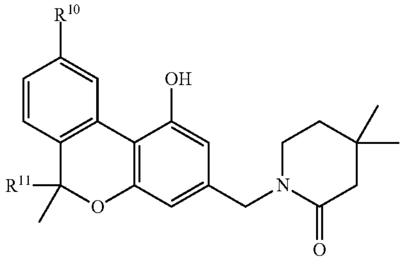

(II-D)

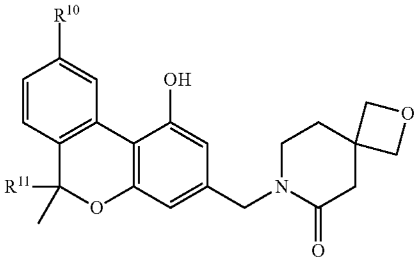

and when $R^{10}$ and $R^{11}$ are both methyl, the compounds have the following structures:

(3)

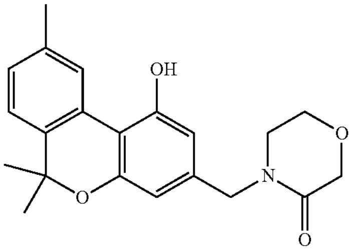

-continued (79)

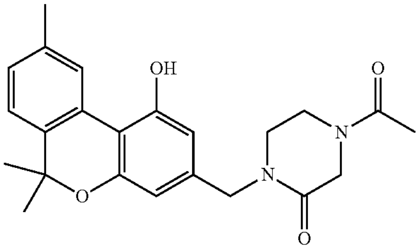

(80)

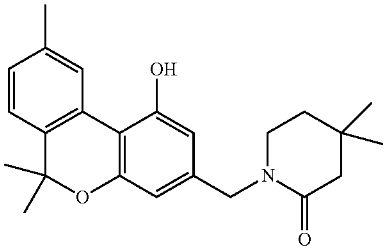

(81)

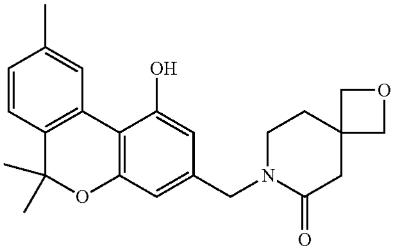

As explained in Part I of this Detailed Description, the compounds of the invention include not only the precise structures of Formulae (I) and (II) but also pharmaceutically acceptable, pharmacologically active analogs thereof, including salts, esters, amides, prodrugs, conjugates, active metabolites, enantiomers, racemic mixtures, hydrates, solvates, complexes, and other such derivatives, analogs, and related compounds.

III. Synthetic Methods

Compounds of formula (I) and (II) may be readily synthesized using the methods described below and set forth in the examples herein.

Synthesis of representative compounds of formula (I), wherein CY is piperidinyl, $L^1$ is $-(CH_2)-$, and $L^2$ is $-(CO)-$, begins with a hydroxyl-protected starting material having the structure (SM-1)

(SM-1)

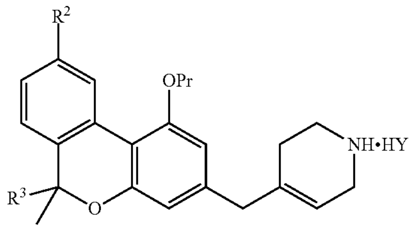

wherein $R^2$ and $R^3$ are as defined previously, Pr is a hydroxyl protecting group, and Y is an anion, such that the compound is in the form of an acid addition salt. Suitable hydroxyl protecting groups, as will be known to those of ordinary skill in the art, include benzyl, tosyl, acetyl, and the like. Y is typically an inorganic anion such as chloro or bromo, or it may be an organic anion such as acetate, carbonate, and so forth. In order to form the amide group and attach -$(L^3)_p$-$R^1$ as shown below

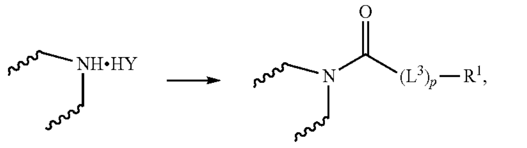

(SM-1) is reacted with an appropriately substituted carboxylic acid $R^1$-$(L^3)_p$-COOH, wherein p, $L^3$, and $R^1$ are as defined previously. This reaction is carried out in a solvent in the presence of base (e.g., DIPEA) and thionyl chloride, to generate the intermediate (INT-13) (see Scheme 1, below). (INT-13) is then hydrogenated under an $H_2$ atmosphere with a suitable catalyst, e.g., Pd/C as used in the example, and the hydroxyl protecting group Pr is removed. The reaction is illustrated in Scheme 1:

Scheme 1

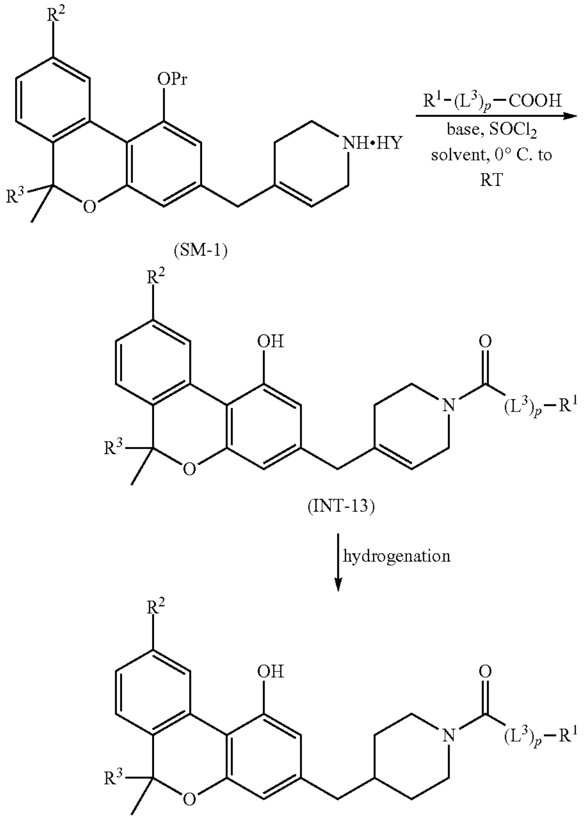

(SM-1)

(INT-13)

(I-1)

The reaction described in detail in Example 1 is representative of the synthesis of Scheme 1. In Example 1, the carboxylic acid reagent $R^1$-$(L^3)_p$-COOH is $CHF_2COOH$ (i.e., p is zero) and the fluorinated CBN analog synthesized is compound (1).

In Example 2, an alternative methodology is provided to generate the amide group. In this embodiment, (SM-1) undergoes a reaction with acetyl chloride in the presence of base to provide a —(CO)-$(L^3)_p$-$R^1$ substituent, wherein, in the example, p is zero and $R^1$ is methyl.

In addition to the methods of Examples 1 and 2, reaction of (SM-1) to generate (INT-13) can be promoted using any of a variety of coupling strategies. Suitable reagents and conditions for amide bond formation include, by way of example:

Carbodiimide-based reagents such as dicyclohexylcarbodiimide (DCC), 1-ethyl-3-(3-dimethylaminopropyl)carbodiimide hydrochloride (EDCI), and N,N'-diisopropylcarbodiimide (DIC), optionally used in combination with additives such as butyl alcohol, N-hydroxysuccinimide or ethyl(hydroxyimino)cyanoacetate, and a base, e.g., N-methylmorpholine (NMM), triethylamine (TEA), or N,N-diisopropylethylamine (DIPEA);

2—Uronium- and phosphonium-based reagents, including O-(7-azabenzotriazol-1-yl)-N,N,N',N'-tetramethyluronium hexafluorophosphate (HATU), O-(benzotriazol-1-yl)-N,N,N',N'-tetramethyluronium tetrafluoroborate (TBTU), O-(benzotriazol-1-yl)-N,N,N',N'-tetramethyl-uronium hexafluorophosphate (HBTU), and benzotriazol-1-yloxytripyrrolidinophosphonium hexafluorophosphate (PyBOP), which are typically used in the presence of a tertiary amine such as DIPEA or NMM;

3—Phosphonic anhydrides, such as propylphosphonic anhydride (T3P); and

4—Mixed anhydride methods, including the use of chloroformates (e.g., isobutyl chloroformate) or pivaloyl chloride, in the presence of tertiary amines such as NMM or TEA.

Other compounds having the structural formula (I), including the compounds in Table 1, can be synthesized using variations on these methods that will be apparent to those of ordinary skill in the art, based on their inherent knowledge as synthetic organic chemists, and/or by reference to the pertinent texts and literature. For instance, in order to synthesize compounds wherein $L^2$ is —$(SO_2)$— rather than —(CO)— as exemplified above, a sulfonic acid $R^1$-$(L^3)_p$-$(SO_2)$—OH or a sulfonyl chloride $(L^3)_p$-$(SO_2)$—Cl would be used in place of the carboxylic acid $R^1$-$(L^3)_p$-COOH. As another example, compounds of formula (I) wherein $X^1$ is N in lieu of CH, as in the examples above, can be prepared using a method akin to that described below with respect to synthesis of CBN analogs having the molecular structure of formula (II).

CBN analogs of formula (II) are synthesized from a starting material comprising a hydroxyl-protected cannabinol core substituted at the 3-position with a leaving group LG through a linker $L^2$. The starting material here has the structure of formula (SM-2)

(SM-2)

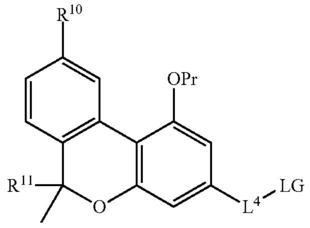

wherein:

$R^{10}$, $R^{11}$ and $L^4$ are as defined previously;

Pr is a hydroxyl-protecting group defined as for the protecting group Pr in (SM-1); and LG is a leaving group displaceable by an incoming nitrogen nucleophile. The leaving group may be Cl, Br, $HSO_4$, or the like, with Cl representing the leaving group in compound (INT-7) of Example 3. The reaction is carried out in the presence of a strong base, e.g., NaH, with a reactant suitable to provide the desired product, i.e., a reactant having the structure of formula (III)

(III)

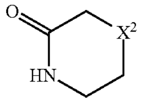

in which $X^2$ is as defined previously. The ideal reaction conditions will depend on the particular reagents, starting material, substituents, and the like, but will generally involve a reaction temperature in the range of 0° C. to room temperature and a reaction time of at least 2 hours, typically 2 hours to 5 hours. The intermediate provided by the aforementioned reaction is then deprotected with a conventional reagent suitable for removing hydroxyl protecting group and regenerating the hydroxyl substituent.

The reaction is illustrated schematically in Scheme 2:

Scheme 2

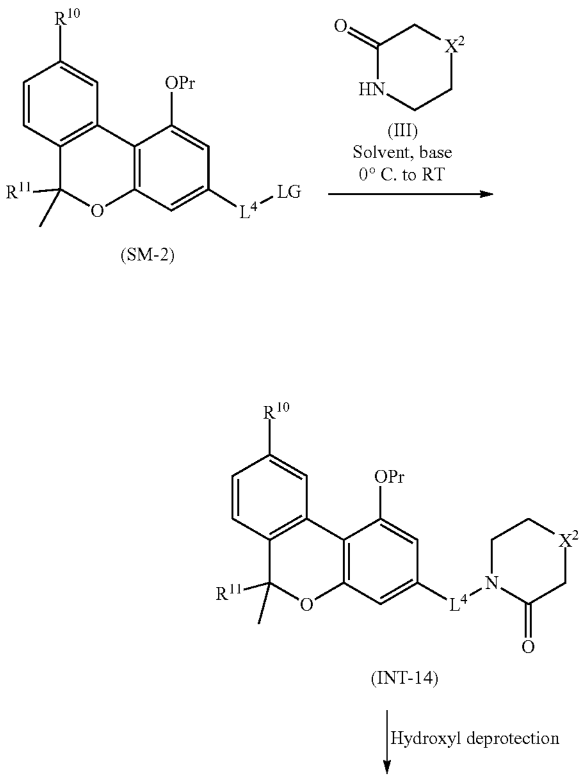

(III)

(SM-2)

(INT-14)

-continued

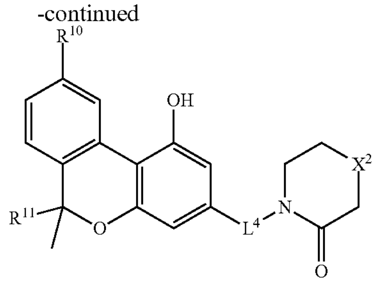

(II)

In Example 3, (SM-2) is 1-(benzyloxy)-3-(chloromethyl)-6,6,9-trimethyl-6H-benzo[c]chromene, reactant (Ill) is 3-morpholinone, used to prepare CBN analog (3) via the hydroxyl-protected intermediate. In other representative reactions, N-acyl-substituted piperazine serves as reactant (III) to prepare CBN analog (79), or 4,4-dimethyl-piperidin-2-one serves as reactant (Ill) to prepare CBN analog (80).

Other CBN analogs of the invention may be prepared using methodologies identical or analogous to those described above and set forth in the examples herein, as will be appreciated by those of ordinary skill in the art. Such methods may be augmented by reference to the pertinent texts and literature, and/or by the inherent knowledge of a skilled practitioner, as noted above. These methods may involve modification of the present reaction products to provide desired derivatives.

IV. Pharmaceutical Formulations, Dosage Forms, and Modes of Administration

Pharmaceutical formulations suitable for administration of a CBN analog of the invention are formulations wherein the CBN analog, as a pharmacologically active agent, is contained in a therapeutically effective amount, i.e., in an amount or concentration effective to achieve its intended purpose. Typically, the therapeutically effective amount is a unit dose, as explained infra. The CBN analog may be in the form of a reaction product composition, but more typically is in isolated, purified form.

Determination of a therapeutically effective amount for a particular CBN analog is within the capability of those skilled in the art. Generally, toxicity and therapeutic efficacy of a compound or formulation described herein can be determined by standard pharmaceutical procedures in cell cultures or experimental animals, e.g., procedures used for determining the maximum tolerated dose (MTD), the ED50, which is the effective dose to achieve 50% of maximal response, and the therapeutic index (TI), which is the ratio of the MTD to the ED50. Compounds and formulations with high TIs are the more preferred compounds and formulations herein, and preferred dosage regimens are those that maintain plasma levels of the active agents at or above a minimum concentration to maintain the desired therapeutic effect. Dosage will, of course, also depend on a number of factors, including the particular CBN analog, the formulation type, the site of intended delivery, the route of administration, and other pertinent factors known to the prescribing physician.

Administration of a CBN analog of the invention may be carried out using any appropriate mode of administration. Thus, administration can be, for example, oral, parenteral, transdermal, transmucosal (including intrarectal and intravaginal, via suppository, ointment, cream, or the like), sublingual, by inhalation, or via an implanted reservoir in a dosage form. The term "parenteral" as used herein is intended to include subcutaneous, intravenous, and intramuscular injection. Depending on the intended mode of administration, the pharmaceutical formulation containing the CBN analog may be a solid, semi-solid or liquid, such as, for example, a tablet, a capsule, a caplet, a gummy, a lozenge (e.g., a troche), a solution (e.g., an elixir or syrup), a suspension (e.g., an emulsion), a suppository, granules, pellets, beads, a powder, or the like, preferably, although not necessarily, in unit dosage form suitable for single administration of a precise dosage. As is understood in the field of pharmaceutical formulation, a "unit dosage" refers to the amount of an active agent in a single dose to be administered to a subject, with a "unit dosage form" referring to a dosage form that contains a unit dosage. Suitable pharmaceutical formulations may be prepared using conventional methods known to those in the field of pharmaceutical formulation and described in the pertinent texts and literature, e.g., in Remington: The Science and Practice of Pharmacy, cited supra.

For solid compositions, conventional nontoxic solid carriers include, by way of example, pharmaceutical grades of mannitol, lactose, starch, magnesium stearate, sodium saccharin, talc, cellulose, glucose, sucrose, magnesium carbonate, and the like. Liquid pharmaceutically administrable formulations can, for example, be prepared by dissolving, dispersing, etc., an active agent as described herein and one or more optional pharmaceutical adjuvants as excipients, such as, for example, water, saline, aqueous dextrose, glycerol, ethanol, and the like, to thereby form a solution or suspension. If desired, the pharmaceutical formulation to be administered may also contain minor amounts of nontoxic auxiliary substances such as wetting or emulsifying agents, pH buffering agents and the like, for example, sodium acetate, sorbitan mono-laurate, triethanolamine sodium acetate, triethanolamine oleate, etc. See Remington's Pharmaceutical Sciences, referenced above.

For those CBN analogs that are orally active, oral dosage forms are generally preferred, and include, without limitation, tablets, capsules, caplets, gummies, lozenges (e.g., troches), suspensions (e.g., emulsions), oral gels, and solutions (e.g., elixirs and syrups), and may also comprise a plurality of dispersible granules, beads, powders, or pellets that may or may not be encapsulated. Preferred oral dosage forms are tablets, capsules, gummies, and solutions.

Tablets may be manufactured using standard tablet processing procedures and equipment. Direct compression and granulation techniques are preferred. In addition to the active agent, tablets will generally contain inactive, pharmaceutically acceptable carrier materials such as binders (e.g., starches, acacia, alginates, carboxymethylcellulose, polyvinyl pyrrolidone, and the like), lubricants (e.g., stearic acid or stearates such as magnesium stearate and calcium stearate), disintegrants (e.g., starches, clays, celluloses, etc.), fillers (e.g., silicon dioxide, kaolin, microcrystalline cellulose, anhydrous lactose, sorbitol, etc., as is known in the art), stabilizers, surfactants, coloring agents, antioxidants, preservatives, and the like. Tablets may be prepared so as to be swallowed intact, or they may contain disintegrants, taste-masking agents, or the like, so as to be rendered chewable.

Capsules are also suitable oral dosage forms for those CBN analogs that are orally active, in which case the analog-containing formulation may be encapsulated in the form of a liquid or solid (including particulates such as granules, beads, powders or pellets). Suitable capsules may be either hard or soft, and are generally made of gelatin, starch, or a cellulosic material, with gelatin capsules preferred. Two-piece hard gelatin capsules are preferably sealed, such as with gelatin bands or the like. See, for example, Remington: The Science and Practice of Pharmacy, cited supra, which describes materials and methods for preparing encapsulated pharmaceuticals.

Pharmaceutical gummies are also suitable dosage forms for orally administering a CBN analog of the invention. As is known in the art, gummies are comprised of a gelling agent, i.e., gelatin and/or a gelatin equivalent such as pectin or xanthan gum; a sweetener, which may be sugar-based (e.g., sucrose, glucose syrup, etc.) or a non-sucrose natural or artificial sweetener (e.g., sucralose, sorbitol, erythritol, *stevia*, corn syrup, agave syrup, etc.); a flavoring; a colorant; and generally, although not necessarily, one or more optional excipients in addition to the foregoing, such as stabilizers, solubilizers, taste-masking agents, anti-oxidants, preservatives, and the like. A gummy formulation of the invention, then, comprises a therapeutically effective amount of a CBN analog of the invention; gelatin and/or a gelatin equivalent; a sweetener; a flavoring; a colorant; and, optionally, one or more of the excipients mentioned above. An example of a gummy formulation for administering a CBN analog of the invention comprises the following components: 0.25 wt. % to 20 wt. % of the CBN analog; 2.5 wt. % to 10 wt. % gelling agent; and 10 wt. % to 60 wt. % sweetener, with water representing the remainder of the formulation. For example, a gummy formulation of the invention may comprise 0.25 wt. % to 15 wt. % of the CBN analog (e.g., 0.25 wt. % to 5.0 wt. %); 3.0 wt. % to 7.5 wt. % gelling agent; and 20 wt. % to 50 wt. % sweetener. Optionally, the formulation may also include one or more excipients that can serve to enhance taste, appearance, stability, and overall product quality. Such excipients include, without limitation, flavoring agents, colorants, preservatives, emulsifiers, and the like.

Some dosage forms, whether tablets, capsules, caplets, lozenges, particulates, implants, or suppositories, may, if desired, be formulated so as to provide for controlled release of the active agent. A preferred form of controlled release herein is sustained release, so as to provide gradual release of the CBN analog from the dosage form over an extended time period, e.g., 12-36 hours, 12-24 hours, or the like. Generally, as will be appreciated by those of ordinary skill in the art, sustained release dosage forms are formulated by dispersing the CBN analog within a matrix of a gradually hydrolyzable material such as a hydrophilic polymer, or by coating a solid, drug-containing dosage form with such a material. Hydrophilic polymers useful for providing a sustained release coating or matrix include, by way of example: cellulosic polymers such as hydroxypropyl cellulose, hydroxyethyl cellulose, hydroxypropyl methyl cellulose, methyl cellulose, ethyl cellulose, cellulose acetate, and carboxymethylcellulose sodium; acrylic acid polymers and copolymers, preferably formed from acrylic acid, methacrylic acid, acrylic acid alkyl esters, methacrylic acid alkyl esters, and the like, e.g. copolymers of acrylic acid, methacrylic acid, methyl acrylate, ethyl acrylate, methyl methacrylate and/or ethyl methacrylate; and vinyl polymers and copolymers such as polyvinyl pyrrolidone, polyvinyl acetate, and ethylene-vinyl acetate copolymer.

Preparations for parenteral administration of the CBN analog include sterile aqueous and nonaqueous solutions, suspensions, and emulsions. Injectable aqueous solutions contain the CBN analog in water-soluble form. Examples of nonaqueous solvents or vehicles include fatty oils, such as olive oil and corn oil, synthetic fatty acid esters, such as ethyl oleate or triglycerides, low molecular weight alcohols such as propylene glycol, synthetic hydrophilic polymers such as polyethylene glycol, liposomes, and the like. Parenteral formulations may also contain adjuvants such as solubilizers, preservatives, wetting agents, emulsifiers, dispersants, and stabilizers, and aqueous suspensions may contain substances that increase the viscosity of the suspension, such as sodium carboxymethyl cellulose, sorbitol, and dextran. Injectable formulations are rendered sterile by incorporation of a sterilizing agent, filtration through a bacteria-retaining filter, irradiation, or heat. They can also be manufactured using a sterile injectable medium. The active agent may also be in dried, e.g., lyophilized, form that may be rehydrated with a suitable vehicle immediately prior to administration via injection.

Suppositories can also be prepared to administer a CBN analog of the invention vaginally or rectally. As is known in the art, suppositories are prepared by mixing an active agent with a suitable non-irritating base material that is solid at ordinary (e.g., storage) temperatures but liquid at internal body temperature, so that the suppository melts and begins releasing the active agent therein after administration. The base material makes up the majority of the suppository's weight, which is typically in the range of 1 g to 4 g, and may be an oleaginous base, e.g., cocoa butter, a hydrogenated vegetable oil, a synthetic triglyceride, etc.; a hydrophilic water-soluble or water-miscible base, e.g., glycerinated gelatin or polyethylene glycols; or a water-dispersible base, typically an oleaginous base mixed with one or more surfactants to increase hydrophilicity. Generally, suppositories additionally contain at least one excipient, typically selected from suspending agents, emulsifying agents, stiffening agents, preservatives, lubricants, and the like. Depending on the particular active agent and the selected suppository base and excipients, the active agent will generally represent in the range of 1 wt. % to 25 wt. % of the suppository, more typically in the range of 2.5 wt. % to 15 wt. %.

An example of a suppository formulated with a CBN analog of the invention is an intravaginal suppository, formulated to treat, for instance, endometriosis or a symptom thereof, wherein the suppository comprises 0.25 wt. % to 50 wt. %, 0.25 wt. % to 30 wt. %, 0.25 wt. % to 20 wt. %, 0.25 wt. % to 10 wt. %, 0.25 wt. % to 5 wt. %, 0.5 wt. % to 50 wt. %, 0.5 wt. % to 30 wt. %, 0.5 wt. % to 20 wt. %, 0.5 wt. % to 10 wt. %, 0.5 wt. % to 5 wt. %, 1.0 wt. % to 50 wt. %, 1.0 wt. % to 30 wt. %, 1.0 wt. % to 20 wt. %, 1.0 wt. % to 10 wt. %, 1.0 wt. % to 5 wt. %, 2.5 wt. % to 50 wt. %, 2.5 wt. % to 30 wt. %, 2.5 wt. % to 20 wt. %, 2.5 wt. % to 10 wt. %, 2.5 wt. % to 5 wt. %, of a CBN analog as provided herein, i.e., a CBN analog having the molecular structure (I) or (II) and thus including compound (1), compound (2), compound (3), or any compound of Table 1, and 15 wt. % to 75 wt. % suppository base as provided above, with one or more excipients making up the remainder of the dosage form.

A CBN analog as provided herein can also be administered intravaginally in the treatment of endometriosis or other conditions using a different type of physical form, e.g., an ointment, cream, gel, liquid, or the like. Ointments, as is well known in the art of pharmaceutical formulation, are semisolid preparations that are typically based on petrolatum or other petroleum derivatives. The specific ointment base to be used is one that will provide for optimum drug delivery. As with other carriers or vehicles, an ointment base should be inert, stable, nonirritating and nonsensitizing. As explained in Remington: The Science and Practice of Pharmacy, 19th Ed. (Easton, Pa.: Mack Publishing Co., 1995), at pages 1399-1404, ointment bases may be grouped in four classes: oleaginous bases; emulsifiable bases; emulsion bases; and water-soluble bases. Oleaginous ointment bases include, for example, vegetable oils, fats obtained from animals, and semisolid hydrocarbons obtained from petroleum. Emulsifiable ointment bases, also known as absorbent ointment bases, contain little or no water and include, for example, hydroxystearin sulfate, anhydrous lanolin, and hydrophilic petrolatum. Emulsion ointment bases are either water-in-oil (W/O) emulsions or oil-in-water (O/W) emulsions, and include, for example, cetyl alcohol, glyceryl monostearate, lanolin, and stearic acid. Preferred water-soluble ointment bases are prepared from polyethylene glycols of varying molecular weight; again, see Remington: The Science and Practice of Pharmacy for further information. Creams, including creams for intravaginal administration of a CBN analog of the invention, are viscous liquids or semisolid emulsions, either oil-in-water or water-in-oil. Cream bases are water-washable, and contain an oil phase, an emulsifier, and an aqueous phase. The oil phase, also called the "internal" phase, is generally comprised of petrolatum and a fatty alcohol such as cetyl or stearyl alcohol. The aqueous phase usually, although not necessarily, exceeds the oil phase in volume, and generally contains a humectant. The emulsifier in a cream formulation is generally a nonionic, anionic, cationic, or amphoteric surfactant. The concentration of CBN analog in the ointment or cream is present within the same ranges as the concentration of the analog in a suppository, provided above.

The CBN analog may, in addition, be administered through the skin using conventional transdermal drug delivery systems, wherein the active agent is contained within a laminated structure that serves as a drug delivery device to be affixed to the skin. In such a structure, the drug formulation is contained in a layer, or "reservoir," underlying an upper backing layer. The laminated structure may contain a single reservoir, or it may contain multiple reservoirs. In one embodiment, the reservoir comprises a polymeric matrix of a pharmaceutically acceptable contact adhesive material that serves to affix the system to the skin during drug delivery. Alternatively, the drug-containing reservoir and skin contact adhesive are present as separate and distinct layers, with the adhesive underlying the reservoir which, in this case, may be either a polymeric matrix as described above, or it may be a liquid or hydrogel reservoir, or may take some other form. Transdermal drug delivery systems may in addition contain a skin permeation enhancer to facilitate passage of the active agent through the skin.

In addition, the CBN analog may be formulated in a depot preparation for controlled release of the active agent, preferably sustained release over an extended time period. These sustained release dosage forms are generally administered by implantation (e.g., subcutaneously or by intramuscular injection).

The CBN analog can also be formulated for inhalation, e.g., as a solution in saline, as a dry powder, or as an aerosol. Administration may be via the intranasal route or via oral inhalation. A pharmaceutical formulation for delivery to the lungs via oral inhalation can also be a dry powder formulation, such as may comprise nanoparticle-sized solid particles containing the CBN analog and suitable dry powder excipients, for example, lactose monohydrate, magnesium stearate, mannitol, or the like. Suitable dry powder components and inhaler types are described, inter alia, by de Boer (2017) *Expert Opin Drug Deliv.* 14(4): 499-512, and U.S. Patent Publication No. 2009/00004279 to Hofmann et al., both incorporated by reference herein.

A suitable unit dose of the CBN analog for a 70 kg human is typically in the range of 5 mg to 500 mg, e.g., 5 mg to 250 mg, 5 mg to 100 mg, 5 mg to 75 mg, 5 mg to 60 mg, 5 mg to 50 mg, 5 mg to 30 mg, 5 mg to 15 mg, 10 mg to 150 mg, 10 mg to 100 mg, 10 mg to 75 mg, 10 mg to 60 mg, 10 mg to 50 mg, 10 mg to 30 mg, 20 mg to 200 mg, 20 mg to 100 mg, or 20 mg to 50 mg, with a typical daily dose in the range of about 10 mg to 1000 mg, 10 mg to 500 mg, 10 mg to 200 mg, e.g., 10 mg to 150 mg, 10 mg to 120 mg, 10 mg to 100 mg, 10 mg to 60 mg, 10 mg to 30 mg, 20 mg to 300 mg, 20 mg to 200 mg, 20 mg to 150 mg, 20 mg to 120 mg, 20 mg to 100 mg, 20 mg to 60 mg, 40 mg to 400 mg, 40 mg to 200 mg, or 40 mg to 100 mg.

Depending on the type of formulation or dosage form, the amount of the CBN analog therein will generally be in the range of 0.25 wt. % to 99 wt. %, 0.25 wt. % to 75 wt. %, 0.25 wt. % to 50 wt. %, 0.25 wt. % to 20 wt. %, 1 wt. % to 95 wt. %, e.g., 5 wt. % to 95 wt. %, 5 wt. % to 90 wt. %, 10 wt. % to 80 wt. %, 15 wt. % to 75 wt. %, and so forth. Typical concentrations of the CBN analog in intravaginal suppository formulations, specifically, are delineated above, as is the typical range of concentrations of the CBN analog in a gummy dosage form.

For nonsolid formulations specifically, such as ointments, creams, parenteral formulations, and the like, including intravaginally administered nonsolid formulations, the unit dose of the CBN analog is present at a concentration that will yield a unit dose within the above ranges. Thus, for example, when the desired unit dosage of the CBN analog is in the range of 10 mg to 150 mg, a concentration of the analog in the range of 0.25 wt. % to 30 wt. % is appropriate in a 500 mg to 4000 mg quantity of ointment, cream, or the like that is administered. As another example, when the desired unit dosage of the CBN analog is in the range of 20 mg to 50 mg, a concentration of the analog in the range of 0.5 wt. % to 10 wt. % is appropriate in a 500 mg to 4000 mg quantity of ointment, cream, or the like. As another example, when the desired unit dosage of the CBN analog is in the range of 20 mg to 50 mg, a concentration of the analog in the range of 1.0 wt. % to 5 wt. % is appropriate in a 1000 mg to 2000 mg quantity of ointment, cream, or the like.

The invention thus provides, in one embodiment, a pharmaceutical formulation for administration of a CBN analog of the invention to a subject, wherein the pharmaceutical formulation comprises a therapeutically effective amount of the CBN analog and at least one pharmaceutically acceptable excipient. In a related embodiment, the pharmaceutical formulation is a unit dosage form and comprises 5 mg to 500 mg of the CBN analog.

V. Indications and Methods of Use

The CBN analogs of the invention exhibit affinity for at least one pharmacological receptor, i.e., a specialized target molecule within or on a cell that binds to a pharmacologically active agent and mediates its effect, wherein the receptors to which the CBN analogs of the invention exhibit include the cannabinoid receptors CB1 and CB2 receptor; orphan G-protein coupled receptors (GPCRs) such as GPR55, GPR18, and GPR119; transient receptor potential (TRP) channels such as $TRPV_1$, $TRPA_1$, and TRPM8; serotonin receptors such as 5-HT1A and 5-HT2A; peroxisome proliferator-activated receptors (PPARs) such as PPAR-α and PPAR-γ; and additional CNS- and inflammation-related receptors such as sigma-1, adenosine A2A, and opioid receptors.

Accordingly, in one method, a CBN analog of the invention has utility in a method for binding to a pharmacological receptor. In one embodiment of the method, a CBN analog of the invention has utility in a method for binding to a cannabinoid receptor. In a related embodiment, a CBN analog of the invention is used to treat a disease, disorder or other adverse condition in a subject, wherein the disease, disorder or other adverse condition is one that is responsive to administration of a therapeutically effective amount of a compound that acts as a cannabinoid receptor binding ligand. By "responsive" is meant that administration of the CBN analog is effective as a disease-modifying therapy (DMT), i.e., a therapy that delays, slows, or reverses the progression of a disease.

A CBN analog of the invention typically exhibits a different level of activity at the CB1 receptor relative to the CB2 receptor (see, e.g., Example 10), i.e., exhibits greater selectivity at one of the two receptors. The compound may also exhibit a different type of activity, i.e., a different type of binding, at the CB1 receptor relative to the CB2 receptor, e.g., the CBN analog may act as an agonist, partial agonist, antagonist, inverse agonist, indirect agonist, or the like, at one but not both of the CB1 and CB2 receptors. See Example 7. For instance, compound (2) is an unbiased partial agonist at the CB1 receptor and an inverse agonist at the CB2 receptor, while compound (3) is a G-protein-biased partial agonist at the CB1 receptor and an inverse agonist at the CB2 receptor. A CBN analog herein may, therefore, be used in a method for selectively modulating a cannabinoid receptor, i.e., to enhance or reduce the activity of that receptor.

The CBN analog is generally administered to a subject within the context of an ongoing dosage regimen, although occasional, as-needed administration is also contemplated. The CBN analog is generally, although not necessarily, administered to the subject in a pharmaceutical formulation or dosage form, preferably in a unit dosage form.

As noted above, then, the CBN analogs of the invention are useful in a method for treating a disease, disorder, or other adverse condition that is responsive to the administration of a compound that acts as a cannabinoid receptor binding ligand. Such diseases, disorders, and other adverse conditions encompass therapeutic indications including, without limitation, treatment of: pain; health conditions specific to women, such as endometriosis, dysmenorrhea, premenstrual syndrome, and uterine fibroid pain; alcoholism; anxiety; autism spectrum disorder; autoimmune disorders such as inflammatory bowel disease (IBD) (e.g., Crohn's disease, ileitis, ulcerative colitis), celiac disease, systemic lupus erythematosus, Addison's disease, Graves' disease, Hashimoto thyroiditis, myasthenia gravis, psoriasis, Sjögren's disease, pernicious anemia, vasculitis, autoimmune hepatitis, and type 1 diabetes; burns, including first-degree, second-degree, and third-degree burns, including thermal burns, radiation burns, chemical burns, and electrical burns; cancer, particularly cancers that tend to respond poorly to systemic chemotherapy, such as sarcomas, particularly osteosarcomas, brain cancers, and prostate cancers; cardiac disorders such as congestive heart failure, myocardial infarction, cardiomyopathy, and peripheral artery disease; cognitive pain and mild cognitive impairment; non-neurodegenerative dementia such as vascular dementia; demyelinating disorders such as multiple sclerosis, chronic inflammatory demyelinating polyneuropathy (CIDP), and Guillain-Barre Syndrome; dental disorders, primarily those associated with pain, inflammation, infection, and/or physical trauma, e.g., gingivitis and periodontitis; type 2 diabetes and glucose regulation; drug withdrawal, particularly opioid withdrawal (for instance, treatment of an individual who has stopped opioid use or is in the process of reducing the regular dosage of an opioid); fibroses, including kidney fibrosis, liver fibrosis, lung fibrosis, and systemic fibrosis; hypersensitivity-related maladies, particularly adverse skin reactions such as psoriasis, contact dermatitis, eczema, infectious skin ulcers, and cellulitis; immunodeficiency, including, but not limited to, primary immunodeficiency; inflammation, including inflammation-related arthritic disorders and inflammatory gastrointestinal disorders; ischemia, including cerebral ischemia, mesenteric ischemia, and kidney ischemia; infertility or limited fertility; liver diseases such as fatty liver disease, cirrhosis, and hepatitis; Metabolic Syndrome (Syndrome X) and any one of the conditions associated therewith; migraines and other types of headaches; nausea, including motion sickness; neurological and neurodegenerative disorders, including Alzheimer's disease, Parkinson's disease, Huntington's Disease, multiple sclerosis, amyotrophic lateral sclerosis, fronto-temporal dementia with Parkinson's features, progressive supranuclear palsies, essential dyskinesias, tardive dyskinesia, transverse myelitis, neurodegenerative cerebellar ataxia, aphasia, Bell's Palsy, Creutzfeldt-Jakob Disease, encephalitis, Amyotrophic Lateral Sclerosis (ALS), muscular dystrophy, and Ménière's Disease; obesity and overweight, as well as conditions caused by or associated with excess weight or obesity; osteoporosis, osteopenia, and regulation of bone mass; pelvic pain in both men and women; psychiatric disorders such as attention deficit hyperactivity disorder (ADHD), bipolar disorder, depression, obsessive compulsive disorder (OCD), post-traumatic stress disorder (PTSD), psychosis, and schizophrenia; respiratory disorders such as asthma, chronic obstructive pulmonary disease, bronchitis, and pneumonia; seizure disorders such as epilepsy; skin disorders such as acne and eczema; sleep disorders including apnea, insomnia, restless leg syndrome, and REM sleep dysfunction; and stress.

Treatment of pain is of particular interest, regardless of pain origin, duration, or severity. In one embodiment, then, a CBN analog of the invention is administered to a subject to treat pain, where the pain may be acute or chronic and may be, by way of example, post-surgical pain (such as pain associated with bunion surgery, dental surgery, or major surgery), pain incident to an injury, chemotherapy induced pain, pain associated with interstitial cystitis (bladder pain syndrome) and urinary tract infections, back pain of various types and origins, vascular-type pain such as that associated with migraines, and the like. A CBN analog of the invention is useful in a method to treat neuropathic pain, i.e., pain arising from nerve damage, such as central pain syndrome, complex regional pain syndrome, peripheral neuropathic pain (e.g., diabetic peripheral neuropathic pain), shingles and postherpetic neuralgia. The present CBN analogs are also useful in a method for treating nociceptive pain, including somatic nociceptive pain, i.e., pain due to stimulation of peripheral nociceptors capable of responding to stimuli such as mechanical (pressure), thermal, chemical, and other stimulation; examples of nociceptive pain include pain associated with burn, fractures, incisions, wounds, cellulitis, shingles, arthritis, and gout. Nociceptive pain treatable with a CBN analog as provided herein also includes visceral pain, i.e., pain originating from viscera, muscles and bone, such as pain arising from tumor invasion, internal obstructions (e.g., of the bowel, ureter, or bile duct), colic, angina, and pancreatitis. Finally, a CBN analog as provided herein is useful to treat mixed pain, i.e., pain with both nociceptive and neuropathic symptoms. Examples of the foregoing include, without limitation, cancer pain, osteoarthritis pain, persistent postsurgical pain, and myofascial pain syndrome such as fibromyalgia.

In another embodiment, the invention provides a method for treating women's health conditions, such as endometriosis, primary and secondary dysmenorrhea, premenstrual syndrome, uterine fibroid pain and symptoms thereof, adenomyosis, polycystic ovary syndrome (PCOS), and menopausal symptoms, including a decrease in fertility. Evaluation of representative CBN analogs (1), (2) and (3) in the treatment of endometriosis pain is described in the examples herein. As with other methods of treatment herein, the CBN analog can be administered to the subject via any suitable mode of administration. However, it will be appreciated that for at least some of the aforementioned indications, vaginal administration of the CBN analog using a suppository is preferred.

In a further embodiment, the invention provides a method for treating a subject suffering from stress and/or anxiety, including chronic anxiety; anxiety associated with a specific anxiety disorder such as obsessive compulsive disorder, seasonal affective disorder, panic disorder, social anxiety disorder, and separation anxiety disorder; chronic or occasional difficulty sleeping; event-centric nervousness; generalized anxiety; post-traumatic stress disorder; and mild to moderate phobias.

In another embodiment, the invention provides a method for treating inflammation, i.e., for treating a condition, disease or disorder caused by or otherwise associated with inflammatory processes. In this embodiment, the method involves administration of a CBN analog as described herein to a subject afflicted with an inflammatory condition, disease, or disorder. Unabated inflammation plays a role in many disease pathologies, including, but not limited to, inflammation-related arthritic disorders such as rheumatoid arthritis, osteoarthritis, spondyloarthropathies (e.g., psoriatic arthritis) and myopathies, as well as inflammation-related myopathies that are not technically classified as arthritis, but involve similar symptoms, e.g., inflammation of tendons or ligaments ("soft tissue rheumatism") such as frozen shoulder, tennis elbow, carpal tunnel syndrome, plantar fasciitis, and Achilles tendonitis. This embodiment extends to a method for treating chronic gastrointestinal inflammation such as inflammatory bowel disease, or "IBD," which refers to any of a variety of diseases characterized by inflammation of all or part of the intestines. Examples of inflammatory bowel disease include, but are not limited to, Crohn's disease, Barrett's syndrome, ileitis, irritable bowel syndrome, irritable colon syndrome, ulcerative colitis, pseudomembranous colitis, hemorrhagic colitis, hemolytic-uremic syndrome colitis, collagenous colitis, ischemic colitis, radiation colitis, drug and chemically induced colitis, diversion colitis, colitis in conditions such as chronic granulomatous disease, celiac disease, celiac sprue, gastritis, and enterocolitis.

A further embodiment of the invention pertains to weight management, including the promotion of weight loss in a subject by reducing appetite and/or effecting metabolic changes. The method includes administering an effective amount of a CBN analog of the invention to a subject who could benefit from losing weight, e.g., a subject who is overweight or obese. Also provided are methods for treating conditions caused by or associated with excess weight or obesity, where the conditions include type 2 diabetes; insulin resistance; impaired glucose tolerance; gallbladder disease; dyslipidemia, e.g., high cholesterol, elevated triglyceride levels, and/or elevated levels of low-density lipoprotein (LDL); gout; hypertension; and metabolic disorders such as Metabolic Syndrome (Syndrome X, including insulin-resistant Syndrome X), individual conditions associated with metabolic syndrome, and hypoalphalipoproteinemia.

In any of the foregoing methods, the CBN analog can be administered to the subject as a monotherapy, or it may be co-administered with at least one additional active agent in a combination therapy, in which case the CBN analog and the additional active agent(s) may be administered simultaneously or sequentially, and, if administered simultaneously, may be administered in a single dosage form or in separate dosage forms. Any additional active agent that is co-administered with the CBN analog will generally, although not necessarily, be selected for its utility in treating the same indication as the CBN analog.

In the present method for treating pain, for example, suitable secondary active agents are also, preferably, analgesic agents, and may be, by way of example, a nonsteroidal anti-inflammatory agent (NSAID) (e.g., ketoprofen, flurbiprofen, ibuprofen, naproxen, fenoprofen, benoxaprofen, indoprofen, pirprofen, carprofen, oxaprozin, pranoprofen, suprofen, alminoprofen, butibufen, fenbufen, apazone, diclofenac, difenpiramide, diflunisal, etodolac, indomethacin, ketorolac, meclofenamate, nabumetone, phenylbutazone, piroxicam, sulindac, tolmetin, etc.), a steroidal anti-inflammatory agent (e.g., hydrocortisone, hydrocortisone-21-monoesters such as hydrocortisone-21-acetate, hydrocortisone-21 butyrate, hydrocortisone-21-propionate, hydrocortisone-21-valerate); hydrocortisone-17,21-diesters such as hydrocortisone-17,21-diacetate, hydrocortisone-17-acetate-21-butyrate, hydrocortisone-17,21-dibutyrate); alclometasone, dexamethasone, flumethasone, prednisolone, methylprednisolone, etc.), a non-opioid analgesic agent (e.g., acetaminophen, apazone, etodolac, difenpiramide, indomethacin, meclofenamate, mefenamic acid, oxaprozin, phenylbutazone, piroxicam, tolmetin, etc.), an opioid analgesic agent (e.g., alfentanil, buprenorphine, butorphanol, codeine, dihydrocodeine, fentanyl, hydrocodone, hydromorphone, levorphanol, meperidine, methadone, morphine, nalbuphine, oxycodone, oxymorphone, pentazocine, propoxyphene, sufentanil, tramadol, etc.), or the like.

Co-administration of a CBN analog as provided herein with an opioid analgesic agent is of particular interest insofar as a combination formulation, or separate co-administration, will reduce the therapeutic dosage of the opioid required and eliminate or at least minimize many of the undesirable side effects associated with opioid use, such as sedation, dizziness, tolerance, physical dependence, and the like. See Nielsen et al. (2017), "Opioid-Sparing Effect of Cannabinoids" A Systematic Review and Meta-Analysis," Neuropsychopharmacology 42(9): 1752-1765, which indicates that the median effective dose (ED50) of morphine administered in combination with Δ9-THC is 3.6 times lower than the ED50 of morphine alone. Co-administration of a CBN analog with an opioid analgesic can also exhibit synergistic activity, with increased analgesic efficacy and/or reduced side effects seen relative to either drug administered as a monotherapy. Accordingly, in some embodiments, the invention provides a method for reducing the therapeutic dosage of an opioid administered to a subject to treat pain, and/or eliminating or at least minimizing side effects of opioid administration, wherein the method involves co-administering a CBN analog of the invention to the subject in combination with the opioid, either simultaneously or sequentially.

Secondary active agents for co-administration with the CBN analog in the treatment of inflammatory conditions include, by way of example, non-steroidal anti-inflammatory agents (NSAIDs), including those identified above as suitable in the treatment of pain; acetylsalicylic acid; apazone; diclofenac; difenpiramide; diflunisal; etodolac; flufenamic acid; indomethacin; ketorolac; meclofenamate; mefenamic acid; nabumetone; phenylbutazone; piroxicam; salicylic acid; sulindac; tolmetin; oxicams such as meloxicam and piroxicam; nabumetone; phenylbutazone; piroxicam; salicylates such as salsalate and acetylsalicylic acid; sulfasalazine; sulindac; tolmetin; and COX-2 inhibitors such as celecoxib, rofecoxib, and valdecoxib. The secondary active agent may also be selected from steroidal anti-inflammatory agents, including corticosteroids such as hydrocortisone, hydrocortisone-21-monoesters (e.g., hydrocortisone-21-acetate, hydrocortisone-21-butyrate, hydrocortisone-21-propionate, hydrocortisone-21-valerate, etc.), hydrocortisone-17,21-diesters (e.g., hydrocortisone-17,21-diacetate, hydrocortisone-17-acetate-21-butyrate, hydrocortisone-17,21-dibutyrate, etc.), alclometasone, dexamethasone, flumethasone, prednisolone, and methylprednisolone.

Secondary active agents for co-administration with the CBN analog in the method for managing weight loss and treating related conditions (overweight, obesity, type 2 diabetes, metabolic syndrome, and the like, as detailed above) include glucagon-like peptide 1 receptor agonists (GLP-1 RAs), which have become popular in the treatment of obesity and related conditions because they lower both hemoglobin A1C and weight while exhibiting a very low risk of hypoglycemia; some GLP-1 RAs also have documented cardiovascular benefits. Examples of GLP-1 RAs that can be beneficially administered in a combined dosage regimen with a CBN analog of the invention include exenatide, liraglutide, albiglutide, dulaglutide, lixisenatide, semaglutide, and tirzepatide. In one embodiment, the method involves administration of a CBN analog of the invention at the beginning of an ongoing dosage regimen, e.g., during the first week, two weeks, three weeks, two months, three months, six months, with addition of the selected GLP-1 RA at a later point in the dosage regimen, e.g., after the first week, after the first two weeks, three weeks, two months, three months, six months, etc. The unit dosage and daily dosage of the CBN analog are as described earlier herein, and the unit dosage and daily dosage of the GLP-1 RA are amounts within the approved dosage range for the selected GLP-1 RA. The combined dosing is continued until the desired end result is achieved, e.g., a significant reduction in weight, lowered hemoglobin A1C, lowered blood pressure, or the like.

Secondary active agents to administer with a CBN analog of the invention for the treatment of endometriosis include, without limitation, progesterone or another naturally occurring, synthetic, or semi-synthetic progestogen (the latter two generally referred to as "progestins"), such as desogestrel, ethisterone, etonorgestrel, hydroxyprogesterone (or esters thereof), medroxyprogesterone (or esters thereof), megestrol, and the like; hormonal contraceptives in which a progestogen is combined with an estrogenic compound such as estradiol (i.e., 17β-estradiol) or an ester thereof, estrone, ethinylestradiol, etc., as may be administered in the form of a birth control pill, a transdermal patches, an IUD, or the like; and GnRH antagonists (e.g., elagolix and linzagolix) and GnRH agonists (e.g., triptorelin, leuprorelin, buserelin, etc.). Examples of other secondary active agents that may be beneficial to co-administer with a CBN analog of the invention for the treatment of endometriosis include aromatase inhibitors (e.g., letrozole and anastrozole); NSAIDs such as those identified above as secondary agents to co-administer with a CBN analog in the treatment of pain and inflammatory conditions; and analgesic agents, including both non-opiate analgesic agents and opiate analgesic agents such as those mentioned above for the treatment of pain.

Also of interest are combinations comprising at least one CBN analog of the invention and a second beneficial agent in the form of a nutritional supplement, where the nutritional supplement, in one embodiment, is selected from vitamins, vitamin metabolites, vitamin derivatives, provitamins, and vitamin cofactors, e.g., vitamin $A_1$ (all-trans-retinol), vitamin A aldehyde (retinal), retinoic acid, provitamin A carotenoids (alpha-carotene, beta-carotene, gamma-carotene), xanthophyll beta-cryptoxanthin), vitamin $B_1$ (thiamine), thiamine monophosphate, thiamine pyrophosphate, riboflavin (vitamin $B_2$), flavin mononucleotide (FMN), flavin adenine dinucleotide (FAD), niacin (vitamin $B_3$), niacinamide, nicotinamide riboside, nicotinamide adenine dinucleotide phosphate (NADP), pantothenic acid (vitamin $B_5$), pantothenol, pantethine, pyridoxine (vitamin $B_6$), pyridoxal, pyridoxal phosphate, pyridoxamine, biotin (vitamin $B_7$), folate (vitamin $B_9$), folic acid, tetrahydrofolic acid, cobalamin (vitamin $B_{12}$), methylcobalamin, hydroxocobalamin (vitamin $B_{12a}$), adenosylcobalamin, cyanocobalamin, ascorbic acid (vitamin C), calciferols (vitamin D) including vitamin $D_1$ (a 1:1 mixture of ergocalciferol and lumisterol), ergocalciferol (vitamin $D_2$), cholecalciferol (vitamin $D_3$), vitamin E (alpha-tocopherol, beta-tocopherol, gamma-tocopherol, delta-tocopherol, tocopheryl acetate, alpha-tocotrienol, beta-tocotrienol, gamma-tocotrienol, and delta-tocotrienol), vitamin $K_1$ (phylloquinone), vitamin $K_2$ (menaquinone), choline, carnitine, coenzyme A, and coenzyme Q10.

In another embodiment, the nutritional supplement is a mineral, i.e., an inorganic substance that is required in the human diet, including, without limitation, calcium, magnesium, iron, zinc, selenium, copper, manganese, chromium, molybdenum, etc.

In still another embodiment, the nutritional supplement may be selected from amino acids, peptides, proteins, hormones, probiotics, fatty acids and other lipids, anti-oxidants, essential oils, fiber supplements, herbal supplements, botanicals, plant extracts, and the like, with specific such supplements including, for example, terpenoids, curcumin, resveratrol, lignans, carnosine, chondroitin sulfate, creatine, dehydroepiandrosterone, 5-hydroxytryptophan, collagen, indole-3-carbinol, methylsulfonylmethane, phospholipids, phytosterols, essential fatty acids (e.g., omega-3 fatty acids), green tea polyphenols, quercetin and other flavonoids, S-adenosylmethionine, and theobromine, among others. Further examples of suitable nutrients include those listed in Handbook of Nutraceuticals and Functional Foods, Robert E. C. Wildman, Ed., CRC Press (2001).

It is to be understood that while the invention has been described in conjunction with a number of specific embodiments, the foregoing description as well as the examples that follow are intended to illustrate and not limit the scope of the invention.

All patents, patent publications, literature references, and other materials cited herein are incorporated by reference in their entireties.

EXPERIMENTAL

Compounds (INT-8) and (INT-9), which serve as starting materials in Examples 1-3 below, were synthesized according to Scheme 3:

Scheme 3

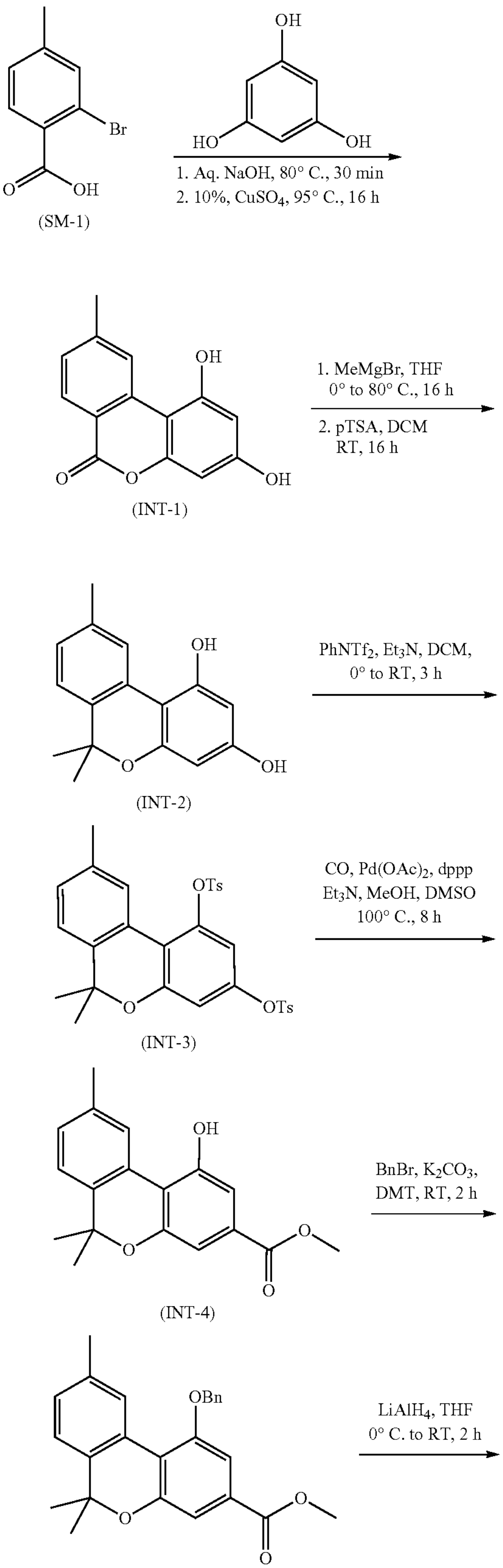

(SM-1) (INT-1) (INT-2) (INT-3) (INT-4) (INT-5)

-continued

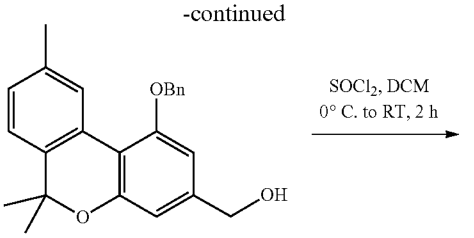

(INT-6)

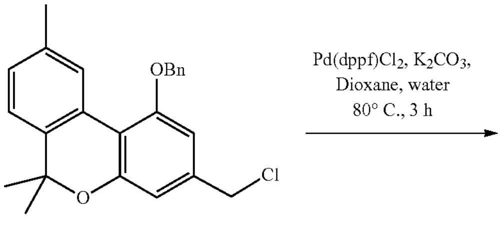

(INT-7)

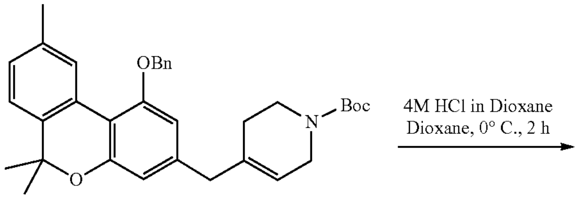

(INT-8)

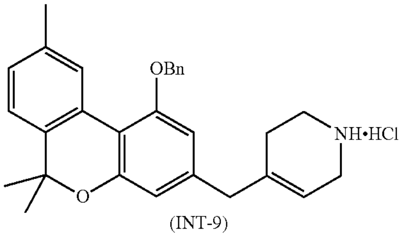

(INT-9)

Step 1: Synthesis of 1,3-dihydroxy-9-methyl-6H-benzo[c]chromen-6-one (INT-1)

To a stirred solution of 2-bromo-4-methylbenzoic acid (SM-1) (100.0 g, 465.0 mmol) in 0.4M NaOH solution (2.4 L, 24.0 vol.) was added CAS: 108-73-6 (70.2 g, 558.0 mmol) at room temperature and the reaction mixture was heated at 80° C. After 30 min, aqueous 10% copper sulphate (40.0 mL, 0.4 vol.) solution was added dropwise to the reaction mixture at the same temperature and the reaction mixture further heated at 95° C. for 16 h. Progress of the reaction was monitored by TLC and LCMS analysis. After completion of the reaction, the reaction mixture was cooled to room temperature and resulting precipitate was filtered, washed with water (1000.0 mL). The obtained solid material was dried over reduced pressure to obtain the title intermediate 1,3-dihydroxy-9-methyl-6H-benzo[c]chromen-6-one (INT-1) (75.0 g, 66.58%) as a creamy solid.

LCMS: 92.94%, RT: 1.943 min.@254 nm & @98.28%, RT:1.943 min @220 nm, m/z 243.1 (M+1).

1H NMR (400 MHz, DMSO-$d^6$): δ 10.84 (s, 1H), 10.13 (s, 1H), 8.76 (s, 1H), 8.05 (d, J=8.0 Hz, 1H), 7.29 (d, J=8.4 Hz, 1H), 6.31 (d, J=2.0 Hz, 1H), 6.24 (d, J=2.0 Hz, 1H), 2.44 (s, 3H).

Step 2: Synthesis of 6,6,9-trimethyl-6H-benzo[c]chromene-1,3-diol (INT-2)

To a stirred solution of 1,3-dihydroxy-9-methyl-6H-benzo[c]chromen-6-one (INT-1) (75.0 g, 309.9 mmol) in THE (1500.0 mL, 20.0 vol.) was added 3.0M methyl magnesium bromide in diethyl ether (560.0 mL, 170 mmol) drop wise at 0° C. The reaction mixture was gradually warmed to room temperature and further heated at 80° C. for 16h. Progress of the reaction was monitored by TLC and LCMS. After completion of the reaction, the reaction mixture was cooled to room temperature, quench with sat. $NH_4Cl$ solution (500.0 mL), Adjust to pH 3-4 with 6N HCl and extracted with EtOAc (2×500.0 mL). The organic layers were combined, dried over Sodium sulphate and concentrated under reduced pressure to obtain crude material. The crude material (weight of crude: 860.0 g) was taken in DCM (750.0 mL, 10 vol.) and pTSA (11.7 g, 61.9 mmol) was added at room temperature. The reaction mixture further stirred at room temperature for 16h. Progress of the reaction was monitored by TLC and LCMS analysis. After completion of reaction, the reaction mixture was quench by water (500.0 mL) and extracted with DCM (2×500.0 mL). The organic layers were combined, dried over Sodium sulphate and concentrated under reduced pressure to obtain the crude material. The crude material was purified by normal phase column chromatography by using MeOH in DCM as eluent to obtain pure title intermediate 6,6,9-trimethyl-6H-benzo[c]chromene-1,3-diol (INT-2) (60.0 g, 75.61%) as off white solid.

LCMS: 97.63%, RT: 2.167 min.@288 nm & 97.89%, RT: 2.167 min.@220 nm, m/z 257.2 (M+1).

1H NMR (400 MHz, DMSO-$d^6$): δ 9.87 (s, 1H), 9.44 (s, 1H), 8.17 (s, 1H), 7.12 (d, J=7.6 Hz, 1H), 6.96 (d, J=8.0 Hz, 1H), 6.05 (d, J=2.4 Hz, 1H), 5.80 (d, J=2.4 Hz, 1H), 2.28 (s, 3H), 1.47 (s, 6H).

Step 3: Synthesis of 1-hydroxy-6,6,9-trimethyl-6H-benzo[c]chromen-3-yl trifluoromethane sulfonate (INT-3)

To a stirred solution of 6,6,9-trimethyl-6H-benzo[c]chromene-1,3-diol (INT-2) (60.0 g, 234.2 mmol) in DCM (900.0 mL, 10 vol.) was added TEA (71.13 gm, 703.1.0 mmol) at 0° C. and the solution was stirred at same temperature for 15 min. After 15 min, $PhNTf_2$ (83.67 g, 244.3 mmol) was added to the reaction mixture portion-wise and the reaction mixture was warmed to room temperature. The reaction mixture was stirred at room temperature for 3h. Progress of the reaction was monitored by TLC. After completion of reaction, the reaction mixture was quench by water (500.0 mL) and extracted with DCM (2×500 mL). The combined organic layer was dried over sodium sulphate and concentrated to obtain the crude material. The crude material was purified by normal phase column chromatography using EtOAc in Hexane as eluent to obtain pure title intermediate 1-hydroxy-6,6,9-trimethyl-6H-benzo[c]chromen-3-yl trifluoromethanesulfonate (INT-3) (49.0 g, 53.59%) as off white solid.

LCMS: 95.01%, RT: 2.760 min.@254 nm & 83.37%, RT: 2.766 min.@220 nm, m/z 775.5 (2M−1).

1H NMR (400 MHz, DMSO-$d^6$): δ 10.95 (s, 1H), 8.29 (s, 1H), 7.24 (d, J=8.0 Hz, 1H), 7.14 (dd, J=1.2 Hz, J=7.6 Hz, 1H), 6.63 (d, J=2.8 Hz, 1H), 6.53 (d, J=2.4 Hz, 1H), 2.32 (s, 3H), 1.53 (s, 6H).

Step 4: Synthesis of methyl 1-hydroxy-6,6,9-trimethyl-6H-benzo[c]chromene-3-carboxylate (INT-4)

To a stirred solution of 1-hydroxy-6,6,9-trimethyl-6H-benzo[c]chromen-3-yl trifluoromethanesulfonate (INT-3) (25.0 g, 64.4 mmol) in MeOH (500.0 mL, 20 vol.) and DMSO (500.0 mL, 20 vol.) in autoclave were added TEA (54.17 g, 53.4 mmol) and dppp (5.3 g, 12.8 mmol) at room temperature. The reaction mixture was purged with argon gas for 15 min and $Pd(OAc)_2$ (1.44 g, 6.44 mmol) was added to the reaction mixture at room temperature. The reaction mixture was further stirred under CO pressure (300 psi) at 110° C. for 8h. Progress of the reaction was monitored by TLC. After completion of reaction, the reaction mixture was. quench with sat. $NH_4Cl$ (500.0 mL) and extracted with EtOAc (2×400.0 mL). The organic layers were combined, dried over Sodium sulphate and concentrated get crude material. The crude material was purified by normal phase column chromatography by using EtOAc in hexane as eluent to obtain pure title intermediate methyl 1-hydroxy-6,6,9-trimethyl-6H-benzo[c]chromene-3-carboxylate (INT-4) (34.0 g, 90.32%) as off white solid.

LCMS: 99.01%, RT: 2.60 min.@210.0 nm & 98.6%, RT: 2.604 min.@280 nm, m/z 299.3 (M+1).

1H NMR (400 MHz, DMSO-$d^6$): δ 10.52 (s, 1H), 8.36 (s, 1H), 7.21-7.25 (m, 2H), 7.14-7.16 (m, 1H), 6.93 (d, J=2.0 Hz, 1H), 3.82 (s, 3H), 2.32 (s, 3H), 1.52 (s, 6H).

Step 5: Synthesis of methyl 1-(benzyloxy)-6,6,9-trimethyl-6H-benzo[c]chromene-3-carboxylate (INT-5)

To a stirred solution of methyl 1-hydroxy-6,6,9-trimethyl-6H-benzo[c]chromene-3-carboxylate (INT-4) (34 0.0 g, 113.9 mmol, 1.0 eq.) in DMF (340.0 ml, 10.0 vol.) were added $K_2CO_3$(39.3 g, 285.3 mol, 2.5 eq.) followed by benzyl bromide (13.5 ml, 113.9 mmol, 1.0 eq.) drop wise at room temperature. The reaction mixture was allowed to stir at room temperature for 2h. Progress of the reaction was monitored by TLC. After completion of the reaction, the reaction mixture was diluted by water (400.0 ml) and extracted with EtOAc (2×300.0 ml). The organic layers were combined, dried over sodium sulphate and concentrated under reduced pressure to get the crude material. The crude material was purified by column chromatography to obtain pure title intermediate (INT-5) (40.0 g, 90.35%) as white solid.

LCMS: 99.26%, RT: 3.177 min.@310 nm, m/z 389.5 (M+1).

1H NMR (400 MHz, DMSO-$d^6$): δ 8.29 (s, 1H), 7.58 (d, J=7.6 Hz, 2H), 7.37-7.47 (m, 4H), 7.26 (d, J=8.0 Hz, 1H), 7.14-7.17 (m, 2H), 5.32 (s, 2H), 3.86 (s, 3H), 2.19 (s, 3H), 1.53 (s, 6H).

Step 6: Synthesis of (1-(benzyloxy)-6,6,9-trimethyl-6H-benzo[c]chromen-3-yl) methanol (INT-6)

To a stirred solution of 1-(benzyloxy)-6,6,9-trimethyl-6H-benzo[c]chromene-3-carboxylate (INT-5) (40.0 g, 0 103.2 mmol, 1.0 eq.) in THE (400.0 mL, 10.0 vol.) was added $LiAlH_4$ (154.6 mL, 1M in THF, 154.6 mmol, 1.5 eq.) drop wise at 0° C. The reaction mixture was allowed to stir at same temperature for 2h. Progress of the reaction was monitored by TLC. After completion of the reaction, the reaction mixture was quenched by sat. $NaHCO_3$ solution (350.0 ml.) and extracted with EtOAc (2×300.0 ml). The organic layers were combined, dried over sodium sulphate and concentrated under reduced pressure to get the crude material. The crude material was purified by column chromatography to obtain pure title intermediate (INT-6) (34.0 g, 91.61%) as white solid.

LCMS: 98.54%, RT: 2.700 min.@210 nm, m/z 361.3 (M+1).

$^1$H NMR (400 MHz, DMSO-$d^6$): δ 8.24 (s, 1H), 7.57 (d, J=7.2 Hz, 2H), 7.38-7.47 (m, 3H), 7.20 (d, J=8.0 Hz, 1H), 7.06 (d, J=8.0 Hz, 1H), 6.84 (s, 1H), 6.57 (s, 1H), 5.27 (t, J=5.6 Hz, 1H), 5.22 (s, 2H), 4.48 (d, J=6.0 Hz, 2H), 2.17 (s, 3H), 1.51 (s, 6H).

Step 7: Synthesis of 1-(benzyloxy)-3-(chloromethyl)-6,6,9-trimethyl-6H-benzo[c]chromene (INT-7)

To a stirred solution of (1-(benzyloxy)-6,6,9-trimethyl-6H-benzo[c]chromen-3-yl) methanol (INT-6) (34.0 g, 94.40 mmol, 1.0 eq.) in DCM (340.0 mL, 10.0 vol.) was added $SOCl_2$ (68.0 mL, 2.0 vol.) drop wise at 0° C. The reaction mixture was further allowed to stir at room temperature for 2h. Progress of the reaction was monitored by TLC. After completion of reaction, the reaction mixture was quenched with sat. $NaHCO_3$ (500.0 ml) and extracted with DCM (2×500.0 mL). The organic layers were combined, dried over sodium sulphate and concentrated under reduced pressure to get the crude material. The crude material was triturated by n-pentane (300.0 ml) to obtain pure title intermediate (INT-7) (31.0 g, 86%) as yellow solid.

$^1$H NMR (400 MHz, DMSO-$d^6$): δ 8.23 (s, 1H), 7.58 (d, J=7.2 Hz, 2H), 7.36-7.47 (m, 3H), 7.21 (d, J=7.6 Hz, 1H), 7.08 (d, J=7.6 Hz, 1H), 6.98 (s, 1H), 6.69 (s, 1H), 5.24 (s, 2H), 4.72 (s, 2H), 2.17 (s, 3H), 1.51 (s, 6H).

Step 8: Synthesis of tert-butyl 4-((1-(benzyloxy)-6,6,9-trimethyl-6H-benzo[c]chromen-3-yl)methyl)-3,6-dihydropyridine-1(2H)-carboxylate (INT-8)

To a stirred solution of 1-(benzyloxy)-3-(chloromethyl)-6,6,9-trimethyl-6H-benzo[c]chromene (INT-7) (30.0 g, 79.176 mmol., 1.0 eq.) in dioxane (300.0 ml, 10.0 vol.) and water (150.0 mL, 5.0 vol.) were added $K_2CO_3$ (32.77 g, 237.53 mmol., 3.0 eq.) at room temperature followed by tert-butyl 4-(4,4,5,5-tetramethyl-1,3,2-dioxaborolan-2-yl)-3,6-dihydropyridine-1(2H)-carboxylate (CAS: 286961-14-6) (26.91 g, 87.094 mmol., 1.1 eq.). The reaction mixture was degassed with $N_2$ gas for 10 min and $Pd(dppf)Cl_2$ (5.793 g, 7.9176 mmol, 0.1 eq.) was added to the reaction mixture at room temperature. The reaction mixture was allowed to stir at same temperature for 10 min and further heated to 80° C. for 3h. Progress of the reaction was monitored by TLC. After completion of reaction, the reaction mixture was diluted by water (200.0 ml) and extracted with EtOAc (2×200 ml). The organic layers were combined, dried over sodium sulphate and concentrated under reduced pressure to get the crude material. The crude material was purified by column chromatography (product eluted at 20% EtOAc in hexane) to obtain the pure title intermediate (INT-8) (23.0 g, 55.26%) as a pale-yellow solid.

LCMS: 100%, RT: 3.484 min.@220 nm & @230 nm m/z: 470.4 (M−56), 526.4 (M+1).

$^1$H NMR (400 MHz, DMSO-$d^6$): δ 8.23 (s, 1H), 7.55 (d, J=8.0 Hz, 2H), 7.36-7.45 (m, 3H), 7.19 (d, J=8.0 Hz, 1H), 7.05 (d, J=7.6 Hz, 1H), 6.66 (s, 1H), 6.40 (s, 1H), 5.48 (s, 1H), 5.22 (s, 2H), 3.81-3.86 (m, 3H), 3.34 (s, 2H), 3.25 (s, 2H), 2.18 (s, 3H), 2.07 (bs, 1H), 1.92 (bs, 2H), 1.50 (s, 6H), 1.17 (s, 9H).

Step 9: Synthesis of (4-((1-(benzyloxy)-6,6,9-trimethyl-6H-benzo[c]chromen-3-yl)methyl)-1,2,3,6-tetrahydropyridine (INT-9)

To a stirred solution of tert-butyl 4-((1-(benzyloxy)-6,6,9-trimethyl-6H-benzo[c]chromen-3-yl)methyl)-3,6-dihydropyridine-1(2H)-carboxylate (INT-8) (23.0 g, 43.752 mmol., 1.0 eq.) in Dioxane (115.0 mL, 5.0 vol.) was added 4M HCl in dioxane (115 mL, 5.0 vol.) at 0° C. The reaction mixture was allowed to stir at same temperature for 2h. Progress of the reaction was monitored by TLC. After completion of reaction, the reaction mixture was concentrated under reduced pressure to obtain the residue. The residue was triturated with diethyl ether and n-pentane to obtain pure title intermediate (INT-9) (20.0 g, Quantitative, HCl salt) as yellow solid.

LCMS: 99.42%, RT: 2.347 min.@285 nm, m/z: 426.4 (M+1).

Example 1

Synthesis of 2,2-Difluoro-1-(4-((1-hydroxy-6,6,9-trimethyl-6H-benzo[c]chromen-3-yl)methyl)piperidin-1-yl) ethan-1-one (1)

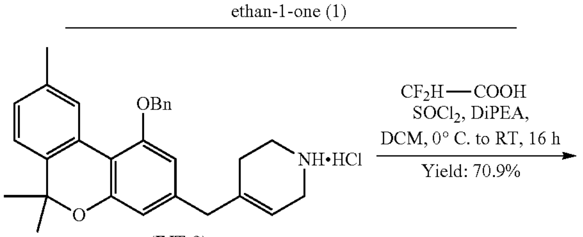

(INT-9)

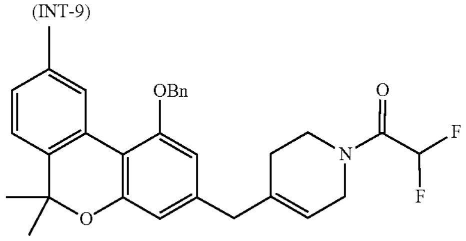

(INT-11)

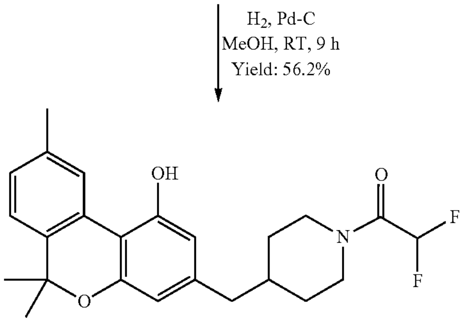

(1)

2,2-difluoro-1-(4-((1-hydroxy-6,6,9-trimethyl-6H-benzo [c]chromen-3-yl)methyl)piperidin-1-yl)ethan-1-one (1) was synthesized according to Scheme 4, as follows:

(a) Compound (INT-9) was synthesized as illustrated in Scheme 3, above, and as described in detail thereafter.

(b) Synthesis of 1-(4-((1-(benzyloxy)-6,6,9-trimethyl-6H-benzo[c]chromen-3-yl)methyl)-3,6-dihydropyridin-1 (2H)-yl)-2,2-difluoroethan-1-one (INT-11):

To a stirred solution of 2,2-difluoroacetic acid (CAS: 381-73-7) (6.7 g, 4.4 mL, 70.493 mmol, 3.0 eq.) in DCM (67.0 mL, 10.0 vol.) was added $SOCl_2$ (13.9 g, 8.5 mL, 117.48 mmol, 5.0 eq.) at 0° C. The reaction mixture was gradually warmed to room temperature and stirred for 2h. Progress of the reaction was monitored by TLC. After completion of reaction, the reaction mixture was added to a previously stirred solution of (4-((1-(benzyloxy)-6,6,9-trimethyl-6H-benzo[c]chromen-3-yl)methyl)-1,2,3,6-tetrahydropyridine (INT-9) (10 g, 23.497 mmol., 1.0 eq.) in DCM (100.0 mL, 10.0 vol.) followed by N,N-diisopropylethylamine (DiPEA) (9.09 g, 12.2 mL, 70.491 mmol., 3.0 eq.) at room temperature. The reaction mixture was further stirred at the same temperature for an additional 16 h. After completion of the reaction, the reaction mixture was diluted with cold water (150.0 ml) and extracted with EtOAc (2×200.0 mL). The organic layers were combined, dried over sodium sulphate and concentrated under reduced pressure to obtain the crude material. The crude material was purified by column chromatography to give the pure title compound (INT-11) (8.4 g, 70.99%) as a white solid.

LCMS: 77.59%, RT: 2.981 min.@254 nm, 93.97% @220.0 nm, m/z: 504.4 (M+1), 521.4 (M+18).

(c) Synthesis of 2,2-difluoro-1-(4-((1-hydroxy-6,6,9-trimethyl-6H-benzo[c]chromen-3-yl)methyl)piperidin-1-yl)ethan-1-one (1).

To a stirred solution of 1-(4-((1-(benzyloxy)-6,6,9-trimethyl-6H-benzo[c]chromen-3-yl)methyl)-3,6-dihydropyridin-1(2H)-yl)-2,2-difluoroethan-1-one (INT-11) (8.4 g, 16.68 mmol., 1.0 eq.) in methanol (84 mL, 20.0 vol.) was added 10% Pd/C (6.2 g, 75% W/W) at room temperature. The reaction mixture was allowed to stir under an $H_2$ gas atmosphere at room temperature for 9h. Progress of the reaction was monitored by TLC. After completion of the reaction, the reaction mixture was filtered through a celite bed and the filtrate was concentrated under reduced pressure to obtain the crude material. The crude material was purified by column chromatography to give the pure title compound (1) (3.9 g, 56.27%) as a light pink solid.

LCMS: 100%, RT: 2.477 min.@220 nm & @285 nm & m/z: 416.3 (M+1), 438.3 (M+18).

HPLC: 96.45%, RT: 9.177 min.@210 nm.

$^1$H NMR (400 MHz, DMSO-d6): δ 9.93 (s, 1H), 8.26 (s, 1H), 7.17 (d, J=8.0 Hz, 1H), 7.03 (dd, J=1.2 Hz, J=6.8 Hz, 1H), 6.70 (t, HCF2, 1H), 6.36 (d, J=1.2 Hz, 1H), 6.23 (d, J=1.2 Hz, 1H), 4.25-4.28 (m, 1H), 3.82-3.86 (m, 1H), 3.04 (t, J=12.0 Hz, 1H), 2.64-2.70 (m, 1H), 2.38 (d, J=7.2 Hz, 2H), 2.30 (s, 3H), 1.64-1.81 (m, 3H), 1.47 (d, J=3.6 Hz, 6H), 1.07-1.17 (m, 2H).

Example 2

Synthesis of 1-(4-((1-(Benzyloxy)-6,6,9-trimethyl-6H-benzpo[c]chromen-3-yl)methyl)-3,6-dihydropyridin-1(2H)-yl)ethan-1-one (2)

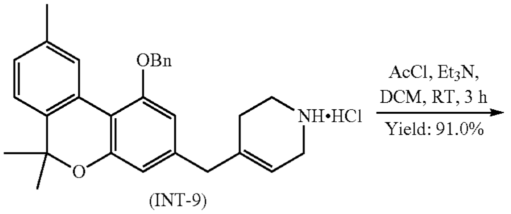

(INT-9)

-continued

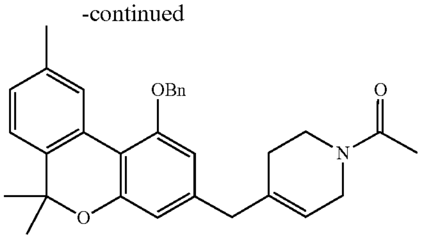

(INT-10)

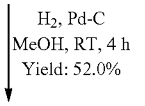

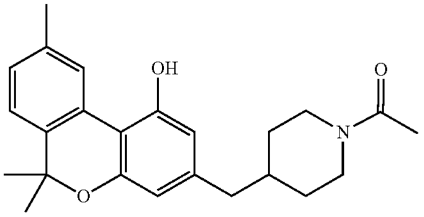

(2)

1-(4-((1-(benzyloxy)-6,6,9-trimethyl-6H-benzo[c]chromen-3-yl)methyl)-3,6-dihydropyridin-1(2H)-yl)ethan-1-one (2) was synthesized according to Scheme 5, as follows:

(a) Synthesis of Synthesis of 1-(4-((1-(benzyloxy)-6,6,9-trimethyl-6H-benzo[c]chromen-3-yl)methyl)-3,6-dihydropyridin-1(2H)-yl)ethan-1-one (INT-10):

To a stirred solution of 4-((1-(benzyloxy)-6,6,9-trimethyl-6H-benzo[c]chromen-3-yl)methyl)-1,2,3,6-tetrahydropyridine (INT-9) (9.0 g, 21.15 mmol., 1.0 eq.) in dichloromethane (DCM) (90.0 mL, 10.0 vol.) was added triethylamine (TEA) (9.7 mL, 69.78 mmol., 3.0 eq.) at room temperature. The reaction mixture was cooled to 0° C. and acetyl chloride (CAS: 75-36-5) (1.66 mL, 23.26 mmol., 1.1 eq.) was added dropwise to the reaction mixture. The reaction mixture was allowed to stir at room temperature for 3h. Progress of the reaction was monitored by TLC. After completion of the reaction, the reaction mixture was quenched with cold water (100.0 mL) and extracted with DCM (2×200.0 mL). The organic layers were combined, dried over sodium sulphate and concentrated under reduced pressure to yield the crude material (INT-10) (9.0 g, 91.01%) as a yellow sticky solid. LCMS: 90.63%, RT: 2.937 min. @220 nm, m/z: 468.4 (M+1), 935.5 (2M+1).

The crude material was directly used in the next step without further purification.

(b) Synthesis of 1-(4-((1-(benzyloxy)-6,6,9-trimethyl-6H-benzo[c]chromen-3-yl)methyl)-3,6-dihydropyridin-1(2H)-yl)ethan-1-one (2):

To a stirred solution of the 1-(4-((1-(benzyloxy)-6,6,9-trimethyl-6H-benzo[c]chromen-3-yl)methyl)-3,6-dihydropyridin-1(2H)-yl)ethan-1-one (INT-10) (9.0 g, 19.247 mmol., 1.0 eq.) obtained in the preceding step, in methanol (180 mL, 20.0 vol.), was added 10% Pd/C (6.3 g, 70% W/W) at room temperature. The reaction mixture was allowed to stir at RT for 3-4 h under $H_2$ gas atmosphere. Progress of the reaction was monitored by TLC. After completion of the reaction, the reaction mixture was filtered through a celite bed and the filtrate was concentrated under reduced pressure to obtain the crude material. The crude material was purified by column chromatography to obtain pure (2) (3.8 g, 52.03%) as white solid.

LCMS: 100%, RT: 2.453 min.@220 nm & @254 nm, m/z: 380.3 (M+1), 759.7 (2M+1). HPLC (HPLC-09, Waters™ Sunfire C18): 98.13%, RT: 8.51 min. @290 nm, 98.22% @254 nm.

$^1H$ NMR (400 MHz, DMSO-$d^6$): δ 9.93 (s, 1H), 8.27 (s, 1H), 7.17 (d, J=8.0 Hz, 1H), 7.04 (d, J=7.6 Hz, 1H), 6.37 (s, 1H), 6.23 (s, 1H), 4.33 (d, J=12.8 Hz, 1H), 3.77 (d, J=13.6 Hz, 1H), 2.94 (t, J=11.6 Hz, 1H), 2.36-2.50 (m, 3H), 2.30 (s, 3H), 1.99 (s, 3H), 1.53-1.74 (m, 3H), 1.49-1.50 (m, 6H), 0.92-1.19 (m, 3H).

Example 3

Synthesis of 4-((1-Hydroxy-6,6,9-trimethyl-6H-benzo[c]chromen-3-yl)methyl)morpholin-3-one (3)

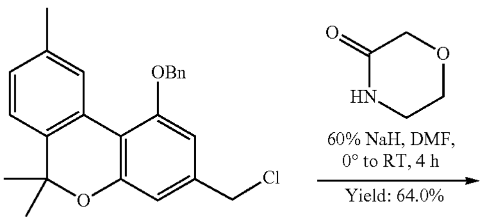

(INT-7)

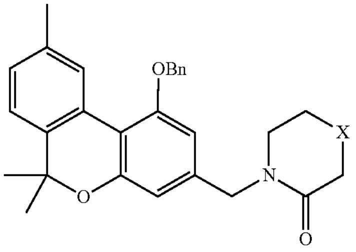

(INT-12)

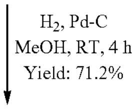

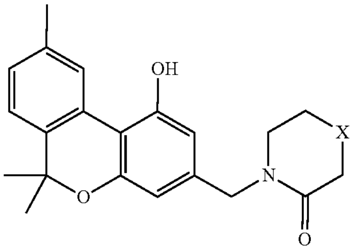

(3)

4-((1-Hydroxy-6,6,9-trimethyl-6H-benzo[c]chromen-3-yl)methyl)morpholin-3-one (3) was synthesized according to Scheme 6, as follows:

(a) Synthesis of 4-((1-(benzyloxy)-6,6,9-trimethyl-6H-benzo[c]chromen-3-yl)methyl) morpholin-3-one (INT-12):

To a stirred solution of 60% NaH (1.26 g, 23.75 mmol, 1.5 eq.) in DMF (240.0 mL, 30 vol.) was added 3-morpholinone (3.2 g, 31.66 mmol, 1.5 eq.) at 0° C. and the reaction mixture was stirred at same temperature for 15 min. After 15 min, a solution of 1-(benzyloxy)-3-(chloromethyl)-6,6,9-trimethyl-6H-benzo[c]chromene (INT-7) (8.0 g, 21.11 mmol, 1.0 eq.) was added dropwise to the reaction mixture at 0° C. and the reaction mixture was stirred at room temperature for 16h. Progress of the reaction was monitored by TLC. After completion of the reaction, the reaction mixture was quenched with cold water (100.0 mL) and extracted with EtOAc (2×200.0 mL). The organic layers were combined, dried over sodium sulphate and concentrated under reduced pressure to get the crude material. The crude material was purified by column chromatography to obtain the pure title compound (INT-12), 4-((1-(benzyloxy)-6,6,9-trimethyl-6H-benzo[c]chromen-3-yl)methyl)morpholin-3-one (6.52 g, 64.07%) as an off-white solid.

LCMS: 100%, RT: 2.739 min. @220 nm & @290 nm, m/z: 444.3 (M+1), 887.7 (2M+1).

$^1$H NMR (400 MHz, DMSO-d6): δ 8.22 (d, J=4.0 Hz, 1H), 7.55 (d, J=8.4 Hz, 2H), 7.36-7.45 (m, 3H), 7.19 (d, J=8.0 Hz, 1H), 7.06 (dd, J=1.2 Hz, J=8.0 Hz, 1H), 6.73 (d, J=1.2 Hz, 1H), 6.45 (d, J=1.2 Hz, 1H), 5.21 (s, 2H), 4.50 (s, 2H), 4.12 (s, 2H), 3.80 (t, J=4.8 Hz, 2H), 3.26 (t, J=5.6 Hz, 2H), 2.16 (s, 3H), 1.49 (s, 6H).

(c) Synthesis of 4-((1-hydroxy-6,6,9-trimethyl-6H-benzo[c]chromen-3-yl)methyl)morpholin-3-one (3):

To a stirred solution of 4-((1-(benzyloxy)-6,6,9-trimethyl-6H-benzo[c]chromen-3-yl)methyl)morpholin-3-one (INT-12) (6.52 g, 14.66 mmol) in MeOH (125.0 mL, 20.0 vol.) was added 10% Pd/C (4.8 g, 75% W/W) at room temperature. The reaction mixture was allowed to stir under an $H_2$ gas atmosphere at room temperature for 4h. Progress of the reaction was monitored by TLC. After completion of the reaction, the reaction mixture was filtered through a celite bed and the filtrate was concentrated under vacuum to obtain crude material. The crude material was purified by column chromatography to provide the pure title compound (3), 4-((1-hydroxy-6,6,9-trimethyl-6H-benzo[c]chromen-3-yl)methyl)morphoin-3-one (3.7 g, 71.22%), as an off-white solid.

LCMS: 98.02%, RT: 2.247 min.@210 nm, m/z: 354.3 (M+1), 707.6 (2M+1).

HPLC: 98.61%, RT: 7.709 min.@254 nm.

$^1$H NMR (400 MHz, DMSO-d6): δ 10.12 (s, 1H), 8.28 (d, J=0.8 Hz, 1H), 7.19 (d, J=7.6 Hz, 1H), 7.07 (dd, J=1.2 Hz, J=8.0 Hz, 1H), 6.47 (d, J=1.6 Hz, 1H), 6.30 (d, J=1.6 Hz, 1H), 4.42 (s, 2H), 4.13 (s, 2H), 3.83 (t, J=5.2 Hz, 2H), 3.27 (t, J=5.2 Hz, 2H), 2.31 (s, 3H), 1.50 (s, 6H).

Example 4

Synthesis of 3-(2-(1H-1,2,3-triazol-1-yl)ethyl)-6,6,9-trimethyl-6H-benzo[c]chromen-1-ol (54)

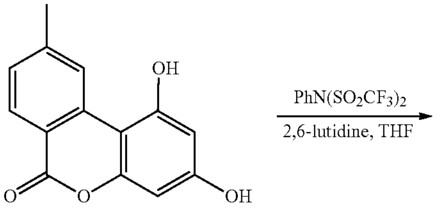

(INT-1)

-continued

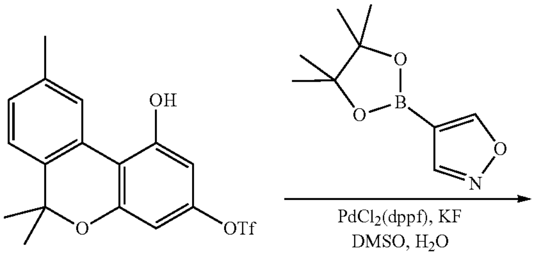

(INT-15)

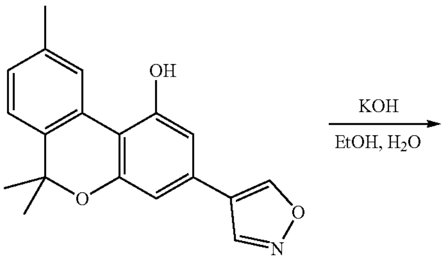

(INT-16)

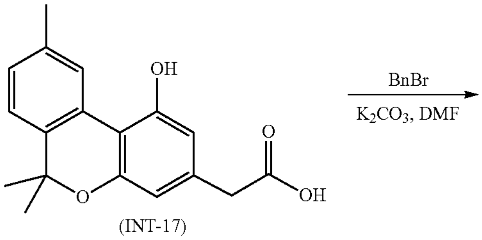

(INT-17)

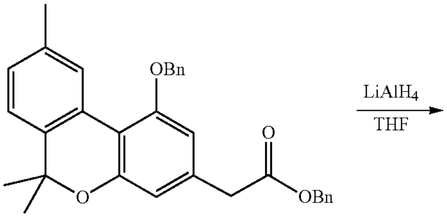

(INT-18)

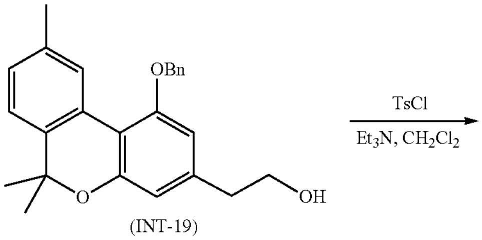

(INT-19)

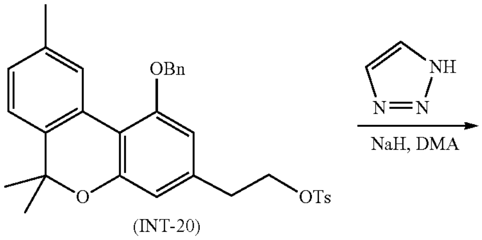

(INT-20)

-continued

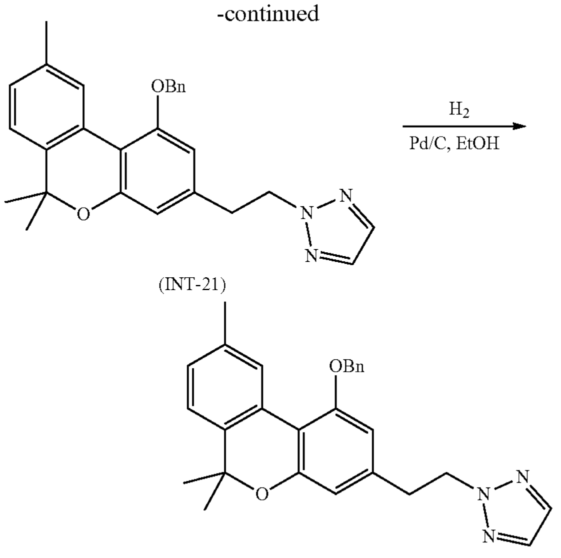

(INT-21)

(54)

3-(2-(1H-1,2,3-triazol-1-yl)ethyl)-6,6,9-trimethyl-6H-benzo[c]chromen-1-ol (54) was synthesized according to Scheme 7, as follows:

(a) Synthesis of 1-hydroxy-6,6,9-trimethyl-6H-benzo[c]chromen-3-yl trifluoro-methanesulfonate (INT-15):

To a stirred solution of 6,6,9-trimethyl-6H-benzo[c]chromene-1,3-diol (100 mg, 0.39 mmol), synthesized according to Scheme 3 and described in detail thereafter (INT-1) in tetrahydrofuran (10 mL) at 0° C. were added in single portions 1,1,1-trifluoro-N-phenyl-N-((trifluoromethyl)sulfonyl)methanesulfonamide (277 mg, 0.775 mmol) and 2,6-lutidine (0.091 mL, 0.78 mmol). The mixture was allowed to warm to room temperature and then was heated at 70° C. for 16 h. After this time, water (10 mL) was added, and the mixture was extracted with ethyl acetate (2×10 mL). The combined organic layers were dried over sodium sulfate, filtered and concentrated under reduced pressure. The residue obtained was purified by chromatography (silica gel; hexanes to 80:20 hexanes/ethyl acetate) to afford 1-hydroxy-6,6,9-trimethyl-6H-benzo[c]chromen-3-yl trifluoromethanesulfonate (INT-15, 110 mg, 72%) as an off-white solid.

$^1$H NMR (400 MHz, DMSO-d6): δ 10.94 (s, 1H), 8.29 (s, 1H), 7.23 (d, J=8.1 Hz, 1H), 7.13 (d, J=8.2 Hz, 1H), 6.64 (s, 1H), 6.52 (s, 1H), 2.33 (s, 3H), 1.53 (s, 6H).

(b) Synthesis of 3-(isoxazol-4-yl)-6,6,9-trimethyl-6H-benzo[c]chromen-1-ol (INT-16):

To a stirred solution of 1-hydroxy-6,6,9-trimethyl-6H-benzo[c]chromen-3-yl trifluoromethane-sulfonate (INT-15, 1.5 g, 3.9 mmol) in dimethyl sulfoxide (40 mL) was added 1 M potassium fluoride in water (0.67 g, 12 mmol) at room temperature. The mixture was degassed with argon for 10 min, and (1,1'-bis(diphenylphosphino)ferrocene)palladium (II) dichloride (0.28 g, 0.38 mmol) was added. The resulting reaction mixture was stirred at 110° C. for 16 h. After this time, the mixture was cooled, combined with water (3 mL), and extracted with ethyl acetate (3×6 mL). The combined organic extracts were dried over sodium sulfate, filtrated and concentrated under reduced pressure to afford a mixture of 3-(isoxazol-4-yl)-6,6,9-trimethyl-6H-benzo[c]chromen-1-ol (INT-16) as a brown gum which was used in the next step without purification.

(c): Synthesis of 2-(1-hydroxy-6,6,9-trimethyl-6H-benzo[c]chromen-3-yl)acetic acid (INT-17):

To a stirred solution of 3-(isoxazol-4-yl)-6,6,9-trimethyl-6H-benzo[c]chromen-1-ol (INT-16) (2.0 g, 6.5 mmol) in ethanol (20 mL) and water (20 mL) was added potassium hydroxide (2.91 g, 52.1 mmol) at room temperature, and the mixture was stirred at 100° C. for 16 h. After this time, water (20 mL) was added, and the mixture was washed with ethyl acetate (30 mL). The layers were separated, and the organic layer was discarded. The aqueous layer was acidified with 2 M hydrochloric acid and extracted with ethyl acetate (3×20 mL). The combined organic extracts were dried over sodium sulfate, filtrated and concentrated under reduced pressure to afford 2-(1-hydroxy-6,6,9-trimethyl-6H-benzo[c]chromen-3-yl)acetic acid (INT-17, 2.0 g) as a black oil that was used in the next step without further purification. MS (ESI) m/z 299 [M+H]+.

(d) Synthesis of benzyl 2-(1-(benzyloxy)-6,6,9-trimethyl-6H-benzo[c]chromen-3-yl)acetate (INT-18):

To a stirred solution of 2-(1-hydroxy-6,6,9-trimethyl-6H-benzo[c]chromen-3-yl)acetic acid (INT-17, 500 mg, 1.7 mmol) and potassium carbonate (1.39 g, 10.1 mmol) in N,N-dimethylformamide (5 mL) was added benzyl bromide (0.43 mL, 3.7 mmol) at room temperature. The mixture was stirred for 16 h. After this time, water (10 mL) was added and the mixture was extracted with ethyl acetate (2×15 mL). The combined organic extracts were washed with brine (10 mL), dried over sodium sulfate, filtered and concentrated under reduced pressure. The residue obtained was purified by chromatography (silica gel; hexanes to 90:10 hexanes/ethyl acetate) to afford benzyl 2-(1-(benzyloxy)-6,6,9-trimethyl-6H-benzo[c]chromen-3-yl)acetate (INT-18, 300 mg, 37%) as an off-white solid.

$^1$H NMR (400 MHz, DMSO-d6): δ 8.22 (d, J=0.8 Hz, 1H), 7.56 (t, J=6.8 Hz, 21H), 7.46-7.43 (m, 21H), 7.36 (d, J=4.4 Hz, 2H), 7.32-7.31 (m, 41H), 7.19 (d, J=7.8 Hz, 1H), 7.07 (dd, J=7.8, 1.2 Hz, 1H), 6.80 (d, J=1.6 Hz, 1H), 6.55 (d, J=1.2 Hz, 1H), 5.16 (d, J=1.2 Hz, 2H), 5.15 (d, J=2.0 Hz, 2H), 3.72 (s, 2H), 2.17 (s, 3H), 1.51 (s, 6H); MS (ESI) m/z 479 [M+H]+.

(e) Synthesis of 2-(1-(benzyloxy)-6,6,9-trimethyl-6H-benzo[c]chromen-3-yl)ethan-1-ol (INT-19):

To a stirred solution of benzyl 2-(1-(benzyloxy)-6,6,9-trimethyl-6H-benzo[c]chromen-3-yl)acetate (INT-18, 300 mg, 0.63 mmol) in tetrahydrofuran (5 mL) was added 2.0 M lithium aluminum hydride in tetrahydrofuran (0.62 mL, 1.24 mmol) dropwise at 0° C. The resultant mixture was stirred at room temperature for 4 h. After this time, solid sodium sulfate decahydrate was carefully added, the mixture was filtered through diatomaceous earth and the filter cake washed with ethyl acetate (50 mL). The filtrate was concentrated under reduced pressure and the residue obtained was purified by chromatography (silica gel; hexanes to 60:40 hexanes/ethyl acetate) to afford 2-(1-(benzyloxy)-6,6-dimethyl-6H-benzo[c]chromen-3-yl)ethan-1-ol (INT-19, 100 mg, 44%) as an off-white solid.

$^1$H NMR (400 MHz, DMSO-d6): δ 8.22 (d, J=0.8 Hz, 1H), 7.57 (t, J=7.2 Hz, 2H), 7.47-7.43 (m, 2H), 7.40-7.38 (m, 1H), 7.19 (d, J=8.0 Hz, 1H), 7.04 (dd, J=7.8, 0.8 Hz, 1H), 6.74 (d, J=1.2 Hz, 1H), 6.47 (d, J=1.2 Hz, 1H), 5.22 (s, 2H), 4.66 (t, J=5.2 Hz, 1H), 3.67-3.62 (m, 2H), 2.70 (t, J=7.2 Hz, 2H), 2.17 (s, 3H), 1.50 (s, 6H); MS (ESI) m/z 375 [M+H]+.

(f) Synthesis of 2-(1-(benzyloxy)-6,6,9-trimethyl-6H-benzo[c]chromen-3-yl)ethyl 4-methylbenzenesulfonate (INT-20):

To a stirred solution of 2-(1-(benzyloxy)-6,6,9-trimethyl-6H-benzo[c]chromen-3-yl)ethan-1-ol (INT-19, 300 mg, 0.80 mmol) and triethylamine (0.28 mL, 2.0 mmol) in dichloromethane (5 mL) was added tosyl chloride (305 mg, 1.60 mmol) at 0° C. The resultant mixture was allowed to warm to room temperature and stir for 1 h. After this time, water (10 mL) was added and the mixture was extracted with dichloromethane (2×15 mL). The combined organic extracts were washed with brine (10 mL), dried over sodium sulfate, .filtered and concentrated under reduced pressure to afford 2-(1-(benzyloxy)-6,6,9-trimethyl-6H-benzo[c]chromen-3-yl)ethyl 4-methylbenzene-sulfonate (INT-20, 300 mg) as a brown gum. This material was used in the next step without purification. MS (ESI) m/z 529 [M+H]+.

(g) 1-(2-(1-(benzyloxy)-6,6,9-trimethyl-6H-benzo[c]chromen-3-yl)ethyl)-1H-1,2,3-triazole (INT-21)

To a suspension of sodium hydride (60% dispersion in mineral oil, 27.2 mg, 1.13 mmol) in N,N-dimethylacetamide (10 mL) was added 1H-1,2,3-triazole (58.8 mg, 0.847 mmol) at 0° C., and the mixture was stirred for 15 min. A solution of 2-(1-(benzyloxy)-6,6,9-trimethyl-6H-benzo[c]-chromen-3-yl)ethyl 4-methylbenzenesulfonate (INT-20, 300 mg, 0.57 mmol) in N,N-dimethyl-acetamide (3 mL) was added to the suspension, and stirring was continued at room temperature for 16 h. After this time, ice-cold water (10 mL) was added slowly to quench excess sodium hydride and the mixture was extracted with ethyl acetate (2×15 mL). The combined organic extracts were washed with brine (5 mL), dried over sodium sulfate, filtered and concentrated under reduced pressure. The residue obtained was purified by chromatography (silica gel; hexanes to 50:50 hexanes/ethyl acetate) to afford 1-(2-(1-(benzyloxy)-6,6,9-trimethyl-6H-benzo[c]chromen-3-yl)ethyl)-1H-1,2,3-triazole (87, 180 mg, 74%) as an off-white solid. Product regiochemistry was confirmed by $^1$H NMR and 1D NOE analysis.

$^1$H NMR (400 MHz, DMSO-d6): δ 8.20 (s, 1H), 8.02 (s, 1H), 7.69 (s, 1H), 7.56 (d, J=7.6 Hz, 2H), 7.45 (t, J=7.6 Hz, 2H), 7.38 (t, J=7.2 Hz, 1H), 7.19 (d, J=7.6 Hz, 1H), 7.05 (d, J=7.6 Hz, 1H), 6.73 (s, 1H), 6.43 (s, 1H), 5.18 (s, 2H), 4.68 (t, J=7.6 Hz, 2H), 3.13 (t, J=7.2 Hz, 2H), 2.17 (s, 3H), 1.49 (s, 6H); MS (ESI) m/z 426 [M+H]+.

(h) 3-(2-(1H-1,2,3-triazol-1-yl)ethyl)-6,6,9-trimethyl-6H-benzo[c]chromen-1-ol (54):

To a stirred solution of 1-(2-(1-(benzyloxy)-6,6,9-trimethyl-6H-benzo[c]chromen-3-yl)ethyl)-1H-1,2,3-triazole (INT-21, 180 mg, 0.42 mmol) in ethanol (10 mL) was added 10% palladium on carbon (50% wet, 90 mg) under a nitrogen atmosphere. The reaction mixture was stirred under 1 atm of hydrogen for 16 h at room temperature. After this time, the reaction mixture was filtered through diatomaceous earth, and the filter cake was washed with ethyl acetate (2×30 mL). The filtrate was concentrated under reduced pressure. The residue obtained was purified by chromatography (silica gel; hexanes to 30:70 hexanes/ethyl acetate) to afford 3-(2-(1H-1,2,3-triazol-1-yl)ethyl)-6,6,9-trimethyl-6H-benzo[c]chromen-1-ol (54) (60 mg, 42%) as a light-pink solid.

$^1$H NMR (400 MHz, DMSO-d6): δ 9.98 (s, 1H), 8.26 (s, 1H), 8.01 (d, J=0.8 Hz, 1H), 7.67 (d, J=0.4 Hz, 1H), 7.18 (d, J=7.6 Hz, 1H), 7.05 (dd, J=7.8, 1.2 Hz, 1H), 6.36 (d, J=1.6 Hz, 1H), 6.26 (d, J=1.6 Hz, 1H), 4.60 (t, J=7.2 Hz, 2H), 3.02 (t, J=7.2 Hz, 2H), 2.30 (s, 3H), 1.48 (s, 6H); MS (ESI) m/z 336 [M+H]+; HPLC: Method 2, tR=3.53 min, 98.8% (AUC).

Example 5

Synthesis of 3-(2-(1H-1,2,4-triazol-1-yl)ethyl)-6,6,9-trimethyl-6H-benzo[c]chromen-1-ol (55)

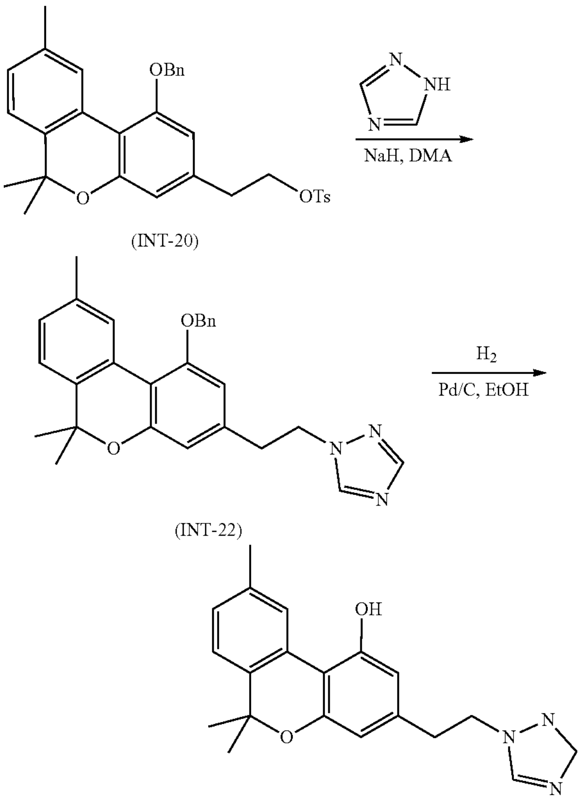

(INT-20)

(INT-22)

(55)

3-(2-(1H-1,2,4-triazol-1-yl)ethyl)-6,6,9-trimethyl-6H-benzo[c]chromen-1-oI (55) was synthesized according to Scheme 8, as follows:

(a) Synthesis of 1-(2-(1-(benzyloxy)-6,6,9-trimethyl-6H-benzo[c]chromen-3-yl)ethyl)-1H-1,2,4-triazole (INT-22):

To a suspension of sodium hydride (60% dispersion in mineral oil, 0.036 g, 1.5 mmol) in N,N-dimethylacetamide (10 mL) was added 1H-1,2,4-triazole (0.10 g, 1.5 mmol) at 0° C., and the mixture was stirred for 15 min. A solution of 2-(1-(benzyloxy)-6,6,9-trimethyl-6H-benzo[c]-chromen-3-yl)ethyl 4-methylbenzenesulfonate (INT-20, 0.80 g, 1.5 mmol) in N,N-dimethylacetamide (3 mL) was added. The mixture was allowed to warm to room temperature and stir for 16 h. After this time, ice-cold water (10 mL) was slowly added to quench excess sodium hydride and the mixture was extracted with ethyl acetate (2×15 mL). The combined organic extracts were washed with brine (5 mL), dried over sodium sulfate, filtered and concentrated under reduced pressure. The residue obtained was purified by chromatography (silica gel; hexanes to 50:50 hexanes/ethyl acetate) to afford 1-(2-(1-(benzyloxy)-6,6,9-trimethyl-6H-benzo[c]chromen-3-yl)ethyl)-1H-1,2,4-triazole (INT-22, 160 mg, 25%). Product regiochemistry was confirmed by $^1$H NMR and 1D NOE analysis.

$^1$H NMR (400 MHz, DMSO-d6): δ 8.34 (s, 1H), 8.20 (s, 1H), 7.99 (s, 1H), 7.56 (t, J=6.8 Hz, 2H), 7.47-7.44 (m, 2H), 7.40-7.37 (m, 1H), 7.19 (d, J=8.0 Hz, 1H), 7.05 (dd, J=7.8, 1.2 Hz, 1H), 6.67 (d, J=1.2 Hz, 1H), 6.39 (d, J=1.6 Hz, 1H), 5.17 (s, 2H), 4.47 (t, J=6.8 Hz, 2H), 3.07 (t, J=7.2 Hz, 2H), 2.16 (s, 3H), 1.48 (s, 6H); MS (ESI) m/z 426 [M+H]+.

(b) Synthesis of 3-(2-(1H-1,2,4-triazol-1-yl)ethyl)-6,6,9-trimethyl-6H-benzo[c]chromen-1-ol (55):

To a stirred solution of 1-(2-(1-(benzyloxy)-6,6,9-trimethyl-6H-benzo[c]chromen-3-yl)ethyl)-1H-1,2,4-triazole (INT-22, 155 mg, 0.364 mmol) in ethanol (10 mL) was added 10% palladium on carbon (50% wet, 50.0 mg) under a nitrogen atmosphere. The resulting reaction mixture was stirred under 1 atm of hydrogen for 16 h at room temperature. After this time, the reaction mixture was filtered through diatomaceous earth, and the filter cake washed with ethyl acetate (2×30 mL). The filtrate was concentrated under reduced pressure. The residue obtained was purified by chromatography (silica gel; hexanes to 30:70 hexanes/ethyl acetate) to afford 3-(2-(1H-1,2,4-triazol-1-yl)ethyl)-6,6,9-trimethyl-6H-benzo[c]chromen-1-ol (Nalu-0021, 50 mg, 39%) as an off-white solid.

$^1$H NMR (400 MHz, DMSO-d6): δ 9.96 (s, 1H), 8.33 (s, 1H), 8.26 (s, 1H), 7.96 (s, 1H), 7.18 (d, J=7.6 Hz, 1H), 7.05 (dd, J=7.8, 0.8 Hz, 1H), 6.32 (d, J=1.6 Hz, 1H), 6.21 (d, J=1.6 Hz, 1H), 4.39 (t, J=7.2 Hz, 2H), 2.96 (t, J=6.8 Hz, 2H), 2.30 (s, 3H), 1.48 (s, 6H); MS (ESI) m/z 336 [M+H]+; HPLC: tR=3.08 min, 98.3% (AUC).

Example 6

Synthesis of 3-(2-(4H-1,2,3-triazol-4-yl)ethyl)-6,6,9-trimethyl-6H-benzo[c]chromen-1-ol (56)

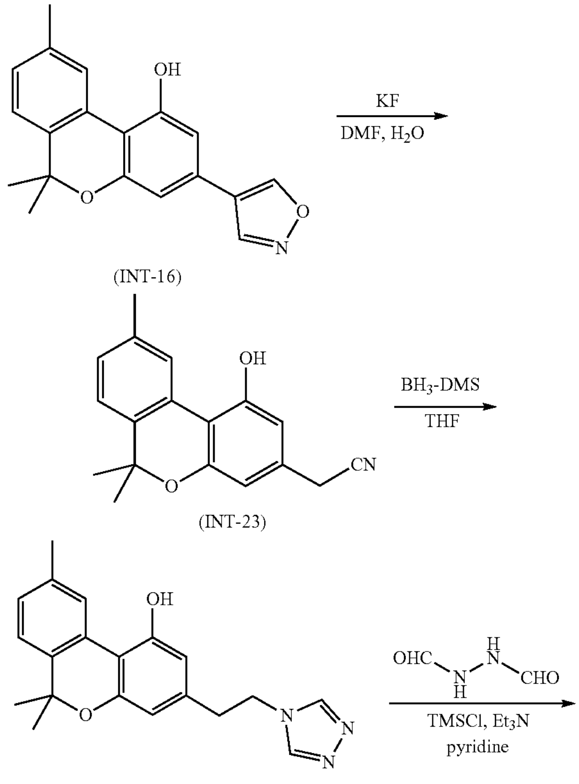

(INT-16)

(INT-23)

(INT-24)

-continued

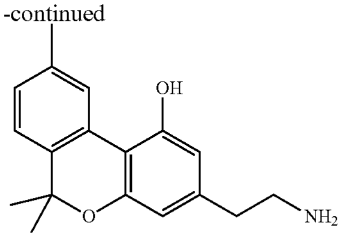

(56)

3-(2-(4H-1,2,4-triazol-4-yl)ethyl)-6,6,9-trimethyl-6H-benzo[c]chromen-1-ol (56) was synthesized according to Scheme 9, as follows:

Synthesis of 2-(1-hydroxy-6,6,9-trimethyl-6H-benzo[c]chromen-3-yl)acetonitrile (INT-23):

To a stirred solution of 3-(isoxazol-4-yl)-6,6,9-trimethyl-6H-benzo[c]chromen-1-ol (INT-16, 2.5 g, 8.1 mmol) in N,N-dimethylformamide (25 mL) and water (25 mL) was added potassium fluoride (1.41 g, 24.4 mmol) at room temperature. The resultant mixture was stirred at 100° C. for 16 h. After this time, the mixture was cooled, combined with water (50 mL), and extracted with ethyl acetate (2×100 mL). The organic extracts were collected, dried over sodium sulfate, filtered and concentrated under reduced pressure. The residue obtained was purified by chromatography (silica gel; hexanes to 80:20 hexanes/ethyl acetate) to afford 2-(1-hydroxy-6,6,9-trimethyl-6H-benzo[c]chromen-3-yl)acetonitrile (INT-23, 660 mg, 29%) as a light-yellow solid.

$^1$H NMR (400 MHz, DMSO-d6): δ 10.28 (s, 1H), 8.29 (s, 1H), 7.20 (dd, J=7.2, 4.4 Hz, 1H), 7.08 (s, 1H), 6.57 (d, J=3.2 Hz, 1H), 6.37 (d, J=2.8 Hz, 1H), 3.93 (s, 2H), 2.32 (s, 3H), 1.51 (s, 6H); MS (ESI) m/z 280 [M+H]+.

Synthesis of 3-(2-aminoethyl)-6,6,9-trimethyl-6H-benzo[c]chromen-1-ol (INT-24)

To a stirred solution of 2-(1-hydroxy-6,6,9-trimethyl-6H-benzo[c]chromen-3-yl)acetonitrile (INT-23, 470 mg, 1.7 mmol) in tetrahydrofuran (10 mL) was added borane dimethyl sulfide complex (0.79 mL, 8.4 mmol) at 0° C. The resultant mixture was heated at 70° C. for 16 h. After this time, methanol (20 mL) was added, and the mixture was heated at reflux for 1 h. The mixture was cooled, diluted with water (50 mL) and extracted with ethyl acetate (2×70 mL). The organic extracts were collected, dried over sodium sulfate, filtered and concentrated under reduced pressure to afford 3-(2-aminoethyl)-6,6,9-trimethyl-6H-benzo[c]chromen-1-ol (INT-24, 500 mg) as a brown gum that was used in the next step without purification. MS (ESI) m/z 284 [M+H]+.

Synthesis of 3-(2-(4H-1,2,4-triazol-4-yl)ethyl)-6,6,9-trimethyl-6H-benzo[c]chromen-1-ol (56):

To a stirred solution of 3-(2-aminoethyl)-6,6,9-trimethyl-6H-benzo[c]chromen-1-ol (INT-24, 500 mg, 1.8 mmol), triethylamine (1.72 mL, 12.4 mmol) and chlorotrimethylsilane (3.38 mL, 26.5 mmol) in pyridine (20 mL) was added N'-formylformohydrazide (466 mg, 5.29 mmol) at 0° C. The resultant mixture was heated at 100° C. for 16 h. After this time, water (10 mL) was added, and the mixture was extracted with ethyl acetate (2×20 mL). The organic extracts were combined, washed with brine (10 mL), dried over sodium sulfate, filtered and concentrated under reduced pressure. The residue obtained was purified by mass-triggered preparative HPLC to afford 3-(2-(4H-1,2,4-triazol-4-yl)ethyl)-6,6,9-trimethyl-6H-benzo[c]chromen-1-ol (56), 100 mg, 17%) as an off-white solid. 1H NMR (400 MHz, DMSO-d6) δ 10.01 (s, 1H), 8.42 (s, 2H), 8.26 (d, J=0.8 Hz, 1H), 7.18 (d, J=8.0 Hz, 1H), 7.06 (dd, J=7.8, 1.2 Hz, 1H), 6.33 (d, J=1.6 Hz, 1H), 6.27 (d, J=1.6 Hz, 1H), 4.26 (t, J=7.2 Hz, 2H), 2.91 (t, J=7.2 Hz, 2H), 2.30 (s, 3H), 1.49 (s, 6H); MS (ESI) m/z 336 [M+H]+; HPLC: Method 2, tR=2.99 min, >99% (AUC).

Example 7

Radioligand Binding Assay and Data

Compound plates were prepared by diluting a 5 mM DMSO stock solution of the reference compound (CP55940, CAS Number 83003-12-7, 5-(1,1-dimethylheptyl)-2-[(1R, 2R, 5R)-5-hydroxy-2-(3-hydroxypropyl)cyclohexyl]phenol) in a series of five-fold dilutions to generate eight distinct concentrations of each CBN analog undergoing evaluation, i.e., compounds (1), (2), and (3). Stock solutions of the test compounds were also prepared in DMSO. A volume of 750 nL from each reference and test compound was transferred to a 96-well plate, followed by the addition of 150 μL of assay buffer to achieve a 5× working concentration. The plates were then centrifuged at 1,000 rpm for 30 seconds and mixed at 600 rpm for 5 minutes at room temperature.

Separately, each well of UniFilter-96 GF/C plates was treated with 50 μL of 0.5% (v/v) polyethyleneimine (PEI), sealed, and incubated at 4° C. for 3 hours. The plates underwent two washes with ice-cold buffer before use. Cell membranes were suspended in assay buffer and dispensed into 96-round deep-well plates at a final concentration of 10 μg per well (330 μL per well). Next, 110 μL of each test compound concentration and 110 μL of each reference compound concentration were transferred from the compound plate to the deep-well plates. Radiolabeled ligands were prepared in assay buffer, and 110 μL of this solution was added to each well to obtain a 5× working concentration. The final concentrations of $[^3H]$—CP55940 were 2 nM for CB1 and 1.25 nM for CB2.

Following compound and radioligand addition, the plates were centrifuged at 1,000 rpm for 30 seconds and shaken at 600 rpm for 5 minutes at room temperature. They were then sealed and incubated at 30° C. for 90 minutes. Incubation was terminated by vacuum filtration through GF/C plates, followed by four washes with ice-cold buffer. The plates were dried at 37° C. for 45 minutes, after which 40 μL of scintillation cocktail was added to each well. Radioactivity levels were measured using a MicroBeta2 microplate counter (PerkinElmer, Waltham, MA, USA).

IC50 values of CBN analogs in radioligand binding assay are indicated in Table 2:

TABLE 2

| Compound | CB1 | CB2 |
|---|---|---|
| (1) | 219 nM | 273 nM |
| (2) | 619 nM | 262 nM |
| (3) | 4608 nM | 3899 nM |

Example 8

Evaluation of CBN Analogs in Treating Pain and Inflammation in Vivo

Experimental Procedure:

Male CD-1 mice (n=85, 18-20 g; Envigo) were housed under standard conditions with ad libitum access to food and water. After a 3-day acclimation period, mice were weight-matched into eight groups (n=10/group). Inflammation was induced via subcutaneous injection of 1.2% carrageenan (20 μL) into the left hind paw. The selected CBN analog, (1), (2), or (3), and vehicle (7.8% Tween 80 in saline) were administered intraperitoneally 0.5 h prior to carrageenan. Carprofen (30 mg/kg) and morphine (5 mg/kg) were administered subcutaneously.

Assessments:

Ankle Diameter: Measured using a digital micrometer at baseline and 2, 4, 6, and 8 h post-carrageenan. Percent change from baseline and left-right differences were calculated.

Thermal Hyperalgesia (Hargreaves Test): Baseline latency was established on Day 3. Post-treatment response times were recorded using a heated apparatus (30° C.; 20 s cutoff) at 1 and 3 h post carrageenan.

Data are expressed as mean±SEM. Ordinary one-way ANOVA with Dunnett's post hoc test compared treatment groups to vehicle controls. Significance was set at $p<0.05$ (GraphPad Prism 10.3.1). All procedures adhered to institutional guidelines, and euthanasia was performed under isoflurane anesthesia.

The results are illustrated in the graphs of FIGS. 1 through 6. As illustrated therein, compounds (1), (2), and (3) exhibit potent efficacy in treating pain and inflammation compared to NSAIDs and morphine.

Example 9

In Vivo Pharmacokinetic Evaluation

Animals and Study Design:

Male CD-1 mice (6-8 weeks old, 20.5-25.1 g) were administered with the CBN analogs (1), (2), and (3) via intraperitoneal (IP) injection at three dose levels: 3, 30, and 100 mg/kg (n=3 per group). Dosing formulations were prepared as suspensions in 7.8% Tween 80 (polysorbate 80) and saline, with concentrations of 0.6, 6, and 20 mg/mL, respectively. Animals were fasted prior to dosing, and blood samples (~0.03 mL) were collected from the dorsal metatarsal vein at 0.25, 0.5, 1, 2, 4, 6, 8, and 24 hours post-dose. Plasma was separated via centrifugation (4000×g, 5 min, 4C) and stored at −75±15° C. until analysis.

Plasma concentrations of the CBN analogs were quantified using a validated LC-MS/MS method. Samples were protein-precipitated with acetonitrile containing dexamethasone as the internal standard. Chromatographic separation was achieved on a Phenomenex® Kinetex C18 column (2.6 μm, 30×2.1 mm) with a gradient mobile phase (5-95% acetonitrile in 0.1% formic acid). Quantification employed a Shimadzu LC-40D system coupled to an AB Sciex API 6500 mass spectrometer, operating in MRM mode (Q1/Q3: 416.17/176.20 Da). Calibration curves (0.5-1000 ng/mL) and quality controls demonstrated accuracy within 88.5-110%. Non-compartmental analysis (WinNonlin 8.3) was used to estimate parameters, including half-life (T1/2) maximum concentration (Cmax), area under the curve (AUClast, AUCinf), and mean residence time (MRT).

The pharmacokinetic data obtained is shown in Table 3:

TABLE 3

| Summary of PK data at 30 mg/kg dose | | | | |
|---|---|---|---|---|
| PK parameters | Unit | Cpd. (1) (30 mg/kg, i.p.) | Cpd. (2) (30 mg/kg, i.p.) | Cpd. (3) (30 mg/kg, i.p.) |
| $T_{1/2}$ | h | 7.77 | 4.97 | 1.55 |
| $T_{max}$ | h | 0.500 | 0.500 | 0.250 |
| $C_{max}$ | nM | 1235 | 5296 | 4640 |

TABLE 3-continued

| Summary of PK data at 30 mg/kg dose | | | | |
| --- | --- | --- | --- | --- |
| PK parameters | Unit | Cpd. (1) (30 mg/kg, i.p.) | Cpd. (2) (30 mg/kg, i.p.) | Cpd. (3) (30 mg/kg, i.p.) |
| $AUC_{last}$ | h * nM | 2399 | 10825 | 2899 |
| $AUC_{Inf}$ | h * nM | 2440 | 10968 | 2915 |
| $AUC_{\%Extrap}_obs$ | % | 1.69 | 1.31 | 0.570 |
| $MRT_{Inf}$_obs | h | 2.47 | 3.06 | 0.860 |
| $AUC_{last}$/D | h * nM/(mg/kg) | 80.0 | 361 | 96.6 |

Figure 7:
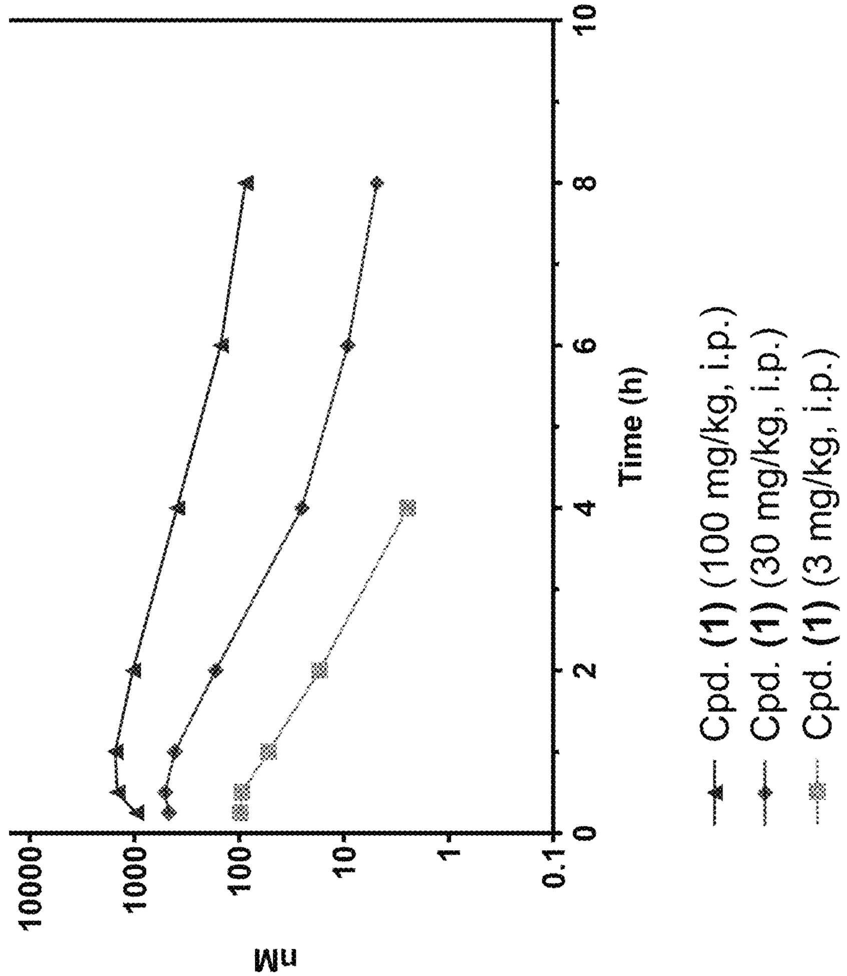
FIG. 7 is a graph showing the pharmacokinetic profile obtained after administration of the CBN analog (1) to mice at different doses, determined as described in Example 9.
Figure 8:
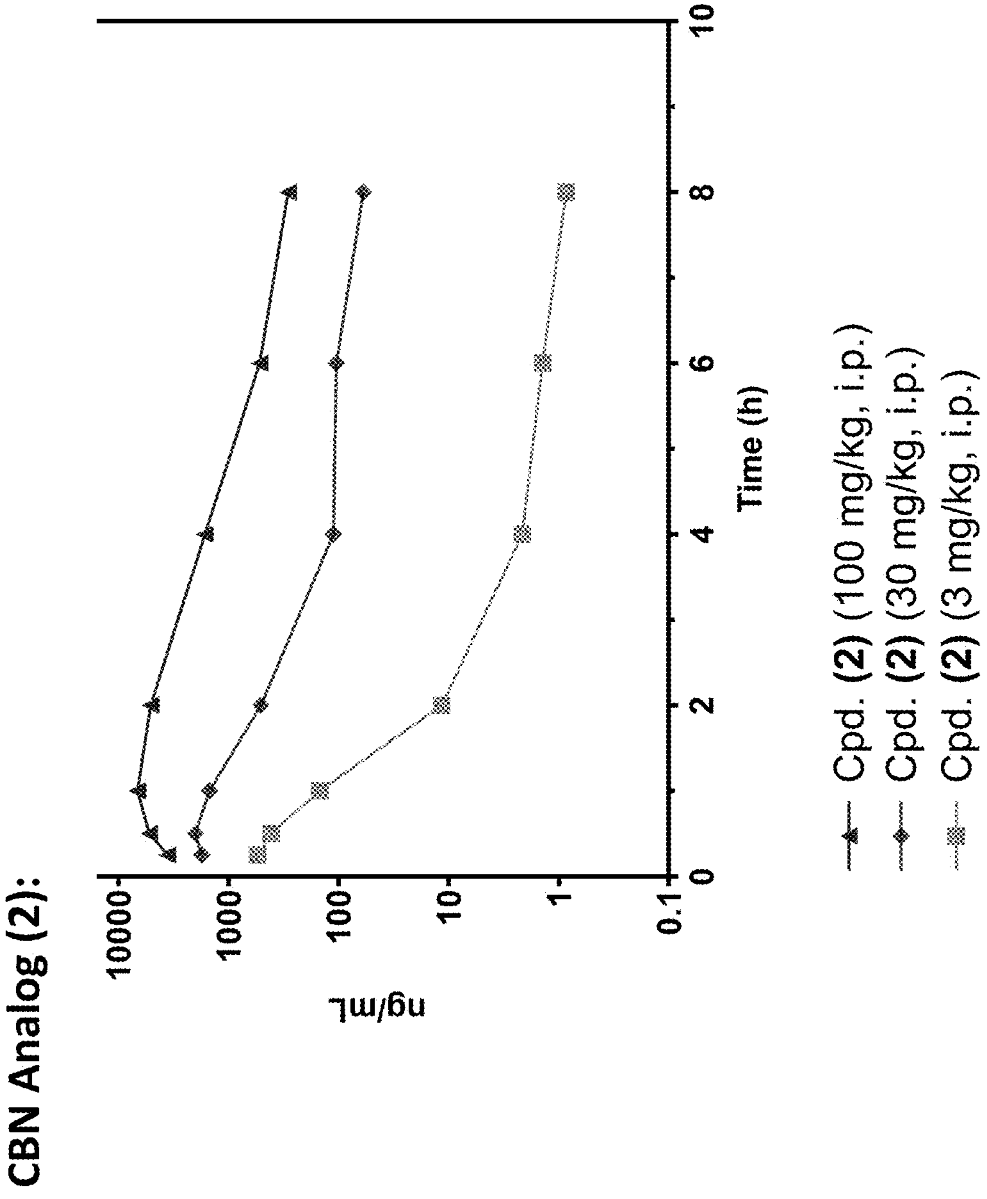
FIG. 8 is a graph showing the pharmacokinetic profile obtained after administration of the CBN analog (2) to mice at different doses, determined as described in Example 9.
Figure 9:
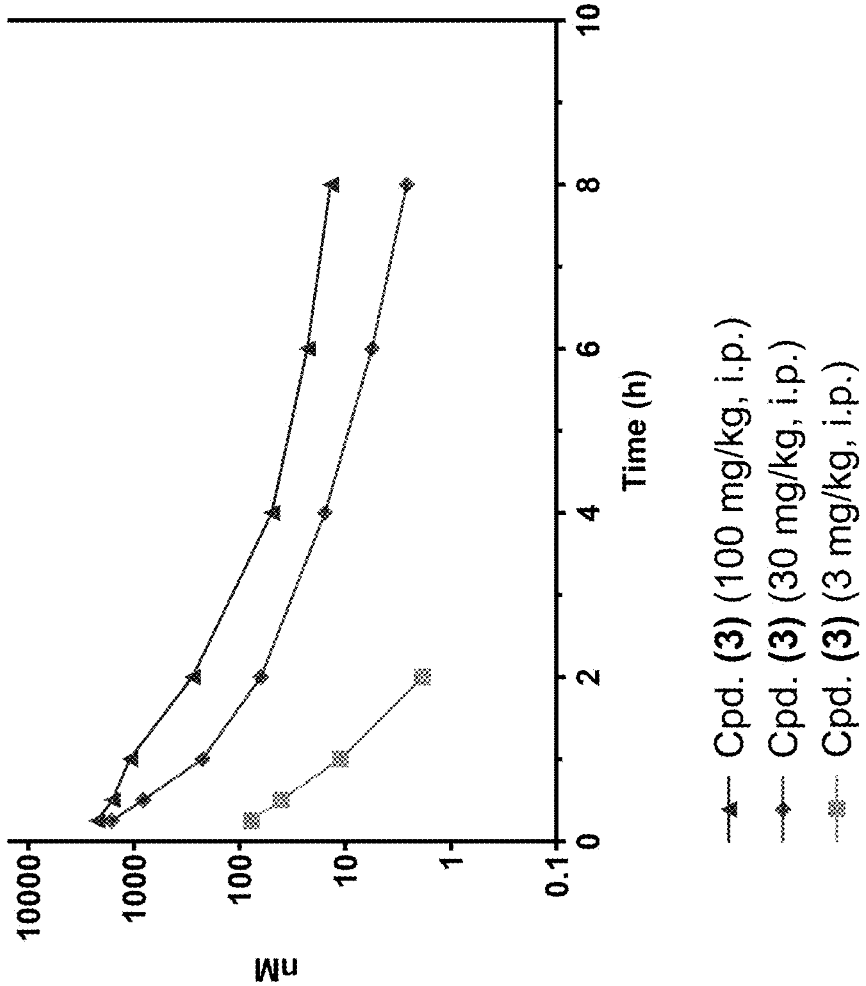
FIG. 9 is a graph showing the pharmacokinetic profile obtained after administration of the CBN analog (3) to mice at different doses, determined as described in Example 9.

The pharmacokinetic data obtained was plotted and is shown in FIG. 7 (for compound (1)), FIG. 8 (for compound (2)), and FIG. 9 (for compound (3)). As may be seen, the two CBN analogs follow approximately linear pharmacokinetics in the 3-100 mg/kg dose range. This is advantageous because it simplifies dose optimization and provides predictable drug behavior across different doses. Linear pharmacokinetics also helps with human dose prediction necessary to choose the starting dose in the clinic.

Example 10

CB1 and CB2 Agonist Assays

Arrestin assay: For arrestin CB1 and CB2 agonist assays, the PathHunter®-Arrestin CHO-K1 cells, which overexpress the CB1 or CB2 receptors, were cultivated from frozen stocks using the standard protocols supplied by Eurofins, adhering to the guidelines in the cell line manual for cell cultivation (covering aspects such as culture media, supplements, and cell handling) as well as for conducting the assay and detecting signals. Cells were dispensed at a density of 5000 cells per 20 μL into white-walled, 384-well plates and then incubated at 37° C. overnight in cell plating reagent. Subsequently, a stock solution of the ligand in DMSO at 1 mg/mL was prepared, from which intermediate concentrations of the compound were derived through a series of ten 3-fold serial dilutions using dilution buffer in a separate dilution plate. Each dilution was prepared at a 5× concentration relative to the intended final concentrations for screening. Next, 5 μL of these samples was introduced into the cells, achieving a maximum final concentration of 10 μM for the test compound. Cells were incubated at 37° C. for 90 min in an atmosphere containing 5% CO2. To generate the assay signal, 12.5 μL of working detection solution was added to the cells, which were then left to incubate for an hour at room temperature in the dark. The signal detection was carried out using a PerkinElmer Envision instrument to measure chemiluminescence.

cAMP assay: For the cAMP CB1 and CB2 agonist assays, the cAMP Hunter™ CHO-K1 cells, which overexpress CB1 and CB2 receptors, were cultivated from frozen stocks using the standard protocols supplied by Eurofins, adhering to the guidelines in the cell line manual for cell cultivation (covering aspects such as culture media, supplements, and cell handling) as well as for conducting the assay and detecting signals. Cells were seeded in a total volume of 20 μL (10,000 cells) into white-walled, 384-well microplates and incubated at 37° C. in cell plating reagent overnight. Before adding ligands, media were aspirated from cells and replaced with 10 μL cAMP assay buffer. Stock DMSO solution at 1 mg/mL concentration of test compounds was diluted in cAMP assay buffer to generate a 3× sample containing 3× EC80 forskolin. Five μL of sample solution was added to cells (highest final concentration=3 μM) and incubated at 37° C. for 30 min. The assay signal was generated through incubation with 5 μL antibody solution and 20 μL working cAMP detection solution for one hour (room temperature, dark), followed by incubation with 20 μL cAMP solution A for three hours at room temperature in the dark. Microplates were read following signal generation with a PerkinElmer Envision instrument for chemiluminescent signal detection.

EC50 values of compounds in the CB1 and CB2 agonist assays:

| | CB1 | | | CB2 | | |
| --- | --- | --- | --- | --- | --- | --- |
| Compound | cAMP | B-arrestin | Functional activity | cAMP | B-arrestin | Functional activity |
| (1) | 917 nM | >3000 nM | Partial agonist | 540 nM | >3000 nM | Partial agonist |
| (2) | 2035 nM | 976 nM | Partial agonist | 670 nM | 22 nM | Inverse agonist |
| (3) | >3000 nM | >3000 nM | No agonist activity | 284 nM | 236 nM | Inverse agonist |

Compounds (1), (2), and (3) demonstrate distinct receptor subtype selectivity and functional activity at the CB1 and CB2 receptors. Compound (1) acts as a G-protein-biased partial agonist at both CB1 and CB2, while compound (3) exhibits inverse agonism at CB2 with no apparent CB1 activity, indicating subtype selectivity. Compound (2) shows inverse agonism at CB2 and partial agonism at CB1, with significantly greater potency in 0-arrestin recruitment at CB2.

Example 11

Endometriosis Study

Female C57BL/6J mice (7-8 weeks old) housed under controlled conditions (20-25° C., 40-70% humidity, 12-h light/dark cycle) with ad libitum access to food and water. Animals were acclimated for 7 days prior to the study. To induce endometriosis, estrous cycle stages were identified in donor animals via daily vaginal smears, and proestrus/estrus-phase animals were selected. Donor mice were euthanized and their uterine horns harvested. Uterine tissue was trimmed and cut into 2×2 mm fragments, which were then sutured onto the abdominal wall of recipient mice under anesthesia via midline laparotomy (four fragments per mouse). Sham-operated animals received adipose tissue grafts instead of endometrial tissue, and healthy controls underwent laparotomy without any tissue transplantation. Post-operative care included administration of analgesics (meloxicam and butorphanol) and antibiotics (ampicillin) for 2 days. Estradiol (17β-estradiol, 25 μg/kg) was administered subcutaneously every 3 days for a total of nine doses to support endometrial graft survival.

Four weeks post-transplantation, endometriotic lesions were assessed via caliper measurement. Mice with established lesions were randomized into 13 groups (n=6-11/group) with equivalent lesion volumes. Treatment with CBN analogs (1), (2), and (3) was carried out at the doses indicated in FIG. 10 (in FIG. 10, "EM" represents endometriosis), with carprofen treatment and no treatment (administration of formulation free of active agent) carried out for purposes of comparison. The formulations were administered daily, intraperitoneally (i.p.) or subcutaneously (s.c.), for four weeks. All formulations used 7.8% Tween 80 in saline for test articles and saline alone for reference and vehicle controls.

Figure 10:
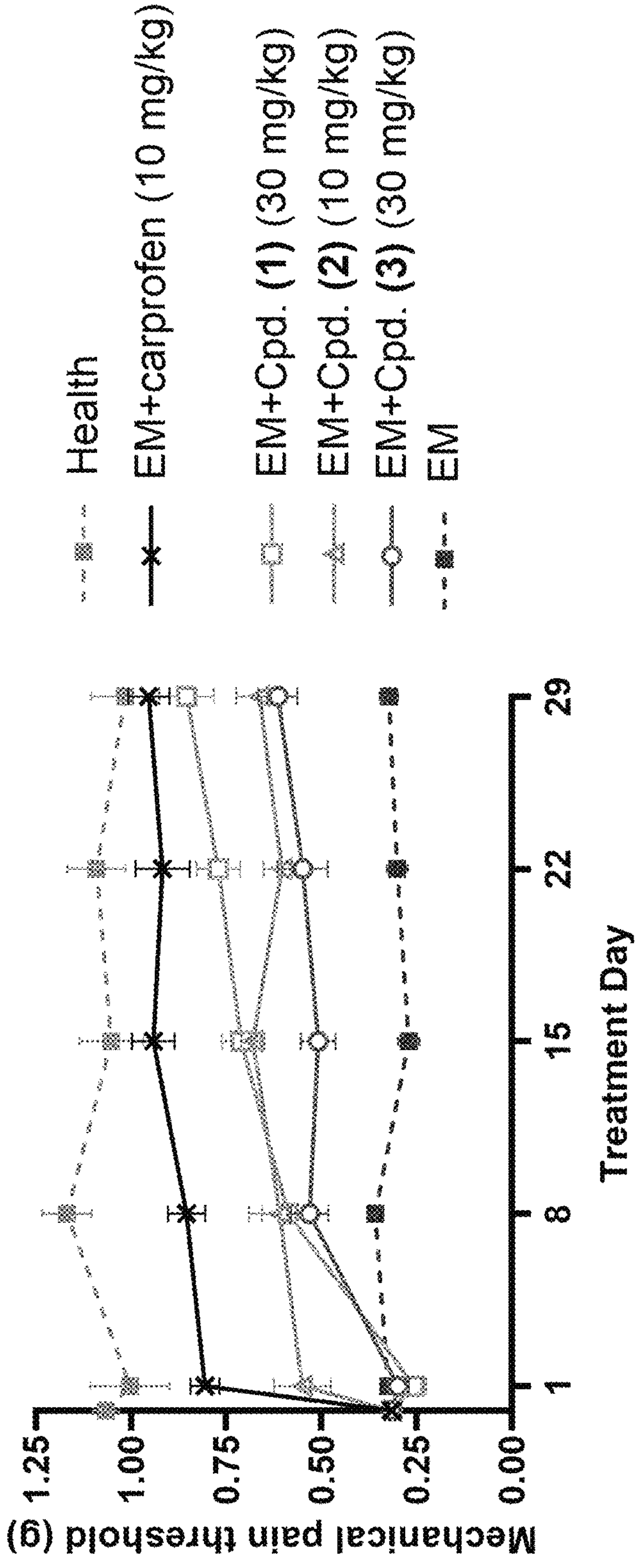
FIG. 10 provides, in graph form, the results of the experiment of Example 11 conducted to evaluate the effect of CBN analogs (1), (2), and (3) on endometrial pain in mice.
Figure 11:
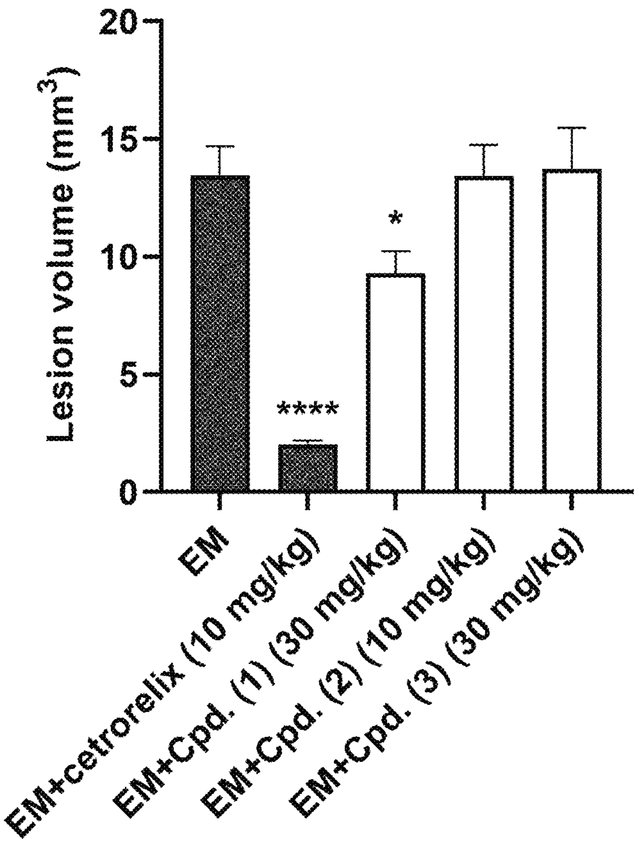
FIG. 11 provides a bar graph illustrating the effect of CBN analogs (1), (2), and (3) on endometrial tissue size, as described in Example 11.

As indicated in the results illustrated in the graphs of FIGS. 10 and 11, CBN analogs (1), (2), and (3) displayed pain mitigation, with compound (1) demonstrating a significant reduction in endometrial lesion volume compared to the disease model (EM) control, indicating a disease-modifying effect. This finding suggests that compound (1) effectively prevents lesion progression and supports its potential as a therapeutic candidate for the treatment of endometriosis. FIG. 11 illustrates the effect of CBN analogs (1), (2), and (3) on endometrial tissue size, with cetrorelix used as a control.

von Frey mechanical allodynia was assessed on days 36, 43, 50, 57, and 62 using calibrated filaments applied to the left hind paw and abdomen. Thresholds were calculated using the Dixon up-down method. Following the final treatment, mice in estrus phase (except cetrorelix group) were selected for terminal procedures within 2-4 hours after dosing. Animals were euthanized via $CO_2$ inhalation followed by cervical dislocation. Peritoneal lavage fluid, blood, and uterine grafts were collected. Grafts were measured, weighed, photographed, and preserved in 10% formalin for future analysis. The results obtained indicated that CBN analog (1) significantly reduced endometrial lesion volume.

Example 12

Further Evaluation of CBN Analogs as Drug Candidates

Receptor affinities, log P, topological polar surface area (TPSA), hydrogen bond donors (HBD), and molecular weight of CBN analogs having the structure of formula (I) (and defined in Table 1 and elsewhere herein) were calculated and are set forth in Table 4. Receptor affinities were calculated using Boltz-2, an open source structural biology foundation model described, inter alia, by Passaro et al., "Boltz-2: Towards Accurate and Efficient Binding Affinity Prediction," posted Jun. 18, 2025 as a bioRxiv preprint doi: https:H/doi.org/10.1101/2025.06.14.659707. Log P, TPSA, and HBD were calculated using ADMET-AI; see Swanson et al., "ADMET-AI: A Machine Learning ADMET Platform for Evaluation of Large Scale Chemical Libraries," posted Dec. 28, 2023 as a bioRxiv preprint doi: https:H/doi.org/10.1101/2023.12.28.573531.

TABLE 4

| Cpd. No. | CB1 affinity (calc) | CB2 affinity (calc) | log P | TPSA ($Å^2$) | HBD | MW |
|---|---|---|---|---|---|---|
| (1) | 109.4 | 11.1 | 5.041 | 49.77 | 1 | 415.4 |
| (2) | 221.3 | 34.6 | 4.796 | 49.77 | 1 | 379.5 |
| (3) | 256.4 | 245.4 | 3.354 | 59.00 | 2 | 353.4 |
| (4) | 594 | 59.4 | 2.45 | 70.08 | 1 | 430.4 |
| (5) | 417 | 39.9 | 3.357 | 53.01 | 1 | 416.5 |
| (6) | 338.1 | 23.9 | 3.635 | 61.8 | 2 | 416.5 |
| (7) | 83.2 | 13.5 | 4.993 | 61.8 | 2 | 444.5 |
| (8) | 1390 | 39.1 | 3.959 | 73.83 | 3 | 445.5 |
| (9) | 363 | 51.5 | 3.184 | 78.87 | 2 | 445.5 |
| (10) | 363 | 33.7 | 3.912 | 49.77 | 1 | 387.4 |
| (11) | 177 | 39 | 4.314 | 61.8 | 2 | 416.5 |
| (12) | 4270 | 1770 | 3.709 | 87.07 | 2 | 445.5 |
| (13) | 239 | 16.2 | 5.433 | 49.77 | 1 | 441.5 |
| (14) | 100 | 17.9 | 4.085 | 66.84 | 1 | 451.5 |
| (15) | 83 | 7.1 | 4.287 | 66.84 | 1 | 465.6 |
| (16) | 258 | 6.46 | 2.66 | 87.15 | 1 | 466.6 |
| (17) | 123 | 20.1 | 3.934 | 59 | 1 | 417.4 |
| (18) | 200 | 14.6 | 4.231 | 49.77 | 1 | 401.4 |
| (19) | 200 | 4.51 | 4.569 | 49.77 | 1 | 391.5 |
| (20) | 19 | 7.94 | 3.778 | 76.07 | 1 | 467.5 |
| (21) | 43.3 | 42.9 | 3.363 | 95.94 | 2 | 494.6 |
| (22) | 208.4 | 245.5 | 3.335 | 108 | 3 | 509.6 |
| (23) | 242.1 | 125 | 5.107 | 51.46 | 1 | 397.4 |
| (25) | 94.4 | 3.45 | 3.564 | 70 | 2 | 431.5 |

TABLE 4-continued

| Cpd. No. | CB1 affinity (calc) | CB2 affinity (calc) | log P | TPSA ($Å^2$) | HBD | MW |
|---|---|---|---|---|---|---|
| (26) | 175 | 130 | 3.143 | 108 | 3 | 495.5 |
| (28) | 203.7 | 252.3 | 2.909 | 108 | 3 | 477.5 |
| (30) | 202.3 | 776.2 | 3.203 | 108 | 3 | 473.6 |
| (32) | 106.9 | 54.6 | 2.736 | 131.8 | 3 | 484.6 |
| (34) | 147.2 | 15.4 | 2.755 | 110.9 | 2 | 456.6 |
| (35) | 79.8 | 17.1 | 3.143 | 85.59 | 2 | 419.5 |
| (36) | 289.7 | 38.1 | 2.909 | 105.8 | 3 | 435.5 |
| (37) | 55.5 | 17.1 | 3.203 | 94.82 | 2 | 421.5 |
| (38) | 109.6 | 161.4 | 2.79 | 131.8 | 3 | 448.5 |
| (39) | 35.5 | 44.8 | 3.981 | 78.8 | 2 | 444.478 |
| (40) | 66.8 | 61.8 | 3.784 | 95.94 | 2 | 494.560 |
| (41) | 89.9 | 274.2 | 3.423 | 114.690 | 3 | 448.523 |
| (42) | 166.3 | 77.4 | 4.688 | 64.350 | 1 | 398.409 |
| (43) | 63.8 | 36.5 | 3.697 | 99.18 | 2 | 481.52 |
| (44) | 111.7 | 40.7 | 2.998 | 122.97 | 2 | 470.551 |
| (45) | 66.8 | 14.5 | 5.522 | 61.8 | 2 | 462.5 |
| (46) | 95.7 | 8.26 | 5.142 | 66.84 | 1 | 483.552 |
| (47) | 52 | 10.7 | 4.730 | 76.07 | 1 | 485.524 |
| (48) | 84.9 | 3.56 | 4.829 | 70 | 2 | 449.469 |

The following Examples 13-51 describe preparation of pharmaceutical dosage forms for oral administration of a CBN analog of the invention.

Example 13

Gummy Formulation

A gummy formulation of the invention is prepared by combining CBN analog (1) with sugar, tapioca syrup, water, pectin, flavoring agent, citric acid, fruit and vegetable juice colorant, coconut oil, and carnauba wax. The mixture is heated until it becomes flowable, and is then poured into individual gummy molds with each mold sized to provide a 4 g gummy. After molding, the gummies are cooled and dried, e.g., by air convection in convection chambers, to achieve a texture that is somewhat dry and sticky. The amount of CBN analog (1) in each 4 g gummy is 10 mg to 200 mg (0.25 wt. % to 5.0 wt. %), and the amount of sugar in each gummy is 1.58 g (39.5 wt. %). Pectin, the gelling agent, represents 5.0 wt. % of the gummy.

Example 14

Gummy Formulation

The method of Example 13 is repeated, with the non-sugar sweetener erythritol substituted for sugar. The amount of CBN analog (1) in each 4 g gummy is 10 mg to 200 mg (0.25 wt. % to 5.0 wt. %), and the amount of erythritol in each 4 g gummy is 1.58 g (39.5 wt. %). Pectin, the gelling agent, represents 5.0 wt. % of the gummy.

Example 15

Gummy Formulation

The method of Example 13 is repeated, with the non-sugar sweetener *stevia* substituted for sugar. The amount of CBN analog (1) in each 4 g gummy is 10 mg to 200 mg (0.25 wt. % to 5.0 wt. %), and the amount of *stevia* in each 4 g gummy is 1.58 g (39.5 wt. %). Pectin, the gelling agent, represents 5.0 wt. % of the gummy.

Example.16

Gummy Formulation

The method of Example 13 is repeated, with the non-sugar sweeteners *stevia* and erythritol substituted for sugar.

The amount of CBN analog (1) in each 4 g gummy is 10 mg to 200 mg (0.25 wt. % to 5.0 wt. %), and the combined amounts of erythritol and *stevia* in each 4 g gummy is 1.58 g (39.5 wt. %). Pectin, the gelling agent, represents 5.0 wt. % of the gummy.

Example 17

Gummy Formulation

The method of Example 13 is repeated, with agar gum substituted for pectin as the gelling agent. The amount of CBN analog (1) in each 4 g gummy is 10 mg to 200 mg (0.25 wt. % to 5.0 wt. %), and the amount of sugar in each 4 g gummy is 1.58 g (39.5 wt. %). Agar gum, the gelling agent, represents 5.0 wt. % of the gummy.

Example 18

Gummy Formulation

The method of Example 14 is repeated, with agar gum substituted for pectin as the gelling agent. The amount of CBN analog (1) in each 4 g gummy is 10 mg to 200 mg (0.25 wt. % to 5.0 wt. %), and the amount of erythritol in each 4 g gummy is 1.58 g (39.5 wt. %). Agar gum, the gelling agent, represents 5.0 wt. % of the gummy.

Example 19

Gummy Formulation

The method of Example 15 is repeated, with agar gum substituted for pectin as the gelling agent. The amount of CBN analog (1) in each 4 g gummy is 10 mg to 200 mg (0.25 wt. % to 5.0 wt. %), and the amount of *stevia* in each 4 g gummy is 1.58 g (39.5 wt. %). Agar gum, the gelling agent, represents 5.0 wt. % of the gummy.

Example 20

Gummy Formulation

The method of Example 16 is repeated, with agar gum substituted for pectin as the gelling agent. The amount of CBN analog (1) in each 4 g gummy is 10 mg to 200 mg (0.25 wt. % to 5.0 wt. %), and the combined amount of erythritol and *stevia* in each 4 g gummy is 1.58 g (39.5 wt. %). Agar gum, the gelling agent, represents 5.0 wt. % of the gummy.

Example 21

Gummy Formulation

The method of Example 13 is repeated, with carageenan substituted for pectin as the gelling agent. The amount of CBN analog (1) in each 4 g gummy is 10 mg to 200 mg (0.25 wt. % to 5.0 wt. %), and the amount of sugar in each 4 g gummy is 1.58 g (39.5 wt. %). Carageenan, the gelling agent, represents 5.0 wt. % of the gummy.

Example 22

Gummy Formulation

The method of Example 14 is repeated, with carageenan substituted for pectin as the gelling agent. The amount of CBN analog (1) in each 4 g gummy is 10 mg to 200 mg (0.25 wt. % to 5.0 wt. %), and the amount of erythritol in each 4 g gummy is 1.58 g (39.5 wt. %). Carageenan, the gelling agent, represents 5.0 wt. % of the gummy.

Example 23

Gummy Formulation

The method of Example 15 is repeated, with carageenan substituted for pectin as the gelling agent. The amount of CBN analog (1) in each 4 g gummy is 10 mg to 200 mg (0.25 wt. % to 5.0 wt. %), and the amount of *stevia* in each 4 g gummy is 1.58 g (39.5 wt. %). Carageenan, the gelling agent, represents 5.0 wt. % of the gummy.

Example 24

Gummy Formulation

The method of Example 16 is repeated, with carageenan substituted for pectin as the gelling agent. The amount of CBN analog (1) in each 4 g gummy is 10 mg to 200 mg (0.25 wt. % to 5.0 wt. %), and the combined amount of erythritol and *stevia* in each 4 g gummy is 1.58 g (39.5 wt. %). Carageenan, the gelling agent, represents 5.0 wt. % of the gummy.

Examples 25-36

Gummy Formulations

The methods of Examples 13-24 are repeated with CBN analog (2) instead of CBN analog (1).

Examples 37-48

Gummy Formulations

The methods of Examples 13-24 are repeated with CBN analog (3) instead of CBN analog (1).

The gummy formulations prepared according to Examples 13-48 thus have the compositions set forth in Table 5:

TABLE 5

| Example No. | CBN Analog | Sweetener | Gelling Agent | Remaining Components |
|---|---|---|---|---|
| 13 | (1) | sucrose | pectin | water, misc. excipients |
| 14 | (1) | erythritol | pectin | " |
| 15 | (1) | stevia | pectin | " |
| 16 | (1) | erythritol + stevia | pectin | " |
| 17 | (1) | sucrose | agar gum | " |
| 18 | (1) | erythritol | agar gum | " |
| 19 | (1) | stevia | agar gum | " |
| 20 | (1) | erythritol + stevia | agar gum | " |
| 21 | (1) | sucrose | carageenan | " |
| 22 | (1) | erythritol | carageenan | " |
| 23 | (1) | stevia | carageenan | " |
| 24 | (1) | erythritol + stevia | carageenan | " |
| 25 | (2) | sucrose | pectin | " |
| 26 | (2) | erythritol | pectin | " |
| 27 | (2) | stevia | pectin | " |
| 28 | (2) | erythritol + stevia | pectin | " |
| 29 | (2) | sucrose | agar gum | " |
| 30 | (2) | erythritol | agar gum | " |
| 31 | (2) | stevia | agar gum | " |
| 32 | (2) | erythritol + stevia | agar gum | " |
| 33 | (2) | sucrose | carageenan | " |
| 34 | (2) | erythritol | carageenan | " |
| 35 | (2) | stevia | carageenan | " |
| 36 | (2) | erythritol + stevia | carageenan | " |
| 37 | (3) | sucrose | pectin | " |
| 38 | (3) | erythritol | pectin | " |
| 39 | (3) | stevia | pectin | " |
| 40 | (3) | erythritol + stevia | pectin | " |
| 41 | (3) | sucrose | agar gum | " |
| 42 | (3) | erythritol | agar gum | " |
| 43 | (3) | stevia | agar gum | " |

TABLE 5-continued

| Example No. | CBN Analog | Sweetener | Gelling Agent | Remaining Components |
|---|---|---|---|---|
| 44 | (3) | erythritol + stevia | agar gum | " |
| 45 | (3) | sucrose | carageenan | " |
| 46 | (3) | erythritol | carageenan | " |
| 47 | (3) | stevia | carageenan | " |
| 48 | (3) | erythritol + stevia | carageenan | " |

It will be appreciated by those of ordinary skill in the art that additional sweeteners, gelling agents, and excipients can be substituted for those delineated in the foregoing examples. Furthermore, any CBN analog of the invention can be substituted for CBN analogs (1), (2), and (3).

Example 49

Compressed Tablet Dosage Form

A compressed tablet formulated for oral administration of CBN analog (1) is prepared by combining the CBN analog with microcrystalline cellulose as a filler; lactose, also as a filler; magnesium stearate as a lubricant; hydroxypropylmethylcellulose as a binder; and optionally a disintegrant such as potato starch, croscarmelose, or sodium starch glycolate. The mixture is compacted into individual tablets using conventional means, e.g., direct compression (DC). The composition of each tablet is 0.25 wt. % to 50 wt. % CBN analog; 15 wt. % to 75 wt. % filler; 0.1 wt. % to 1 wt. % lubricant; 0.5 wt. % to 5 wt. % binder; and zero to 10 wt. % disintegrant.

Example 50

Compressed Tablet Dosage Form

The method and components of Example 49 are repeated with CBN analog (2) substituted for CBN analog (1) as the active agent.

Example 51

Compressed Tablet Dosage Form

The method and components of Example 49 are repeated with CBN analog (3) substituted for CBN analog f as the active agent.

Other fillers, lubricants, binders, disintegrants, may be substituted for those set forth in Examples 49-51 by reference to Section IV of the Detailed Description or to the pertinent literature and texts relating to the manufacture of pharmaceutical dosage forms.

Example 52

Intravaginal Suppository

A suppository is formulated using conventional formulation techniques, e.g., molding, cold compression, or hand rolling, as described in Remington's, supra, and elsewhere. A CBN analog of the invention, e.g., CBN analog (1), (2), or (3), is incorporated into a base of cocoa butter, polyethylene glycol(s), and/or esterified, fractionated, or hydrogenated vegetable oil(s), or the like, in an amount to provide a suppository in which the CBN analog represents 0.25 wt. % to 50 wt. % of the dosage form and the suppository base represents 15 wt. % to 75 wt. % of the dosage form.

Example 53

Cream

A pharmaceutical cream containing a CBN analog of the invention, e.g., CBN analog (1), (2), or (3), is prepared as follows. Separate oil and water phases are prepared, with the oil phase containing wax, emollients, oils, or the like, and the water phase composed of water and water-soluble ingredients such as emulsifiers and thickeners. The two phases are combined under controlled conditions using high-speed mixing or homogenization, to create a stable emulsion. The selected CBN analog is dispersed therein and even distribution throughout the formulation is ensured. The amount of the selected CBN analog added to the emulsion is sufficient to provide a cream formulation with a concentration of 0.25 wt. % to 50 wt. % of the CBN analog.

The invention claimed is:

1. A cannabinol (CBN) analog having the structure of formula (I)

wherein:

(I)

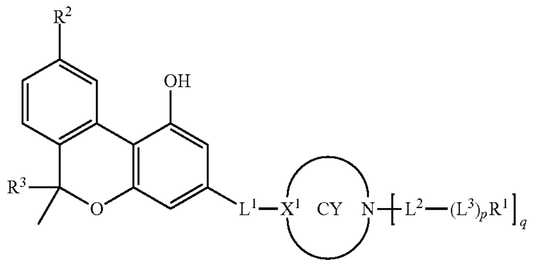

$L^1$ is selected from $C_1$-$C_3$ alkylene, $C_2$-$C_3$ alkenylene, hydroxyl-substituted $C_1$-$C_3$ alkylene, hydroxyl-substituted $C_2$-$C_3$ alkenylene, fluorinated $C_1$-$C_3$ alkylene, fluorinated $C_2$-$C_3$ alkenylene, —O—, —(CO)—, —($SO_2$)—, —$NR^4$—, —$NR^4$—(CO)—, —(CO)—$NR^4$—, -and $NR^5$—(CO)—$NR^6$— wherein $R^4$, $R^5$, and $R^6$ are H or $C_1$-$C_3$ alkyl and $R^5$ and $R^6$ may be the same or different;

$L^2$ is selected from —(CO)— and —($SO_2$)—;

$L^3$ is selected from —$CH_2$—, —NH—$CH_2$—, and —$CH_2$—N—;

p is zero or 1;

CY is a monocyclic or bicyclic group comprising 4-10 ring atoms and zero to 4 nonhydrogen substituents, any two of which may be linked to form a bridged bicyclic moiety, wherein CY is aliphatic or aromatic and has zero to 3 additional heteroatoms;

$X^1$ is selected from N, C, and CH, wherein when CY is aromatic, $X^1$ is N or C;

q is zero or 1;

$R^1$ is selected from $C_1$-$C_6$ alkyl, $C_2$-$C_6$ alkenyl, $C_2$-$C_6$ alkynyl, fluorinated $C_1$-$C_6$ alkyl, fluorinated $C_2$-$C_6$ alkenyl, fluorinated $C_2$-$C_6$ alkynyl, hydroxyl, $C_1$-$C_6$ alkoxy, carboxyl, carboxyl-substituted $C_1$-$C_6$ alkyl, carboxyl-substituted $C_2$-$C_6$ alkenyl, carboxyl-substituted $C_2$-$C_6$ alkynyl, cyano, cyano-substituted $C_1$-$C_6$ alkyl, cyano-substituted $C_2$-$C_6$ alkenyl, cyano-substituted $C_2$-$C_6$ alkynyl, monocyclic aryl, bicyclic aryl, monocyclic heteroaryl, and bicyclic heteroaryl;

$R^2$ is selected from H, $C_1$-$C_3$ alkyl, carboxyl, and $C_2$-$C_6$ alkoxycarbonyl; and $R^3$ is $C_1$-$C_3$ alkyl.

2. The CBN analog of claim 1, wherein $L^1$ is selected from —$CH_2$—, —CH(OH)—, —$CF_2$—, —CHF—, —O—, —($SO_2$)—, —(CO)—, —($SO_2$)—, —NH—, —NH—(CO)—, —(CO)—NH—, and —NH—(CO)—NH—.

3. The CBN analog of claim 2, wherein $L^1$ is —$CH_2$—.

4. The CBN analog of claim 3, wherein $L^2$ is —(CO)—.

5. The CBN analog of claim 4, wherein $R^1$ is fluorinated $C_1$-$C_3$ alkyl.

6. The CBN analog of claim 1, wherein $L^2$ is —(CO)—.

7. The CBN analog of claim 1, wherein CY is selected from azetidinyl, diazetidinyl, pyrrolidinyl, imidazolidinyl, pyrazolidinyl, piperidinyl, piperazinyl, pyrrolyl, imidazolyl, pyrazolyl, 1,2,3-triazolyl, 1,2,4-triazolyl, 1,3,4-triazolyl, tetrazolyl, pyridinyl, pyridazinyl, pyrimidinyl, pyrazinyl, and aza-bicyclo[4.1.1]octanyl.

8. The CBN analog of claim 1, wherein CY is aliphatic and $X^1$ is N or CH.

9. The CBN analog of claim 1, wherein CY is aromatic.

10. The CBN analog of claim 9, wherein $X^1$ is C.

11. The CBN analog of claim 9, wherein q is zero.

12. The CBN analog of claim 1, wherein $R^1$ is selected from $C_1$-$C_6$ alkyl, fluorinated $C_1$-$C_6$ alkyl, $C_2$-$C_6$ alkenyl, fluorinated $C_2$-$C_6$ alkenyl, hydroxyl, carboxyl, cyano, monocyclic aryl, and monocyclic heteroaryl.

13. The CBN analog of claim 12, wherein $R^1$ is selected from $C_1$-$C_3$ alkyl, fluorinated $C_1$-$C_3$ alkyl, $C_2$-$C_3$ alkenyl, fluorinated $C_2$-$C_3$ alkenyl, and cyano.

14. The CBN analog of claim 1, wherein $R^2$ and $R^3$ are methyl.

15. A pharmaceutical formulation comprising a therapeutically effective amount of the CBN analog of claim 1 and a pharmaceutically acceptable excipient.

16. The pharmaceutical formulation of claim 15, comprising an oral dosage form.

17. The pharmaceutical formulation of claim 15, comprising a suppository.

* * * * *